US008853178B2

(12) United States Patent
Bhanot et al.

(10) Patent No.: US 8,853,178 B2
(45) Date of Patent: Oct. 7, 2014

(54) ANTISENSE MODULATION OF PTP1B EXPRESSION

(75) Inventors: Sanjay Bhanot, Carlsbad, CA (US); Lex M. Cowsert, New Braunfels, TX (US); Jacqueline R. Wyatt, Sundance, WY (US); Brett P. Monia, Encinitas, CA (US); Madelline M. Butler, Rancho Santa Fe, CA (US); Robert McKay, Poway, CA (US); Susan M. Freier, San Diego, CA (US); Kenneth W. Dobie, Del Mar, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 384 days.

(21) Appl. No.: 13/177,462

(22) Filed: Jul. 6, 2011

(65) Prior Publication Data

US 2012/0077862 A1   Mar. 29, 2012

Related U.S. Application Data

(63) Continuation of application No. 12/046,421, filed on Mar. 11, 2008, now Pat. No. 8,017,760, which is a continuation of application No. 11/194,776, filed on Aug. 1, 2005, now abandoned, which is a continuation of application No. PCT/US2004/002003, filed on Feb. 6, 2004, which is a continuation-in-part of application No. 10/360,510, filed on Feb. 7, 2003, now Pat. No. 7,179,796, which is a continuation-in-part of application No. 09/854,883, filed on May 14, 2001, now abandoned, said application No. 12/046,421 is a continuation-in-part of application No. 11/008,747, filed on Dec. 9, 2004, now Pat. No. 7,563,884, which is a continuation of application No. 09/854,883, filed on May 14, 2001, now abandoned.

(51) Int. Cl.
*C12N 15/113* (2010.01)

(52) U.S. Cl.
CPC .......... *C12N 15/113* (2013.01); *C12N 2310/11* (2013.01); *C12N 2310/3341* (2013.01); *C12N 2310/315* (2013.01); *C12N 2310/321* (2013.01)
USPC ....................................... 514/44 A; 536/24.5

(58) Field of Classification Search
None
See application file for complete search history.

(56) References Cited

U.S. PATENT DOCUMENTS

| 5,726,027 | A | 3/1998 | Olefsky |
| 5,801,154 | A | 9/1998 | Baracchini et al. |
| 6,261,840 | B1 | 7/2001 | Cowsert et al. |
| 6,261,849 | B1 | 7/2001 | Lee |
| 6,506,559 | B1 | 1/2003 | Fire et al. |
| 6,582,908 | B2 | 6/2003 | Fodor et al. |
| 6,602,857 | B1 | 8/2003 | Cowsert et al. |
| 2002/0055479 | A1 | 5/2002 | Cowsert et al. |
| 2003/0220282 | A1 | 11/2003 | Cowsert et al. |
| 2004/0005618 | A1 | 1/2004 | Yu et al. |
| 2004/0009946 | A1 | 1/2004 | Lewis et al. |
| 2004/0019001 | A1 | 1/2004 | McSwiggen |
| 2005/0070497 | A1 | 3/2005 | McSwiggen et al. |
| 2005/0095710 | A1 | 5/2005 | Cowsert et al. |

FOREIGN PATENT DOCUMENTS

| WO | WO 97/32595 | 9/1997 |
| WO | WO 98/20024 | 5/1998 |
| WO | WO 01/05954 | 1/2001 |
| WO | WO 01/07655 | 1/2001 |
| WO | WO 01/16312 | 3/2001 |
| WO | WO 01/30801 | 5/2001 |
| WO | WO 01/53528 | 7/2001 |
| WO | WO 02/59137 | 1/2002 |
| WO | WO 02/10378 | 2/2002 |
| WO | WO 02/44321 | 6/2002 |
| WO | WO 02/092772 | 11/2002 |
| WO | WO 03/070881 | 8/2003 |
| WO | WO 03/099227 | 12/2003 |
| WO | WO 2004/016735 | 2/2004 |
| WO | WO 2004/046161 | 6/2004 |
| WO | WO 2004/071407 | 8/2004 |
| WO | WO 2005/021572 | 3/2005 |

OTHER PUBLICATIONS

U.S. Appl. No. 09/629,644, filed Jul. 31, 2000, Cowsert et al.
Adjei et al., "A Phase I trial of ISIS 2503, an antisense inhibitor of H-ras, in combination with gemcitabine in patients with advanced cancer" Clinical Cancer Research (2003) 9:115-123.
Ahmad et al., "Improved Sensitivity to Insulin in Obese Subjects Following Weight Loss is Accompanied by Reduced Protein-Tyrosine Phosphatases in Adipose Tissue" *Metabolism* (1997) 46:1140-1145.
Arregui et al., "Impaired integrin-mediated adhesion and signaling in fibroblasts expressing a dominant-negative mutant PTP1B" *J. Cell. Biol.* (1998) 143:861-873.
Asante-Appiah et al., "Protein tyrosine phosphatase: the quest for negative regulators of insulin action" *Am. J. Physiol. Endocrinol. Metab.* (2003) 284:E663-E670.
Balsamo et al., "The nonreceptor protein tyrosine phosphatase PTP1B binds to the cytoplasmic domain of N-cadherin and regulates the cadherin-actin linkage" *J. Cell. Biol.* (1998) 143:523-532.
Bhanot et al., "A Novel PTP-1B Antisense Inhibitor (ISIS 113715) Improves Insulin Sensitivity in Obese Hyperinsulinemic Rhesus Monkeys" *ADA Annual Meeting* (2003) Abstract 477-P.
Branch et al., "A good antisense molecule is hard to fin" *TIBS* (1998) 23:45-50.

(Continued)

*Primary Examiner* — Tracy Vivlemore
(74) *Attorney, Agent, or Firm* — Isis Pharmaceuticals, Inc Patent Dept. Knobbe Martens

(57) ABSTRACT

Compounds, compositions and methods are provided for modulating the expression of PTP1B. The compositions comprise antisense compounds, particularly antisense oligonucleotides, targeted to nucleic acids encoding PTP1B. Methods of using these compounds for modulation of PTP1B expression and for treatment of diseases associated with expression of PTP1B are provided.

18 Claims, No Drawings

(56) References Cited

OTHER PUBLICATIONS

Brown-Shimer et al., "Effect of protein tyrosine phosphatase 1B expression on transformation by the human neu oncogene" *Cancer Res.* (1992) 52:478-482.

Cheetham et al., "Novel targets for the treatment of obesity: a review of progress" *Drug Discovery Today: Therapeutic Strategies* (2004) 1:227-235.

Chen et al., "A phosphotyrosyl mimetic peptide reverses impairment of insulin-stimulated transolcation of GLUT4 caused by overexpression of PTP1B in rat adipose cells" *Biochemistry* (1999) 38:384-389.

Chen et al., "Protein-tyrosine phosphatases PTP1B and syp are modulators of insulin-stimulated translocation of GLUT4 in transfected rat adipose cells" *J. Biol. Chem.* (1997) 272:8026-8031.

Chernoff et al., "Cloning of a cDNA for a Major Human Protein-Tyrosine-Phosphatase" Proc. Natl. Acad. Sci. USA (1990) 87:2735-2739.

Chin, "On the preparation and Utilization of Isolated and Purified Oligonucleotides" Document purportedly located on a CD-ROM and contributed to the public collection of the Katherine R. Everett Law Library of the University of North Carolina on Mar. 14, 2002.

Clampit et al., "Reduction of protein-tyrosine phosphatase-1B increases insulin signaling in FAO hepatoma cells" *Biochem. Biophys. Res. Commun.* (2003) 300:261-267.

Cox et al., "Absorption, disposition, and metabolism of rosigitazone, a potent thiazolidinedione insulin sensitizer, in humans" *Drug Metabolism and Disposition* (2000) 28:772-780.

Crooke et al., "Basic Principles of Antisense Therapeutics" Antisense Research and Application (1998) Chapter 1:1-50.

Crystal et al., "Transfer of genes to humans: early lessons and obstacles to success" Science (1995) 270:404-410.

Database EMBL accession No. AX418625, 2002.
Database EMBL accession No. AX418771, 2002.
Database GENESEQ accession No. ABA00067, 2002.

Day, "Thiazolidinediones: a new class of antidiabetic drugs" *Diabetic Medicine* (1999) 16:179-192.

Desmarais et al., "Inhibition of protein tyrosine phosphatases PTP1B and CD45 by sulfotyrosyl peptides" *Arch. Biochem. Biophys.* (1998) 354:225-231.

Elchebly et al., "Increased insulin sensitivity and obesity resistance in mice lacking the protein tyrosine phosphatase-1B gene" Science (1999) 283:1544-1548.

Ferber, "New Clues Found to Diabetes and Obesity" Science (1999) 283:1423-1424.

Friedmann et al., "Overcoming the Obstacles to gene therapy" Scientific American (1997) 276:96-101.

Goldstein et al., "Regulation of the insulin signalling pathway by ceullular protein-tyrosine phosphatases" *Mol. Cell. Biochem.* (1998) 182:91-99.

Goldstein et al., "Protein-Tyrosine Phosphatase 1B (PTP1B): A Novel Therapeutic Target for Type 2 Diabetes Mellitus, Obesity and Related States of Insulin Resistance" *Curr. Drug Targets—Immun. Endocrin. Metab. Disorders* (2001) 1:265-275.

Goldstein et al., "Tests of Glycemia in Diabetes" *Diabetes Care* (2004) 27:1761-1773.

Graham et al., "In Vivo Distribution and Metabolism of a Phosphorothioate Oligonucleotides Within Rat Liver after Intravenous Administration" J. Pharm. Exp. Ther. (1998) 286:447-458.

Guan et al., "Cloning and Expression of Protein-Tyrosine-Phosphatase" Proc. Natl. Acad. Sci. USA (1990) 87:1501-1505.

Gum et al., "Antisense Protein Tyrosine Phosphatase 1B Reverses Activation of p38 Mitogen-Activated Protein Kinase in Liver of ob/ob Mice" *Molecular Endocrin.* (2003) 17:1131-1143.

Gum et al., "Reduction of Protein Tyrosine Phosphatase 1B Increases Insulin-Dependent Signaling in ob/ob Mice" *Diabetes* (2003) 52:21-28.

Ham et al., "Selective inactivation of protein tyrosine phosphatase PTP1B by sulfone analogue of naphthoquinone" *Bioorg. Med. Chem. Lett.* (1999) 9:185-186.

Hassid et al., "Antisense oligonucleotides against protein tyrosine phosphatase 1B increase focal adhesion protein phosphorylation and migration in rat aortic smooth muscle cells" in Supplement to Circulation, Journal of the American Heart Association, Abstracts from 71st Scientific Sessions (1998) Abstract No. 1733.

Hassid et al., "NO Alters Cell Shape and Motility in Aortic Smooth Muscle Cells via Protein Tyrosine Phosphatase 1B Activation" Am. J. Phys. (1999) 277:H1014-1026.

Hassid et al., "Role of PTP1B in Aortic Smooth Muscle Cell Motility and Tyrosine Phosphorylation of Focal Adhesion Proteins" Am. J. Phys. (1999) 277:H192-198.

Henry et al., "Toxicology and Pharmacokinetic Properties of Chemically Modified Antisense Oligonucleotide Inhibitors of PKC-Alpha and C-Raf Kinase" Anti-Cancer Drug Design (1997) 12:409-420.

Ho et al., "Mapping or RNA Accessible Sites for Antisense Experiments with Oligonucleotide Libraries" Nature Biotech. (1998) 16:59-63.

Hormes et al., "The subcellular localization and length of hammerhead ribozymes determine efficacy in human cells" Nucleic Acids Res. (1997) 25:769-775.

Huang et al., "Antisense to protein tyrosine phosphatase 1B increases Tyrosine Phosphorylation of Focal Adhesion Protein in Aortic Smooth Muscle Cells of Rats" FASEB (1998) 12:A188, Abstract No. 1099.

James et al., "Towards Gene-Inhibition Therapy: A Review of Progress and Prospects in the Field of Antiviral Antisense Nucleic Acids and Ribozymes" Antiviral Chem. And Chemotherapy (1991) 2:191-214.

Kjems et al., "Increased Insulin Sensitivity in Humans by Protein Tyrosine Phosphatase 1B (PTP-1B) Inhibition-Evaluation of ISIS 113715, an Antisense Inhibitor of PTP-1B" San Diego *ADA Annual Meeting* (2005) Abstract 2201-PO.

Lamontagne et al., "Protein tyrosine phosphatase PTP1B suppresses p210 bcr-abl-induced transformation of rat-1 fibroblasts and promotes differentiation of K562 cells" *Proc. Natl. Acad. Sci. USA* (1998) 95:14094-14099.

Lee et al., "Reversible inactivation of protein-tyrosine phosphatase 1B in A431 cells stimulated with epidermal growth factor" *J. Biol. Chem.* (1998) 273:15366-15372.

Liu et al., "Protein tyrosine phosphatase 1B interacts with and is tyrosine phosphorylated by the epidermal growth factor receptor" Biochem. J. (1997) 327:139-145.

Liu et al., "Protein tyrosine phosphatase 1B negatively regulates integrin signaling" *Curr. Biol.* (1998) 8:173-176.

Liu et al., "Transformation suppression by protein tyrosine phosphatase 1B requires a functional SH3 ligand" *Mol. Cell. Biol.* (1998) 18:250-259.

Liu et al., "Protein tyrosine phosphatase 1B as a target for the treatment of impaired glucose tolerance and Type II diabetes" *Curr. Opin. Invest. Drugs* (2002) 3:1608-1616.

Liu, "Technology evaluation: ISIS-113715, Isis," *Curr. Opin. Mol. Therap.* (2004) 6:331-336.

Mani et al., "Phase I clinical and pharmacokinetic study of protein kinase C-a antisense oligonucleotide ISIS 3521 administered in combination with 5-fluorouracil and leucovorin in patients with advanced cancer" Clinical Cancer Research (2002) 8:1042-1048.

McKay et al., "Effects of a Novel PTP-1B Antisense Oligonucleotide Inhibitor (ISIS 113715) on PTP-1B Expression in Different Liver Cell Types" *ADA Annual Meeting* (2003) Abstract 611-P.

Milner et al., "Selecting effective antisense reagents on combinatorial oligonucleotide arrays" Nature (1997) 15:537-541.

Moller et al., "Protein tyrosine phosphatases (PTPs) as drug targets: Inhibitors of PTP1B for the treatment of diabetes" *Curr. Opin. Drug Discov. Dev.* (2000) 3:527-540.

Monia, "Protein Phosphatases" *FASEB Summer Conference presentation on Protein Phosphatases* in Colorado, Jul. 23-28, 2000, poster presentation, 14 pages.

Monia, "Protein Phosphatases" *FASEB Summer Conference presentation on Protein Phosphatases* in Colorado, Jul. 23-28, 2000, oral presentation, 20 pages.

(56) References Cited

OTHER PUBLICATIONS

Murray et al., "Additive Glucose Lowering Effects of a Novel PTP-1B Antisense Oligonucleotide (ISIS 113715) with Rosiglitazone and Metformin in ZDF Rats" San Diego *ADA Annual Meeting* (2005) Abstract 1545-P.
New England Biolabs 1998/1999 Catalog, cover page, pp. 121 and 284.
Nuss et al., "Effects of Protein Tyrosine Phosphatase 1B (PTP1B) Antisense Oligonucleotide (ASO) Treatment on Fat Volume Using MRI in Zucker Fatty Rats" *Diabetes* (2001) 50:A377.
Palu et al., "In Pursuit of new developments for gene therapy of human disease" J. Biotech. (1999) 68:1-13.
Peracchi et al., "Prospects for antiviral ribozymes and deoxyribozymes" Rev. in Med. (2004) 14:47-64.
Pihl-Carey, "Isis to Restructure as Crohn's Disease Drug Fails in Phase III" Bio World Today (The Daily Biotechnology Newspaper) (1999) 10:1-2.
Roller et al., "Potent inhibition of protein-tyrosine phosphatase-1B using the phosphotyrosyl mimetic fluoro-O-malonyl tyrosine (FOMT)" *Bioorg. Med. Chem. Lett.* (1998) 8:2149-2150.
Rondinone et al., "Inhibition of PTP1B Induces Differential Expression of P13-Kinase Regulatory Subunit (p85alpha) Isoforms" *Diabetes* (2001) 50:A400.
Rondinone et al., "Protein Tyrosine Phosphatase 1B Reduction Regulates Adiposity and Expression of Genes Involved in Lipogenesis" *Diabetes* (2002) 51:2405-2411.
Schievella et al., "Protein tyrosine phosphatase 1B undergoes mitosis-specific phosphorylation on serine" *Cell. Growth Differ.* (1993) 4:239-246.
Schofield et al., "Non-viral approaches to gene therapy" Brit. Med. Bull. (1995) 51:56-71.
Seely et al., "Protein tyrosine phosphatase 1B interacts with the activated insuliun receptor" *Diabetes* (1996) 45:1379-1385.
Sell et al., "Insulin-inducible changes in the relative ratio of PTP1B splice variants" *Mol. Genet. Metab.* (1999) 66:189-192.
Shifrin et al., "Growth factor-inducible alternative splicing of nontransmembrane phosphotyrosine phosphatase PTP1B pre-mRNA" *J. Biol. Chem.* (1993) 268:25376-25384.
Skorey et al., "How does alendronate inhibit protein-tyrosine phosphatases?" *J. Biol. Chem.* (1997) 272:22472-22480.
Standl et al., "Effect of acarbose on additional insulin therapy in type 2 diabetic patients with late failure of sulphonylurea therapy" *Diabetes, Obesity and Metabolism* (1999) 1:215-220.
Stein et al., "Antisense oligonucleotides as therapeutic agents—is the bullet really magical?" Science (1993) 261:1004-1012.
Stull et al., "An In Vitro Messenger RNA Binding Assay as a Tool for Identifying Hybridization-Competent Antisense Oligonucleotides" Antisense & Nucleic Acid Drug Development (1996) 6:221-228.
Strickland et al., "Antisense RNA Directed Against the 3' Noncoding Region Prevents Dormant mRNA Activation in Mouse Oocytes" Science (1988) 241:680-684.
Taing et al., "Potent and highly selective inhibitors of the protein tyrosine phosphatase 1B" *Biochemistry* (1999) 38:3793-3803.
Taylor et al., "Potent non-peptidyl inhibitors of protein tyrosine phosphatase 1B [published erratum appears in Bioorg Med Chem Nov. 1998;6(11):2235]" *Bioorg. Med. Chem.* (1998) 6:1457-1468.
Tonks et al., "Characterization of the major protein-tyrosine-phosphatases of human placenta" *J. Biol. Chem.* (1998) 263:6731-6737.
Tonks et al., "Purification of the major protein-tyrosine-phosphatases of human placenta" *J. Biol. Chem.* (1998) 263: 6722-6730.
Verma et al., "Gene Therapy: promises, problems and prospects" Nature (1997) 389:239-242.
Vickers et al., "Efficient reduction of target RNAs by small interfering RNA and Rnase H-dependent antisense agents" *The Journal of Biological Chemistry* (2003) 278:7108-7118.
Walczak, "Diabetes Technology News" Diabetes Technology & Therapeutics (2001) 3:307-331.

Wang et al., "Naphthalenebis [alpha, alpha-difluoromethylenephosphonates] as potent inhibitors of protein tyrosine phosphatases" *Bioorg. Med. Chem. Lett.* (1998) 8:345-350.
Wang et al., "Mechanism of inhibition of protein-tyrosine phosphatases by disodium aurothiomalate" *Biochem. Pharmacol.* (1997) 54:703-711.
Waring et al., "PTP1B antisense-treated mice show regulation of genes involved in lipogenesis in liver and fat" Mol. Cell. Endocrin. (2003) 203:155-168.
Wiener et al., "Overexpression of the Protein Tyrosine Phosphatase PTP1B in Human Breast Cancer: Association with p185 Protein Expression" *J. Nat. Cancer Inst.* (1994) 86:372-378.
Wiener et al., "Overexpression of the tyrosine phosphatase PTP1B is associated with human ovarian carcinomas" *Am. J. Obstet. Gynecol.* (1994) 170:1177-1183.
Wu et al., "Rosiglitazone ameliorates abnormal expression and activity of protein tyrosine phosphatase 1B in the skeletal muscle of fat-fed, streptozotocin-treated diabetic rats" Br. J. Pharm. (2005) 146:234-243.
Yao et al., "Structure-based design and synthesis of small molecule protein-tyrosine phsphatase 1B inhibitors" *Bioorg. Med. Chem.* (1998) 6:1799-1810.
Yu et al., "Abstract of International Patent Publication No. WO-02/59137" published Aug. 1, 2002.
Zhang et al., "Protein-tyrosine phosphatases: biological function, structural characteristics, and mechanism of catalysis" *Crit. Rev. Biochem. Mol. Biol.* (1998) 33:1-52.
Zinker et al., "PTP1B antisense oligonucleotide lowers PTP1B protein, normalizes blood glucose, and improves insulin sensitivity in diabetic mice" *PNAS* (2002) 99:11357-11362.
Office Action for U.S. Appl. No. 09/487,368 dated Oct. 3, 2000.
Office Action for U.S. Appl. No. 11/008,747 dated Sep. 26, 2007.
Office Action for U.S. Appl. No. 09/629,644 dated Jul. 13, 2001.
Office Action for U.S. Appl. No. 09/854,883 dated Nov. 7, 2002.
Office Action for U.S. Appl. No. 09/854,883 dated Jun. 27, 2003.
Office Action for U.S. Appl. No. 09/854,883 dated Jul. 13, 2004.
Office Action for U.S. Appl. No. 10/360,510 dated Oct. 3, 2005.
Office Action for U.S. Application No. 11/251,610 dated Nov. 30, 2006.
Office Action for U.S. Appl. No. 11/251,610 dated Jun. 13, 2008.
Final Rejection for U.S. Appl. No. 09/629,644 dated Dec. 31, 2001.
Final Rejection for U.S. Appl. No. 11/251,610 dated Jun. 21, 2007.
Restriction Requirement for U.S. Appl. No. 11/008,747 dated Mar. 30, 2007.
Restriction Requirement for U.S. Appl. No. 11/194,776 dated Sep. 11, 2007.
Restriction Requirement for U.S. Appl. No. 09/854,883 dated Aug. 22, 2002.
Restriction Requirement for U.S. Appl. No. 11/251,610 dated Sep. 28, 2006.
Notice of Allowance for U.S. Appl. No. 09/487,368 dated Mar. 8, 2001.
Notice of Allowance for U.S. Appl. No. 11/008,747 dated Jun. 5, 2008.
Notice of Allowance for U.S. Appl. No. 09/629,644 dated Jul. 5, 2002.
Notice of Allowance for U.S. Appl. No. 09/629,644 dated Mar. 25, 2003.
Notice of Allowance for U.S. Appl. No. 10/360,510 dated Mar. 15, 2006.
European Supp. Search Report for EP 01900829.1 dated Aug. 16, 2004.
European Supp. Partial Search Report for EP 02736842.2 dated Nov. 19, 2004.
European Supp. Partial Search Report for EP 02736842.2 dated Jan. 14, 2005.
European Partial Search Report for Application EP 08008871.9 dated Nov. 10, 2008.
European Notice of Opposition for Application EP 01900829.1 dated Nov. 12, 2008.
International Search Report for PCT/US01/00109 dated Apr. 11, 2001.

(56) References Cited

OTHER PUBLICATIONS

International Search Report for PCT/US01/23874 dated Nov. 26, 2002.
International Search Report for PCT/US02/15301 dated Dec. 4, 2002.
International Search Report for PCT/US04/002003 dated Nov. 1, 2005.
International Search Report for PCT/US05/036813 dated Jun. 1, 2006.

ANTISENSE MODULATION OF PTP1B EXPRESSION

CROSS REFERENCE TO RELATED APPLICATIONS

This application is a continuation of U.S. application Ser. No. 12/046,421, filed Mar. 11, 2008, allowed May 5, 2011, which is a continuation of U.S. application Ser. No. 11/194,776, filed Aug. 1, 2005, which is a continuation of PCT Application No. PCT/US04/002003, filed Feb. 6, 2004, which is a continuation-in-part of U.S. application Ser. No. 10/360,510 filed Feb. 7, 2003, which is a continuation-in-part of U.S. application Ser. No. 09/854,883, each of which is incorporated herein by reference in its entirety. U.S. application Ser. No. 12/046,721 is also a continuation-in-part of U.S. application Ser. No. 11/008,747, filed Dec. 9, 2004, which is a continuation of U.S. application Ser. No. 09/854,883, filed May 14, 2001, each of which is incorporated herein by reference in its entirety.

SEQUENCE LISTING

The present application is being filed along with a Sequence Listing in electronic format. The Sequence Listing is provided as a file entitled BIOL0001 USC4SEQ.txt, created on Jul. 6, 2011 which is 188 Kb in size. The information in the electronic format of the sequence listing is incorporated herein by reference in its entirety.

BACKGROUND OF THE INVENTION

The process of phosphorylation, defined as the attachment of a phosphate moiety to a biological molecule through the action of enzymes called kinases, represents one course by which intracellular signals are propagated resulting finally in a cellular response. Within the cell, proteins can be phosphorylated on serine, threonine or tyrosine residues and the extent of phosphorylation is regulated by the opposing action of phosphatases, which remove the phosphate moieties. While the majority of protein phosphorylation within the cell is on serine and threonine residues, tyrosine phosphorylation is modulated to the greatest extent during oncogenic transformation and growth factor stimulation (Zhang, *Crit. Rev. Biochem. Mol. Biol.,* 1998, 33, 1-52).

Because phosphorylation is such a ubiquitous process within cells and because cellular phenotypes are largely influenced by the activity of these pathways, it is currently believed that a number of disease states and/or disorders are a result of either aberrant activation of, or functional mutations in, kinases and phosphatases. Consequently, considerable attention has been devoted recently to the characterization of tyrosine kinases and tyrosine phosphatases.

PTP1B (also known as protein phosphatase 1B and PTPN1) is an endoplasmic reticulum (ER)-associated enzyme originally isolated as the major protein tyrosine phosphatase of the human placenta (Tonks et al., *J. Biol. Chem.,* 1988, 263, 6731-6737; Tonks et al., *J. Biol. Chem.,* 1988, 263, 6722-6730).

An essential regulatory role in signaling mediated by the insulin receptor has been established for PTP1B. PTP1B interacts with and dephosphorylates the activated insulin receptor both in vitro and in intact cells resulting in the down-regulation of the signaling pathway (Goldstein et al., *Mol. Cell. Biochem.,* 1998, 182, 91-99; Seely et al., *Diabetes,* 1996, 45, 1379-1385). In addition, PTP1B modulates the mitogenic actions of insulin (Goldstein et al., *Mol. Cell. Biochem.,* 1998, 182, 91-99). In rat adipose cells overexpressing PTP1B, the translocation of the GLUT4 glucose transporter was inhibited, implicating PTP1B as a negative regulator of glucose transport as well (Chen et al., *J. Biol. Chem.,* 1997, 272, 8026-8031).

Mouse knockout models lacking the PTP1B gene also point toward the negative regulation of insulin signaling by PTP1B. Mice harboring a disrupted PTP1B gene showed increased insulin sensitivity, increased phosphorylation of the insulin receptor and when placed on a high-fat diet, PTP1B−/− mice were resistant to weight gain and remained insulin sensitive (Elchebly et al., *Science,* 1999, 283, 1544-1548). These studies clearly establish PTP1B as a therapeutic target in the treatment of diabetes and obesity.

PTP1B, which is differentially regulated during the cell cycle (Schievella et al., *Cell. Growth Differ.,* 1993, 4, 239-246), is expressed in insulin sensitive tissues as two different isoforms that arise from alternate splicing of the pre-mRNA (Shifrin and Neel, *J. Biol. Chem.,* 1993, 268, 25376-25384). It was recently demonstrated that the ratio of the alternatively spliced products is affected by growth factors such as insulin and differs in various tissues examined (Sell and Reese, *Mol. Genet. Metab.,* 1999, 66, 189-192). In these studies it was also found that the levels of the variants correlated with the plasma insulin concentration and percentage body fat and may therefore be used as a biomarker for patients with chronic hyperinsulinemia or type 2 diabetes.

Liu and Chernoff have shown that PTP1B binds to and serves as a substrate for the epidermal growth factor receptor (EGFR) (Liu and Chernoff, *Biochem. J.,* 1997, 327, 139-145). Furthermore, in A431 human epidermoid carcinoma cells, PT1B was found to be inactivated by the presence of $H_2O_2$ generated by the addition of EGF. These studies indicate that PTP1B can be negatively regulated by the oxidation state of the cell, which is often deregulated during tumorigenesis (Lee et al., *J. Biol. Chem.,* 1998, 273, 15366-15372).

Overexpression of PTP1B has been demonstrated in malignant ovarian cancers and this correlation was accompanied by a concomitant increase in the expression of the associated growth factor receptor (Wiener et al., *Am. J. Obstet. Gynecol.,* 1994, 170, 1177-1183).

PTP1B has been shown to suppress transformation in NIH3T3 cells induced by the neu oncogene (Brown-Shimer et al., *Cancer Res.,* 1992, 52, 478-482), as well as in rat 3Y1 fibroblasts induced by v-srk, v-src, and v-ras (Liu et al., *Mol. Cell. Biol.,* 1998, 18, 250-259) and rat-1 fibroblasts induced by bcr-abl (LaMontagne et al., *Proc. Natl. Acad. Sci. U.S.A.,* 1998, 95, 14094-14099). It has also been shown that PTP1B promotes differentiation of K562 cells, a chronic myelogenous leukemia cell line, in a similar manner as does an inhibitor of the bcr-abl oncoprotein. These studies describe the possible role of PTP1B in controlling the pathogenesis of chronic myeloid leukemia (LaMontagne et al., *Proc. Natl. Acad. Sci. U.S.A.,* 1998, 95, 14094-14099).

PTP1B negatively regulates integrin signaling by interacting with one or more adhesion-dependent signaling components and repressing integrin-mediated MAP kinase activation (Liu et al., *Curr. Biol.,* 1998, 8, 173-176). Other studies designed to study integrin signaling, using a catalytically inactive form of PTP1B, have shown that PTP1B regulates cadherin-mediated cell adhesion (Balsamo et al., *J. Cell. Biol.,* 1998, 143, 523-532) as well as cell spreading, focal adhesion and stress fiber formation and tyrosine phosphorylation (Arregui et al., *J. Cell. Biol.,* 1998, 143, 861-873).

Currently, therapeutic agents designed to inhibit the synthesis or action of PTP1B include small molecules (Ham et al., *Bioorg. Med. Chem. Lett.,* 1999, 9, 185-186; Skorey et al.,

*J. Biol. Chem.*, 1997, 272, 22472-22480; Taing et al., *Biochemistry*, 1999, 38, 3793-3803; Taylor et al., *Bioorg. Med. Chem.*, 1998, 6, 1457-1468; Wang et al., *Bioorg. Med. Chem. Lett.*, 1998, 8, 345-350; Wang et al., *Biochem. Pharmacol.*, 1997, 54, 703-711; Yao et al., *Bioorg. Med. Chem.*, 1998, 6, 1799-1810) and peptides (Chen et al., *Biochemistry*, 1999, 38, 384-389; Desmarais et al., *Arch. Biochem. Biophys.*, 1998, 354, 225-231; Roller et al., *Bioorg. Med. Chem. Lett.*, 1998, 8, 2149-2150). In addition, disclosed in the PCT publication WO 97/32595 (Olefsky, 1997) are phosphopeptides and antibodies that inhibit the association of PTP1B with the activated insulin receptor for the treatment of disorders associated with insulin resistance. Antisense nucleotides against PTP1B are also generally disclosed.

There remains a long felt need for additional agents capable of effectively inhibiting PTP1B function.

SUMMARY OF THE INVENTION

Contemplated herein are compounds comprising a sense region and an antisense region, said antisense region comprising an antisense compound targeted to PTP1b. Also contemplated are compounds comprising a sense region and an antisense region, said antisense region comprising a sequence exemplified herein. In a preferred embodiment, the compounds specifically hybridize with a nucleic acid molecule encoding PTP1B and inhibit the expression of PTP1B. In some embodiments, the antisense region and the sense region are separate molecules. In some embodiments, the antisense region and the sense region are part of a single molecule.

Further contemplated are antisense regions comprising a stretch of at least eight (8) consecutive nucleobases of sequences described herein, preferably of SEQ ID NO: 18, 19, 20, 21, 22, 23, 24, 26, 27, 29, 30, 32, 33, 35, 36, 38, 39, 40, 42, 45, 46, 47, 48, 49, 50, 52, 53, 54, 55, 56, 57, 58, 59, 60, 61, 62, 63, 64, 65, 66, 67, 69, 70, 72, 73, 75, 78, 79, 80, 81, 83, 84, 86, 87, 89, 90, 92, 93, 94, 95, 96, 97, 99, 100, 101, 102, 103, 104, 106, 107, 108, 109, 110, 112, 113, 114, 115, 117, 120, 121, 122, 123, 124, 126, 127, 128, 130, 131, 133, 134, 135, 136, 137, 138, 139, 140, 141, 142, 144, 145, 146, 147, 148, 151, 152, 153, 154, 155, 156, 157, 158, 159, 160, 161, 162, 163, 164, 165, 166, 167, 168, 169, 170, 171, 172, 173, 177, 178, 179, 180, 181, 182, 183, 184, 185, 186, 187, 188, 189, 191, 193, 195, 196, 198, 201, 202, 204, 205, 206, 211, 215, 217, 219, 223, 225, 226, 228, 229, 230, 232, 233, 235, 236, 237, 239, 240, 244, 245, 247, 248, 249, 250, 251, 252, 254, 255, 256, 257, 258, 259, 260, 261, 262, 263, 267, 268, 269, 271, 275, 276, 277, 278, 279, 281, 282, 283, 288, 290, 291, 292, 294, 296, 297, 298, 299, 300, 302, 303, 307, 310, 311, 313, 315, 317, 318, 322, 323, 324, 325, 326, 327, 328, 329, 330, 331, 332, 333, 334, 335, 337, 340, 341, 342, 343, 344, 345, 347, 349, 350, 351, 352, 353, 354, 355, 356, 357, 358, 360, 361, 362, 363, 364, 365, 366, 368, 369, 371, 372, 373, 374, 375, 377, 378, 380, 381, 384, 385, 386, 387, 388, 389, 390, 391, 392, 393, 394, 395, 396, 397, or 398 wherein said compound specifically hybridizes with said nucleic acid molecule encoding PTP1B and inhibits the expression of PTP1B.

Further provided are compounds 8 to 50 nucleobases in length targeted to a nucleic acid molecule encoding PTP1B, wherein said compound comprises a sense region and an antisense region, said antisense region comprising a stretch of at least eight (8) consecutive nucleobases of SEQ ID NO: 390, 391, 392, 393, 394, 395, 396, 397, or 398 or comprising a stretch of at least eight (8) consecutive nucleobases of nucleobases 1 to 19 of SEQ ID NO: 390, 391, 392, 393, 394, or 395. In one embodiment, said sense region comprises a sequence complementary to the antisense region selected from sequences comprising a stretch of at least eight (8) consecutive nucleobases of SEQ ID NO: 403, 404, 405, 406, 407, 408, 409, 410, or 411 or comprising a stretch of at least eight (8) consecutive nucleobases of nucleobases 1 to 19 of SEQ ID NO: 403, 404, 405, 406, 407, or 408

Further provided are compounds 8 to 50 nucleobases in length targeted to a nucleic acid molecule encoding PTP1B, wherein said compound comprises a sense region and an antisense region, said antisense region comprising a stretch of at least eight (8) consecutive nucleobases of SEQ ID NO: 396, 397, or 398. In some embodiments, said sense region comprises a sequence complementary to said antisense region selected from sequences comprising a stretch of at least eight (8) consecutive nucleobases of SEQ ID NO: 409, 410, or 411.

Another aspect of the present invention are compounds 8 to 50 nucleobases in length targeted to a nucleic acid molecule encoding PTP1B, wherein said compound comprises a sense region and an antisense region, said antisense region comprising a stretch of at least eight (8) consecutive nucleobases of SEQ ID NO: 166.

In some embodiments, the antisense region and/or the sense region further comprise an overhang of two deoxynucleotides.

In some embodiments, the compound comprises at least one modified internucleoside linkage, such as a phosphorothioate linkage, a modified sugar moiety, and/or modified nucleobase. The compounds may be chimeric compounds in some embodiments.

Further contemplated are pharmaceutical compositions comprising the compounds of the invention and a pharmaceutically acceptable carrier, diluent, enhancer or excipient. Also contemplated is a method of inhibiting the expression of PTP1B in cells or tissues comprising contacting said cells or tissues with a compound of the invention so that expression of PTP1B is inhibited.

Another aspect of the present invention is a method of treating an animal having a disease or condition associated with PTP1B comprising administering to said animal a therapeutically or prophylactically effective amount of an antisense compound of the invention so that PTP1B is inhibited. In some embodiments, diseases or conditions include metabolic diseases or conditions. In some embodiments, diseases or conditions include diabetes, obesity, or hyperproliferative disorders including cancer. In some embodiments, the diabetes is Type 2 diabetes.

Other embodiments of the present invention are methods of decreasing blood glucose levels or plasma insulin levels or improving insulin sensitivity in an animal. In some embodiments, the animal is diabetic, hyperinsulinemic, insulin-resistant or obese. Also contemplated herein is the use of a compound of the present invention in the preparation of a medicament for a metabolic disease or condition, wherein said disease or condition is diabetes, including Type 2 diabetes, obesity, or a hyperproliferative condition.

DETAILED DESCRIPTION OF THE INVENTION

The present invention employs oligomeric antisense compounds, particularly oligonucleotides, for use in modulating the function of nucleic acid molecules encoding PTP1B, ultimately modulating the amount of PTP1B produced. This is accomplished by providing antisense compounds which specifically hybridize with one or more nucleic acids encoding PTP1B. As used herein, the terms "target nucleic acid" and "nucleic acid encoding PTP1B" encompass DNA encoding PTP1B, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense".

The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of PTP1B. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding PTP1B. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes has a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding PTP1B, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

The PTP1B inhibitors of the present invention effectively inhibit the activity of the PTP1B protein or inhibit the expression of the PTP1B protein. In one embodiment, the activity or expression of PTP1B is inhibited by about 10%. Preferably, the activity or expression of PTP1B is inhibited by about 30%. More preferably, the activity or expression of PTP1B is inhibited by 50% or more. Thus, the oligomeric antisense compounds modulate expression of PTP1B mRNA by at least 10%, by at least 20%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100%.

The compounds of the present inventions are inhibitors of PTP1B expression. Thus, the compounds of the present invention are believed to be useful for treating metabolic diseases and conditions, particularly diabetes, obesity, hyperlipidemia or metabolic syndrome X. The compounds of the invention are also believed to be useful for preventing or delaying the onset of metabolic diseases and conditions, particularly diabetes, obesity, hyperlipidemia or metabolic syndrome X. Metabolic syndrome, metabolic syndrome X or simply Syndrome X refers to a cluster of risk factors that include obesity, dyslipidemia, particularly high blood triglycerides, glucose intolerance, high blood sugar and high blood pressure (Scott, C. L., *Am. J. Cardiol.* 2003 Jul. 3; 92(1A): 35i-42i). Antisense inhibitors of PTP1B have surprisingly been found to be effective for lowering blood glucose, including plasma glucose, and for lowering blood lipids, including serum lipids, particularly serum cholesterol and serum triglycerides. The compounds of the invention are therefore particularly useful in medicaments for the treatment, prevention and delay of onset of type 2 diabetes, high blood glucose and hyperlipidemia.

It is understood in the art that the sequence of an antisense compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). It is preferred that the antisense compounds of the present invention comprise at least 70%, or at least 75%, or at least 80%, or at least 85% sequence complementarity to a target region within the target nucleic acid, more preferably that they comprise at least 90% sequence complementarity and even more preferably comprise at least 95% or at least 99% sequence complementarity to the target region within the target nucleic acid sequence to which they are targeted. For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention.

Percent complementarity of an antisense compound with a region of a target nucleic acid can be determined routinely using BLAST programs (basic local alignment search tools) and PowerBLAST programs known in the art (Altschul et al., *J. Mol. Biol.,* 1990, 215, 403-410; Zhang and Madden, *Genome Res.,* 1997, 7, 649-656).

Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (*Adv. Appl. Math.,* 1981, 2, 482-489). In some preferred embodiments, homology, sequence identity or complementarity, between the oligomeric and target is between about 50% to about 60%. In some embodiments, homology, sequence identity or complementarity, is between about 60% to about 70%. In preferred embodiments, homology, sequence identity or complementarity, is between about 70% and about 80%. In more preferred embodiments, homology, sequence identity or complementarity, is between about 80% and about 90%. In some preferred embodiments, homology, sequence identity or complementarity, is about 90%, about 92%, about 94%, about 95%, about 96%, about 97%, about 98%, about 99% or about 100%.

According to the present invention, compounds include antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these compounds may be introduced in the form of single-stranded, double-stranded, circular or hairpin oligomeric compounds and may contain structural elements such as internal or terminal bulges or loops. Once introduced to a system, the compounds of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While a suitable form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, *Caenorhabditis elegans* (Guo and Kempheus, *Cell,* 1995, 81, 611-620). Montgomery et al. have shown that the primary interference effects of dsRNA are posttranscriptional (Montgomery et al., *Proc. Natl. Acad. Sci. USA,* 1998, 95, 15502-15507). The posttranscriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., *Nature*, 1998, 391, 806-811). Recently, it has been shown that it is, in fact, the single-stranded RNA oligomers of antisense polarity of the dsRNAs which are the potent inducers of RNAi (Tijsterman et al., *Science*, 2002, 295, 694-697).

The antisense compounds of the present invention also include modified compounds in which a different base is present at one or more of the nucleotide positions in the compound. For example, if the first nucleotide is an adenosine, modified compounds may be produced which contain thymidine, guanosine or cytidine at this position. This may be done at any of the positions of the antisense compound.

The antisense compounds of the present invention can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway. Antisense modulation has, therefore, been harnessed for research use.

For use in kits and diagnostics, the compounds of the present invention, either alone or in combination with other compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today*, 2000, 5, 415-425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. U.S.A.*, 2000, 97, 1976-81), protein arrays and proteomics (Celis, et al., *FEBS Lett.*, 2000, 480, 2-16; Jungblut, et al., *Electrophoresis*, 1999, 20, 2100-10), expressed sequence tag (EST) sequencing (Celis, et al., *FEBS Lett.*, 2000, 480, 2-16; Larsson, et al., *J. Biotechnol.*, 2000, 80, 143-57), subtractive RNA fingerprinting (SuRF) (Fuchs, et al., *Anal. Biochem.*, 2000, 286, 91-98; Larson, et al., *Cytometry*, 2000, 41, 203-208), subtractive cloning, differential display (DD) (Jurecic and Belmont, *Curr. Opin. Microbiol.*, 2000, 3, 316-21), comparative genomic hybridization (Carulli, et al., *J. Cell Biochem. Suppl.*, 1998, 31, 286-96), FISH (fluorescent in situ hybridization) techniques (Going and Gusterson, *Eur. J. Cancer*, 1999, 35, 1895-904) and mass spectrometry methods (To, *Comb. Chem. High Throughput Screen*, 2000, 3, 235-41).

The antisense compounds of the invention are useful for research and diagnostics, because these compounds hybridize to nucleic acids encoding PTP1B. For example, oligonucleotides that are shown to hybridize with such efficiency and under such conditions as disclosed herein as to be effective PTP1B inhibitors are effective primers or probes under conditions favoring gene amplification or detection, respectively. These primers and probes are useful in methods requiring the specific detection of nucleic acid molecules encoding PTP1B and in the amplification of said nucleic acid molecules for detection or for use in further studies of PTP1B.

Hybridization of the antisense oligonucleotides, particularly the primers and probes, of the invention with a nucleic acid encoding PTP1B can be detected by means known in the art. Such means may include conjugation of an enzyme to the oligonucleotide, radiolabelling of the oligonucleotide or any other suitable detection means. Kits using such detection means for detecting the level of PTP1B in a sample may also be prepared.

The specificity and sensitivity of antisense are also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 50 nucleobases (i.e. from about 8 to about 50 linked nucleosides). One having ordinary skill in the art will appreciate that this embodies compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length.

In another embodiment, the antisense compounds of the invention are 15 to 30 nucleobases in length. One having ordinary skill in the art will appreciate that this embodies compounds of 15, 16, 17, 18, 19, 20, 21, 22, 23, 24, 25, 26, 27, 28, 29, or 30 nucleobases in length.

Antisense compounds 8-50 nucleobases in length comprising a stretch of at least eight (8) consecutive nucleobases selected from within the illustrative antisense compounds are considered to be suitable antisense compounds as well. Exemplary preferred antisense compounds include oligonucleotide sequences that comprise at least the 8 consecutive nucleobases from the 5'-terminus of one of the illustrative preferred antisense compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains about 8 to about 50 nucleobases). Similarly preferred antisense compounds are represented by oligonucleotide sequences that comprise at least the 8 consecutive nucleobases from the 3'-terminus of one of the illustrative preferred antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about 8 to about 50 nucleobases). It is also understood that preferred antisense compounds may be represented by oligonucleotide sequences that comprise at least 8 consecutive nucleobases from an internal portion of the sequence of an illustrative preferred antisense compound, and may extend in either or both directions until the oligonucleotide contains about 8 to about 50 nucleobases. One having skill in the art armed with the preferred antisense compounds illustrated herein will be able, without undue experimentation, to identify further preferred antisense compounds.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*, 1991, 254, 1497-1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— ((known as a methylene (methylimino) or MMI backbone)), —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester backbone is represented as —O—P—O—$CH_2$—) of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[$(CH_2)_n$O]$_m$$CH_3$, O$(CH_2)_n$O$CH_3$, O$(CH_2)_n$$NH_2$, O$(CH_2)_n$$CH_3$, O$(CH_2)_n$O$NH_2$, and O$(CH_2)_n$ON[$(CH_2)_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78, 486-504) i.e., an alkoxyalkoxy group.

A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2$—O—$CH_2$—$N(CH_2)_2$, also described in examples hereinbelow.

Other preferred modifications include 2'-methoxy (2'-O—$CH_3$), 2'-aminopropoxy (2'-$OCH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2 C (Sanghvi, Y. S., Crooke, S. T. and Lebleu, B., eds., *Antisense Research and Applications*, CRC Press, Boca Raton, 1993, pp. 276-278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA*, 1989, 86, 6553-6556), cholic acid (Manoharan et al., *Bioorg. Med. Chem. Let.*, 1994, 4, 1053-1060), a thioether, e.g., hexyl-5-tritylthiol (Manoharan et al., *Ann. N.Y. Acad. Sci.*, 1992, 660, 306-309; Manoharan et al., *Bioorg. Med. Chem. Let.*, 1993, 3, 2765-2770), a thiocholesterol (Oberhauser et al., *Nucl. Acids Res.*, 1992, 20, 533-538), an aliphatic chain, e.g., dodecandiol or undecyl residues (Saison-Behmoaras et al., *EMBO J.*, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid (Manoharan et al., *Tetrahedron Lett.*, 1995, 36, 3651-3654), a palmityl moiety (Mishra et al., *Biochim. Biophys. Acta*, 1995, 1264, 229-237), or an octadecylamine or hexylamino-carbonyl-oxycholesterol moiety (Crooke et al., *J. Pharmacol. Exp. Ther.*, 1996, 277, 923-937).

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules.

The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1-19). The base addition salts of said acidic compounds are prepared by contacting the free acid form with a sufficient amount of the desired base to produce the salt in the conventional manner. The free acid form may be regenerated by contacting the salt form with an acid, and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfoc acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder, which can be treated by modulating the expression of PTP1B, is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding PTP1B, enabling sandwich and other assays to easily be constructed to exploit this fact. Hybridization of the antisense oligonucleotides of the invention with a nucleic acid encoding PTP1B can be detected by means known in the art. Such means may include conjugation of an enzyme to the oligonucleotide, radiolabelling of the oligonucleotide or any other suitable detection means. Kits using such detection means for detecting the level of PTP1B in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 m in diameter. (Idson, in *Pharmaceutical Dosage Forms*, Lieberman, Rieger and Banker (Eds.), 1988, Marcel Dekker, Inc., New York, N.Y., volume 1, p. 199; Rosoff, in *Pharmaceutical Dosage Forms*, Lieberman, Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et al., in *Remington's Pharmaceutical Sci-*

*ences*, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms*, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms*, Lieberman, Rieger and Banker (Eds.), 1988, Marcel Dekker, Inc., New York, N.Y., volume 1, p. 285; Idson, in *Pharmaceutical Dosage Forms*, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms*, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, in *Pharmaceutical Dosage Forms*, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms*, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms*, Lieberman, Rieger and Banker (Eds.), 1988, Marcel Dekker, Inc., New York, N.Y., volume 1, p. 245; Idson, in *Pharmaceutical Dosage Forms*, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms*, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems*, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385-1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research*, 1994, 11, 1385; Ho et al., *J. Pharm. Sci.*, 1996, 85, 138-143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms*, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980-985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 1992, 19, 269-274).

One major type of liposomal composition includes phospholipids other than naturally-derived phosphatidyl-choline. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanol-amine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting*, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., *Antiviral Research*, 1992, 18, 259-265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P.Pharma. Sci.*, 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765). Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.*, 1980, 53, 2778) described liposomes comprising a nonionic detergent, $2C_{12}15G$, that contains a PEG moiety. Ilium et al. (*FEBS Lett.*, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.*, 1990, 268, 235) described experiments demonstrating that liposomes comprising phosphatidyl-ethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. No. 5,540,935 (Miyazaki et al.) and U.S. Pat. No. 5,556, 948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxy-nucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms*, Marcel Dekker, Inc., New York, N.Y., 1988, p. 285).

Penetration Enhancers

In one embodiment, the present invention employs various penetration enhancers to accomplish the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems*, 1991, p. 92). Each of the above mentioned classes of penetration enhancers are described below in greater detail.

Surfactants

In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems*, 1991, p. 92); and perfluorochemical emulsions, such as FC-43. Takahashi et al., *J. Pharm. Pharmacol.*, 1988, 40, 252).

Fatty Acids

Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems*, 1991, p. 92; Muranishi, *Critical Reviews in Therapeutic Drug Carrier Systems*, 1990, 7, 1-33; El Hariri et al., *J. Pharm. Pharmacol.*, 1992, 44, 651-654).

Bile Salts

The physiological role of bile includes the facilitation of dispersion and absorption of lipids and fat-soluble vitamins (Brunton, Chapter 38 in: Goodman & Gilman's *The Pharmacological Basis of Therapeutics*, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxy-cholate), chenodeoxycholic acid (sodium chenodeoxy-cholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems*, 1991, page 92; Swinyard, Chapter 39 In: *Remington's Pharmaceutical Sciences*, 18th Ed., Gennaro, ed., Mack Publishing Co., Easton, Pa., 1990, pages 782-783; Muranishi, *Critical Reviews in Therapeutic Drug Carrier Systems*, 1990, 7, 1-33; Yamamoto et al., *J. Pharm. Exp. Ther.*, 1992, 263, 25; Yamashita et al., *J. Pharm. Sci.*, 1990, 79, 579-583).

Chelating Agents

Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.*, 1993, 618, 315-339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems*, 1991, page 92; Muranishi, *Critical Reviews in Therapeutic Drug Carrier Systems*, 1990, 7, 1-33; Buur et al., *J. Control Rel.*, 1990, 14, 43-51).

Non-Chelating Non-Surfactants

As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems*, 1990, 7, 1-33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems*, 1991, page 92); and non-steroidal anti-inflammatory agents such as diclofenac sodium, indomethacin and phenylbutazone (Yamashita et al., *J. Pharm. Pharmacol.*, 1987, 39, 621-626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.*, 1995, 5, 115-121; Takakura et al., *Antisense & Nucl. Acid Drug Dev.*, 1996, 6, 177-183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). See, generally, *The Merck Manual of Diagnosis and Therapy*, 15th Ed., Berkow et al., eds., 1987, Rahway, N.J., pages 1206-1228). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy*, 15th Ed., Berkow et al., eds., 1987, Rahway, N.J., pages 2499-2506 and 46-49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis Deoxy and 2'-alkoxy amidites 2'-Deoxy and 2'-methoxy beta-cyanoethyldiisopropyl phosphoramidites were purchased from commercial sources (e.g. Chemgenes, Needham, Mass. or Glen Research, Inc., Sterling, Va.). Other 2'-O-alkoxy substituted nucleoside amidites are prepared as described in U.S. Pat. No. 5,506,351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides were synthesized according to published methods [Sanghvi, et. al., *Nucleic Acids Research*, 1993, 21, 3197-3203] using commercially available phosphoramidites (Glen Research, Sterling, Va., or ChemGenes, Needham, Mass.).

2'-Fluoro amidites

2'-Fluorodeoxyadenosine amidites

2'-fluoro oligonucleotides were synthesized as described previously [Kawasaki, et. al., *J. Med. Chem.*, 1993, 36, 831-841] and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyrylarabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3' phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3' phosphoramidites.

2'-O-(2-Methoxyethyl) modified amidites

2'-O-Methoxyethyl-substituted nucleoside amidites are prepared as follows, or alternatively, as per the methods of Martin, P., *Helvetica Chimica Acta*, 1995, 78, 486-504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10-25%) to give a white solid, mp 222-4° C.).

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155-16 C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/hexane/acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MeOH. Upon completion of the reaction, as judged by TLC, MeOH (50 mL) was added and the mixture evaporated at 35 C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/hexane (4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0-10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl,

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and NH$_4$OH (30 mL) was stirred at room temperature for 2 hours. The dioxane solution was evaporated and the residue azeotroped with MeOH (2×200 mL). The residue was dissolved in MeOH (300 mL) and transferred to a 2 L stainless steel pressure vessel. MeOH (400 mL) saturated with NH$_3$ gas was added and the vessel heated to 100° C. for 2 hours (TLC showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/hexane (1:1) containing 0.5% Et$_3$NH as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite N4-Benzoyl-2'-O-methoxyethyl-5'-O-dimethoxytrityl-5-methylcytidine (74 g, 0.10 M) was dissolved in CH$_2$Cl$_2$ (1 L). Tetrazole diisopropylamine (7.1 g) and 2-cyanoethoxy-tetra (isopropyl)-phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc/hexane (3:1) as the eluting solvent. The pure fractions were combined to give 90.6 g (87%) of the title compound.

2'-O-(Aminooxyethyl) nucleoside amidites and 2'-O-(dimethylaminooxyethyl) nucleoside amidites

2'-(Dimethylaminooxyethoxy) nucleoside amidites

2'-(Dimethylaminooxyethoxy) nucleoside amidites (also known in the art as 2'-O -(dimethylaminooxyethyl) nucleoside amidites) are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-O$^2$-2'-anhydro-5-methyluridine

O$^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-O$^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure<100 psig). The reaction vessel was cooled to ambient and opened. TLC(Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40-100° C.) with the more extreme conditions used to remove the ethylene glycol. Alternatively, once the low boiling solvent is gone, the remaining solution can be partitioned between ethyl acetate and water. The product will be in the organic phase. The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthaliamidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over P$_2$O$_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenyl-silyl-5-methyluridine as white foam (21.819 g, 86%).

5'-O-tert-butyldiphenylsilyl-2'-O-[(2-formadoximinooxy)ethyl]-5-methyluridine 2'-O-([2-phthalimidoxy)ethyl]-5'-t-butyldiphenyl-silyl-5-methyluridine (3.1 g, 4.5 mmol) was dissolved in dry $CH_2Cl_2$ 4.5 mL) and methylhydrazine (300 mL, 4.64 mmol) was added dropwise at –10° C. to 0° C. After 1 h the mixture was filtered, the filtrate was washed with ice cold $CH_2Cl_2$ and the combined organic phase was washed with water, brine and dried over anhydrous $Na_2SO_4$. The solution was concentrated to get 2'-O-(aminooxyethyl)thymidine, which was then dissolved in MeOH (67.5 mL). To this formaldehyde (20% aqueous solution, w/w, 1.1 eq.) was added and the resulting mixture was stirred for 1 h. Solvent was removed under vacuum; residue chromatographed to get 5'-O-tert-butyldiphenylsilyl-2'-O-[(2-formadoximi-nooxy)ethyl]-5-methyluridine as white foam (1.95 g, 78%).

5'-O-tert-Butyldiphenylsilyl-2'-O—[N,N-dimethylaminooxyethyl]-5-methyluridine 5'-O-tert-butyldiphenylsilyl-2'-O-[(2-formadoximinooxy)ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10 C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness. The residue obtained was purified by flash column chromatography and eluted with 5% MeOH in $CH_2Cl_2$ to get 5'-O-tert-butyldiphenylsilyl-2'-O—[N,N-dimethylamino-oxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O—[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,$N^1$,$N^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL). Ethyl acetate layer was dried over anhydrous $Na_2SO_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy) nucleoside amidites

2'-(Aminooxyethoxy) nucleoside amidites (also known in the art as 2'-O-(aminooxyethyl) nucleoside amidites) are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl)diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (PCT Publication WO 94/02501). Standard protection procedures should afford 2'-O-(2-ethylacetyl)-5'-O-(4,4'-dimethoxy-trityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O- diphenylcarbamoyl-2'-O-(2-ethylacetyl)-5'-O-(4,4'-dimethoxytrityl)guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite].

2'-dimethylaminoethoxyethoxy (2'-DMAEOE) nucleoside amidites

2'-dimethylaminoethoxyethoxy nucleoside amidites (also known in the art as 2'-O- dimethylaminoethoxyethyl, i.e., 2'-O—$CH_2$—O—$CH_2$—$N(CH_2)_2$, or 2'-DMAEOE nucleoside amidites) are prepared as follows. Other nucleoside amidites are prepared similarly.

2'-O-[2(2-N,N-dimethylaminoethoxy)ethyl]-5-methyl uridine

2[2-(Dimethylamino)ethoxy]ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. $O^2$-,2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-dimethoxytrityl-2'-O-[2(2-N,N-dimethylaminoethoxy)ethyl)]-5-methyl uridine

To 0.5 g (1.3 mmol) of 2'-O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with $CH_2Cl_2$ (2×200 mL). The combined $CH_2Cl_2$ layers are washed with saturated $NaHCO_3$ solution, followed by saturated NaCl solution and dried over anhydrous sodium sulfate. Evaporation of the solvent followed by silica gel chromatography using MeOH:$CH_2Cl_2$:$Et_3N$ (20:1, v/v, with 1% triethylamine) gives the title compound.

5'-O-Dimethoxytrityl-2'-O-[2(2-N,N-dimethylaminoethoxy)ethyl)]-5-methyl uridine-3'-O-(cyanoethyl-N, N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-dimethylamino-ethoxy)ethyl)]-5-methyluridine (2.17 g, 3 mmol) dissolved in $CH_2Cl_2$ (20 mL) under an atmosphere of argon. The reaction mixture is stirred overnight and the solvent evaporated. The resulting residue is purified by silica gel flash column chromatography with ethyl acetate as the eluent to give the title compound.

Example 2

Oligonucleotide Synthesis

Unsubstituted and substituted phosphodiester (P═O) oligonucleotides are synthesized on an automated DNA synthesizer (Applied Biosystems model 380B) using standard phosphoramidite chemistry with oxidation by iodine.

Phosphorothioates (P═S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55 C. (18 h), the oligonucleotides were purified by precipitating twice with 2.5 volumes of ethanol from a 0.5 M NaCl solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. No. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3

Oligonucleoside Synthesis

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P═O or P═S linkages are prepared as described in U.S. Pat. Nos. 5,378,825; 5,386,023; 5,489,677; 5,602,240; and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry,* 1996, 4, 5-23. They may also be prepared in accordance with U.S. Pat. Nos. 5,539,082; 5,700,922; and 5,719,262, herein incorporated by reference.

Example 5

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me]Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]-[2'-deoxy]-[2'-O-(Methoxyethyl)]Chimeric Phosphorothioate Oligonucleotides

[2'-O-(2-methoxyethyl)]-[2'-deoxy]-[-2'-O-(methoxyethyl)]chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl)Phosphodiester]Chimeric Oligonucleotides

[2'-O-(2-methoxyethyl phosphodiester]-[2'-deoxy phosphorothioate]-[2'-O-(methoxyethyl)phosphodiester]chimeric oligonucleotides are prepared as per the above procedure for the 2'-O-methyl chimeric oligonucleotide with the substitution of 2'-O-(methoxyethyl)amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6

Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}P$ nuclear magnetic resonance spectroscopy, and for some studies oligonucleotides were purified by HPLC, as described by Chiang et al., *J. Biol. Chem.* 1991, 266, 18162-18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated $NH_4OH$ at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 8

Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACE™ MDQ instrument) or, for individually prepared samples, on a commercial CE apparatus (e.g., Beckman P/ACE™ 5000 instrument, ABI 270 instrument). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following 5 cell types are provided for illustrative purposes, but other cell types can be routinely used, provided that the target is expressed in the cell type chosen. This can be readily determined by methods routine in the art, for example Northern blot analysis, Ribonuclease protection assays, or RT-PCR.

T-24 Cells

The human transitional cell bladder carcinoma cell line T-24 was obtained from the American Type Culture Collection (ATCC) (Manassas, Va.). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 µg/mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells

The human lung carcinoma cell line A549 was obtained from the American Type Culture Collection (ATCC) (Manassas, Va.). A549 cells were routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 µg/mL (Gibco/Life Technologies, Gaithersburg, Md.). Cells were routinely passaged by trypsinization and dilution when they reached 90% confluence.

NHDF Cells

Human neonatal dermal fibroblast (NHDF) were obtained from the Clonetics Corporation (Walkersville Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells

Human embryonic keratinocytes (HEK) were obtained from the Clonetics Corporation (Walkersville, Md.). HEKs were routinely maintained in Keratinocyte Growth Medium (Clonetics Corporation, Walkersville Md.) formulated as recommended by the supplier. Cells were routinely maintained for up to 10 passages as recommended by the supplier.

PC-12 Cells

The rat neuronal cell line PC-12 was obtained from the American Type Culture Collection (Manassas, Va.). PC-12 cells were routinely cultured in DMEM, high glucose (Gibco/Life Technologies, Gaithersburg, Md.) supplemented with 10% horse serum+5% fetal calf serum (Gibco/Life Technologies, Gaithersburg, Md.). Cells were routinely passaged by trypsinization and dilution when they reached 90% confluence. Cells were seeded into 96-well plates (Falcon-Primaria #3872) at a density of 20000 cells/well for use in RT-PCR analysis.

For Northern blotting or other analysis, cells may be seeded onto 100 mm or other standard tissue culture plates and treated similarly, using appropriate volumes of medium and oligonucleotide.

Treatment with Antisense Compounds

When cells reached 80% confluency, they were treated with oligonucleotide. For cells grown in 96-well plates, wells were washed once with 200 µl, OPTI-MEM™-1 reduced-serum medium (Gibco BRL) and then treated with 130 µl of OPTI-MEM™-1 medium containing 3.75 µg/mL LIPOFECTIN™ reagent (Gibco BRL) and the desired concentration of oligonucleotide. After 4-7 hours of treatment, the medium was replaced with fresh medium. Cells were harvested 16-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 10

Analysis of Oligonucleotide Inhibition of PTP1B Expression

Antisense modulation of PTP1B expression can be assayed in a variety of ways known in the art. For example, PTP1B mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. Methods of RNA isolation are taught in, for example, Ausubel, F. M. et al., Current Protocols in Molecular Biology, Volume 1, pp. 4.1.1-4.2.9 and 4.5.1-4.5.3, John Wiley & Sons, Inc., 1993. Northern blot analysis is routine in the art and is taught in, for example, Ausubel, F. M. et al., Current Protocols in Molecular Biology, Volume 1, pp. 4.2.1-4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions. Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed as multiplexable. Other methods of PCR are also known in the art.

Protein levels of PTP1B can be quantitated in a variety of ways well known in the art, such as immunoprecipitation, Western blot analysis (immunoblotting), ELISA or fluorescence-activated cell sorting (FACS). Antibodies directed to PTP1B can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., Current Protocols in Molecular Biology, Volume 2, pp. 11.12.1-11.12.9, John Wiley & Sons, Inc., 1997. Preparation of monoclonal antibodies is taught in, for example, Ausubel, F. M. et al., Current Protocols in Molecular Biology, Volume 2, pp. 11.4.1-11.11.5, John Wiley & Sons, Inc., 1997.

Immunoprecipitation methods are standard in the art and can be found at, for example, Ausubel, F. M. et al., Current Protocols in Molecular Biology, Volume 2, pp. 10.16.1-10.16.11, John Wiley & Sons, Inc., 1998. Western blot (immunoblot) analysis is standard in the art and can be found at, for example, Ausubel, F. M. et al., Current Protocols in Molecular Biology, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., Current Protocols in Molecular Biology, Volume 2, pp. 11.2.1-11.2.22, John Wiley & Sons, Inc., 1991.

Example 11

Poly(A)+ mRNA Isolation

Poly(A)+ mRNA was isolated according to Miura et al., Clin. Chem., 1996, 42, 1758-1764. Other methods for poly (A)+ mRNA isolation are taught in, for example, Ausubel, F. M. et al., Current Protocols in Molecular Biology, Volume 1, pp. 4.5.1-4.5.3, John Wiley & Sons, Inc., 1993. Briefly, for cells grown on 96-well plates, growth medium was removed from the cells and each well was washed with 200 µL cold PBS. Sixty µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. Fifty-five µL of lysate was transferred to Oligo d(T) coated 96-well plates (AGCT Inc., Irvine Calif.). Plates were incubated for 60 minutes at room temperature, washed 3 times with 200 µl of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12

Total RNA Isolation

Total mRNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 µL cold PBS. One hundred µL Buffer RLT was added to each well and the plate vigorously agitated for 20 seconds. One hundred µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 15 seconds. One mL of Buffer RW1 was added to each well of the RNEASY 96™ plate and the vacuum again applied for 15 seconds. One mL of Buffer RPE was then added to each well of the RNEASY 96™ plate and the vacuum applied for a period of 15 seconds. The Buffer RPE wash was then repeated and the vacuum was applied for an additional 10 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 60 µL, water into each well, incubating 1 minute, and then applying the vacuum for 30 seconds. The elution step was repeated with an additional 60 µL water.

The repetitive pipetting and elution steps may be automated using a QIAGEN Bio-Robot 9604 apparatus (Qiagen, Inc., Valencia, Calif.). Essentially, after lysing of the cells on the culture plate, the plate is transferred to the robot deck where the pipetting, DNase treatment and elution steps are carried out.

Example 13

Real-Time Quantitative PCR Analysis of PTP1B mRNA Levels

Quantitation of PTP1B mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE, FAM, or VIC, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

PCR reagents were obtained from PE-Applied Biosystems, Foster City, Calif. RT-PCR reactions were carried out by adding 25 µL PCR cocktail (1× TAQMAN™ buffer A, 5.5 mM $MgCl_2$, 300 µM each of dATP, dCTP and dGTP, 600 µM of dUTP, 100 nM each of forward primer, reverse primer, and probe, 20 Units RNAse inhibitor, 1.25 Units AMPLITAQ GOLD™ reagent, and 12.5 Units MuLV reverse transcriptase) to 96 well plates containing 25 µL poly(A) mRNA solution. The RT reaction was carried out by incubation for 30 minutes at 48° C. Following a 10 minute incubation at 95° C. to activate the AMPLITAQ GOLD™ reagent, 40 cycles of a two-step PCR protocol were carried out: 95° C. for 15 seconds (denaturation) followed by 60° C. for 1.5 minutes (annealing/extension).

Probes and primers to human PTP1B were designed to hybridize to a human PTP1B sequence, using published sequence information (GenBank accession number M31724, incorporated herein as SEQ ID NO:3). For human PTP1B the PCR primers were:
forward primer: GGAGTTCGAGCAGATCGACAA (SEQ ID NO: 4)
reverse primer: GGCCACTCTACATGGGAAGTC (SEQ ID NO: 5) and the PCR probe was: FAM-AGCTGGGCGGC-CATTTACCAGGAT-TAMRA
(SEQ ID NO: 6) where FAM (PE-Applied Biosystems, Foster City, Calif.) is the fluorescent reporter dye) and TAMRA (PE-Applied Biosystems, Foster City, Calif.) is the quencher dye. For human GAPDH the PCR primers were:
forward primer: GAAGGTGAAGGTCGGAGTC (SEQ ID NO: 7)
reverse primer: GAAGATGGTGATGGGATTTC (SEQ ID NO: 8) and the PCR probe was: 5' JOE-CAAGCTTCCCGT-TCTCAGCC-TAMRA 3' (SEQ ID NO: 9) where JOE (PE-Applied Biosystems, Foster City, Calif.) is the fluorescent reporter dye) and TAMRA (PE-Applied Biosystems, Foster City, Calif.) is the quencher dye.

Probes and primers to rat PTP1B were designed to hybridize to a rat PTP1B sequence, using published sequence information (GenBank accession number M33962, incorporated herein as SEQ ID NO:10). For rat PTP1B the PCR primers were:
forward primer: CGAGGGTGCAAAGTTCATCAT (SEQ ID NO:11)
reverse primer: CCAGGTCTTCATGGGAAAGCT (SEQ ID NO: 12) and the PCR probe was: FAM-CGACTCGTCAGT-GCAGGATCAGTGGA-TAMRA
(SEQ ID NO: 13) where FAM (PE-Applied Biosystems, Foster City, Calif.) is the fluorescent reporter dye) and TAMRA (PE-Applied Biosystems, Foster City, Calif.) is the quencher dye. For rat GAPDH the PCR primers were:
forward primer: TGTTCTAGAGACAGCCGCATCTT (SEQ ID NO: 14)
reverse primer: CACCGACCTTCACCATCTTGT (SEQ ID NO: 15) and the PCR probe was: 5'JOE-TTGTGCAGTGC-CAGCCTCGTCTCA-TAMRA 3' (SEQ ID NO: 16) where JOE (PE-Applied Biosystems, Foster City, Calif.) is the fluorescent reporter dye) and TAMRA (PE-Applied Biosystems, Foster City, Calif.) is the quencher dye.

Example 14

Northern Blot Analysis of PTP1B mRNA Levels

Eighteen hours after antisense treatment, cell monolayers were washed twice with cold PBS and lysed in 1 mL RNA-ZOL™ reagent (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 instrument (Stratagene, Inc, La Jolla, Calif.) and then robed using QUICKHYB™ hybridization solution (Stratagene, La Jolla, Calif.) using manufacturer's recommendations for stringent conditions.

To detect human PTP1B, a human PTP1B specific probe was prepared by PCR using the forward primer GGAGTTC-GAGCAGATCGACAA (SEQ ID NO: 4) and the reverse primer GGCCACTCTACATGGGAAGTC (SEQ ID NO: 5). To normalize for variations in loading and transfer efficiency membranes were stripped and probed for human glyceraldehyde-3-phosphate dehydrogenase (GAPDH) RNA (Clontech, Palo Alto, Calif.).

To detect rat PTP1B, a rat PTP1B specific probe was prepared by PCR using the forward primer CGAGGGTG- CAAAGTTCATCAT (SEQ ID NO:11) and the reverse primer CCAGGTCTTCATGGGAAAGCT (SEQ ID NO: 12). To normalize for variations in loading and transfer efficiency membranes were stripped and probed for rat glyceraldehyde-3-phosphate dehydrogenase (GAPDH) RNA (Clontech, Palo Alto, Calif.).

Hybridized membranes were visualized and quantitated using a PHOSPHORIMAGER™ instrument and IMAGEQUANT™ Software V3.3 (Molecular Dynamics, Sunnyvale, Calif.). Data was normalized to GAPDH levels in untreated controls.

Example 15

Antisense Inhibition of Human PTP1B Expression by Chimeric Phosphorothioate Oligonucleotides Having 2'-MOE Wings and a Deoxy Gap In accordance with the present invention, a series of oligonucleotides were designed to target different regions of the human PTP1B RNA, using published sequences (GenBank accession number M31724, incorporated herein as SEQ ID NO: 3). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (T-MOE) nucleotides. The internucleoside (backbone) linkages are phosphorothioate (P=S) throughout the oligonucleotide. All cytidine residues are 5-methylcytidines. The compounds were analyzed for their effect on human PTP1B mRNA levels by quantitative real-time PCR as described in other examples herein. Data are averages from two experiments. If present, "N.D." indicates "no data".

TABLE 1

Inhibition of human PTP1B mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 107769 | 5' UTR | 3 | 1 | cttagccccgaggcccgccc | 0 | 17 |
| 107770 | 5' UTR | 3 | 41 | ctcggcccactgcgccgtct | 58 | 18 |
| 107771 | Start Codon | 3 | 74 | catgacgggccagggcggct | 60 | 19 |
| 107772 | Coding | 3 | 113 | cccggacttgtcgatctgct | 95 | 20 |
| 107773 | Coding | 3 | 154 | ctggcttcatgtcggatatc | 88 | 21 |
| 107774 | Coding | 3 | 178 | ttggccactctacatgggaa | 77 | 22 |
| 107775 | Coding | 3 | 223 | ggactgacgtctctgtacct | 75 | 23 |
| 107776 | Coding | 3 | 252 | gatgtagtttaatccgacta | 82 | 24 |
| 107777 | Coding | 3 | 280 | ctagcgttgatatagtcatt | 29 | 25 |
| 107778 | Coding | 3 | 324 | gggtaagaatgtaactcctt | 86 | 26 |
| 107779 | Coding | 3 | 352 | tgaccgcatgtgttaggcaa | 75 | 27 |
| 107780 | Coding | 3 | 381 | ttttctgctcccacaccatc | 30 | 28 |
| 107781 | Coding | 3 | 408 | ctctgttgagcatgacgaca | 78 | 29 |
| 107782 | Coding | 3 | 436 | gcgcattttaacgaacccttt | 83 | 30 |
| 107783 | Coding | 3 | 490 | aaatttgtgtcttcaaagat | 0 | 31 |
| 107784 | Coding | 3 | 519 | tgatatcttcagagatcaat | 57 | 32 |
| 107785 | Coding | 3 | 547 | tctagctgtcgcactgtata | 74 | 33 |
| 107786 | Coding | 3 | 575 | agtttcttggttgtaaggt | 33 | 34 |
| 107787 | Coding | 3 | 604 | gtggtatagtggaaatgtaa | 51 | 35 |
| 107788 | Coding | 3 | 632 | tgattcagggactccaaagt | 55 | 36 |
| 107789 | Coding | 3 | 661 | ttgaaaagaaagttcaagaa | 17 | 37 |
| 107790 | Coding | 3 | 688 | gggctgagtgaccctgactc | 61 | 38 |
| 107791 | Coding | 3 | 716 | gcagtgcaccacaacgggcc | 81 | 39 |
| 107792 | Coding | 3 | 744 | aggttccagacctgccgatg | 81 | 40 |

TABLE 1-continued

Inhibition of human PTP1B mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 107793 | Coding | 3 | 772 | agcaggaggcaggtatcagc | 2 | 41 |
| 107794 | Coding | 3 | 799 | gaagaagggtctttcctctt | 53 | 42 |
| 107795 | Coding | 3 | 826 | tctaacagcactttcttgat | 18 | 43 |
| 107796 | Coding | 3 | 853 | atcaacccatccgaaactt | 0 | 44 |
| 107797 | Coding | 3 | 880 | gagaagcgcagctggtcggc | 82 | 45 |
| 107798 | Coding | 3 | 908 | tttggcaccttcgatcacag | 62 | 46 |
| 107799 | Coding | 3 | 952 | agctccttccactgatcctg | 70 | 47 |
| 107800 | Coding | 3 | 1024 | tccaggattcgtttgggtgg | 72 | 48 |
| 107801 | Coding | 3 | 1052 | gaactccctgcatttcccat | 68 | 49 |
| 107802 | Coding | 3 | 1079 | ttccttcacccactggtgat | 40 | 50 |
| 107803 | Coding | 3 | 1148 | gtagggtgcggcatttaagg | 0 | 51 |
| 107804 | Coding | 3 | 1176 | cagtgtcttgactcatgctt | 75 | 52 |
| 107805 | Coding | 3 | 1222 | gcctgggcacctcgaagact | 67 | 53 |
| 107806 | Coding | 3 | 1268 | ctcgtccttctcgggcagtg | 37 | 54 |
| 107807 | Coding | 3 | 1295 | gggcttccagtaactcagtg | 73 | 55 |
| 107808 | Coding | 3 | 1323 | ccgtagccacgcacatgttg | 80 | 56 |
| 107809 | Coding | 3 | 1351 | tagcagaggtaagcgccggc | 72 | 57 |
| 107810 | Stop Codon | 3 | 1379 | ctatgtgttgctgttgaaca | 85 | 58 |
| 107811 | 3' UTR | 3 | 1404 | ggaggtggagtggaggaggg | 51 | 59 |
| 107812 | 3' UTR | 3 | 1433 | ggctctgcgggcagaggcgg | 81 | 60 |
| 107813 | 3' UTR | 3 | 1460 | ccgcggcatgcctgctagtc | 84 | 61 |
| 107814 | 3' UTR | 3 | 1489 | tctctacgcggtccggcggc | 84 | 62 |
| 107815 | 3' UTR | 3 | 1533 | aagatgggttttagtgcaga | 65 | 63 |
| 107816 | 3' UTR | 3 | 1634 | gtactctctttcactctcct | 69 | 64 |
| 107817 | 3' UTR | 3 | 1662 | ggccccttccctctgcgccg | 59 | 65 |
| 107818 | 3' UTR | 3 | 1707 | ctccaggagggagccctggg | 57 | 66 |
| 107819 | 3' UTR | 3 | 1735 | gggctgttggcgtgcgccgc | 54 | 67 |
| 107820 | 3' UTR | 3 | 1783 | tttaaataaatatggagtgg | 0 | 68 |
| 107821 | 3' UTR | 3 | 1831 | gttcaagaaaatgctagtgc | 69 | 69 |
| 107822 | 3' UTR | 3 | 1884 | ttgataaagcccttgatgca | 74 | 70 |
| 107823 | 3' UTR | 3 | 1936 | atggcaaagccttccattcc | 26 | 71 |
| 107824 | 3' UTR | 3 | 1973 | gtcctccttcccagtactgg | 60 | 72 |
| 107825 | 3' UTR | 3 | 2011 | ttacccacaatatcactaaa | 39 | 73 |
| 107826 | 3' UTR | 3 | 2045 | attatatattatagcattgt | 24 | 74 |
| 107827 | 3' UTR | 3 | 2080 | tcacatcatgtttcttatta | 48 | 75 |
| 107828 | 3' UTR | 3 | 2115 | ataacagggaggagaataag | 0 | 76 |

TABLE 1-continued

Inhibition of human PTP1B mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 107829 | 3' UTR | 3 | 2170 | ttacatgcattctaatacac | 21 | 77 |
| 107830 | 3' UTR | 3 | 2223 | gatcaaagtttctcatttca | 81 | 78 |
| 107831 | 3' UTR | 3 | 2274 | ggtcatgcacaggcaggttg | 82 | 79 |
| 107832 | 3' UTR | 3 | 2309 | caacaggcttaggaaccaca | 65 | 80 |
| 107833 | 3' UTR | 3 | 2344 | aactgcaccctattgctgag | 61 | 81 |
| 107834 | 3' UTR | 3 | 2380 | gtcatgccaggaattagcaa | 0 | 82 |
| 107835 | 3' UTR | 3 | 2413 | acaggctgggcctcaccagg | 58 | 83 |
| 107836 | 3' UTR | 3 | 2443 | tgagttacagcaagaccctg | 44 | 84 |
| 107837 | 3' UTR | 3 | 2473 | gaatatggcttcccataccc | 0 | 85 |
| 107838 | 3' UTR | 3 | 2502 | ccctaaatcatgtccagagc | 87 | 86 |
| 107839 | 3' UTR | 3 | 2558 | gacttggaatggcggaggct | 74 | 87 |
| 107840 | 3' UTR | 3 | 2587 | caaatcacggtctgctcaag | 31 | 88 |
| 107841 | 3' UTR | 3 | 2618 | gaagtgtggtttccagcagg | 56 | 89 |
| 107842 | 3' UTR | 3 | 2648 | cctaaaggaccgtcacccag | 42 | 90 |
| 107843 | 3' UTR | 3 | 2678 | gtgaaccgggacagagacgg | 25 | 91 |
| 107844 | 3' UTR | 3 | 2724 | gccccacagggtttgagggt | 53 | 92 |
| 107845 | 3' UTR | 3 | 2755 | cctttgcaggaagagtcgtg | 75 | 93 |
| 107846 | 3' UTR | 3 | 2785 | aaagccacttaatgtggagg | 79 | 94 |
| 107847 | 3' UTR | 3 | 2844 | gtgaaaatgctggcaagaga | 86 | 95 |
| 107848 | 3' UTR | 3 | 2970 | tcagaatgcttacagcctgg | 61 | 96 |

As shown in Table 1, SEQ ID NOs 18, 19, 20, 21, 22, 23, 24, 26, 27, 29, 30, 32, 33, 35, 36, 38, 39, 40, 42, 45, 46, 47, 48, 49, 50, 52, 53, 54, 55, 56, 57, 58, 59, 60, 61, 62, 63, 64, 65, 66, 67, 69, 70, 72, 73, 75, 78, 79, 80, 81, 83, 84, 86, 87, 89, 90, 92, 93, 94, 95, and 96 demonstrated at least 35% inhibition of human PTP1B expression in this assay and are therefore preferred.

Example 16

Antisense Inhibition of Rat PTP1B Expression by Chimeric Phosphorothioate Oligonucleotides Having 2'-MOE Wings and a Deoxy Gap In accordance with the present invention, a second series of oligonucleotides were designed to target different regions of the rat PTP1B RNA, using published sequences (GenBank accession number M33962, incorporated herein as SEQ ID NO: 10). The oligonucleotides are shown in Table 2. "Target site" indicates the first (5'-most) nucleotide number on the particular target sequence to which the oligonucleotide binds. All compounds in Table 2 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphoro-thioate (P=S) throughout the oligonucleotide. All cytidine residues are 5-methylcytidines. The compounds were analyzed for their effect on rat PTP1B mRNA levels by quantitative real-time PCR as described in other examples herein. Data are averages from two experiments. If present, "N.D." indicates "no data".

TABLE 2

Inhibition of rat PTP1B mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 111549 | 5' UTR | 10 | 1 | caacctccccagcagcggct | 32 | 97 |
| 111550 | 5' UTR | 10 | 33 | tcgaggcccgtcgcccgcca | 27 | 98 |

TABLE 2-continued

Inhibition of rat PTP1B mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 111551 | 5' UTR | 10 | 73 | cctcggccgtccgccgcgct | 34 | 99 |
| 111552 | Coding | 10 | 132 | tcgatctgctcgaattcctt | 49 | 100 |
| 113669 | Coding | 10 | 164 | cctggtaaatagccgcccag | 36 | 101 |
| 113670 | Coding | 10 | 174 | tgtcgaatatcctggtaaat | 63 | 102 |
| 113671 | Coding | 10 | 184 | actggcttcatgtcgaatat | 58 | 103 |
| 113672 | Coding | 10 | 189 | aagtcactggcttcatgtcg | 40 | 104 |
| 111553 | Coding | 10 | 190 | gaagtcactggcttcatgtc | 27 | 105 |
| 113673 | Coding | 10 | 191 | ggaagtcactggcttcatgt | 54 | 106 |
| 113674 | Coding | 10 | 192 | gggaagtcactggcttcatg | 41 | 107 |
| 113675 | Coding | 10 | 193 | tgggaagtcactggcttcat | 56 | 108 |
| 113676 | Coding | 10 | 194 | atgggaagtcactggcttca | 31 | 109 |
| 113677 | Coding | 10 | 195 | catgggaagtcactggcttc | 59 | 110 |
| 113678 | Coding | 10 | 225 | tttttgttcttaggaagttt | 24 | 111 |
| 111554 | Coding | 10 | 228 | cggttttgttcttaggaag | 45 | 112 |
| 111555 | Coding | 10 | 269 | tccgactgtggtcaaaggg | 39 | 113 |
| 113679 | Coding | 10 | 273 | ttaatccgactgtggtcaaa | 45 | 114 |
| 113680 | Coding | 10 | 298 | atagtcattatcttcctgat | 49 | 115 |
| 111556 | Coding | 10 | 303 | ttgatatagtcattatcttc | 29 | 116 |
| 113681 | Coding | 10 | 330 | gcttcctccattttatcaa | 67 | 117 |
| 111557 | Coding | 10 | 359 | ggccctgggtgaggatatag | 20 | 118 |
| 113682 | Coding | 10 | 399 | cacaccatctcccagaagtg | 29 | 119 |
| 111558 | Coding | 10 | 405 | tgctcccacaccatctccca | 48 | 120 |
| 113683 | Coding | 10 | 406 | ctgctcccacaccatctccc | 51 | 121 |
| 113684 | Coding | 10 | 407 | tctgctcccacaccatctcc | 37 | 122 |
| 113685 | Coding | 10 | 408 | ttctgctcccacaccatctc | 54 | 123 |
| 113686 | Coding | 10 | 417 | cccctgctcttctgctccca | 60 | 124 |
| 111559 | Coding | 10 | 438 | atgcggttgagcatgaccac | 15 | 125 |
| 113687 | Coding | 10 | 459 | tttaacgagcctttctccat | 33 | 126 |
| 113688 | Coding | 10 | 492 | ttttcttctttctgtggcca | 54 | 127 |
| 113689 | Coding | 10 | 502 | gaccatctcttttcttctt | 58 | 128 |
| 111560 | Coding | 10 | 540 | tcagagatcagtgtcagctt | 21 | 129 |
| 113690 | Coding | 10 | 550 | cttgacatcttcagagatca | 64 | 130 |
| 113691 | Coding | 10 | 558 | taatatgacttgacatcttc | 46 | 131 |
| 111561 | Coding | 10 | 579 | aactccaactgccgtactgt | 14 | 132 |
| 111562 | Coding | 10 | 611 | tctctcgagcctcctgggta | 38 | 133 |
| 113692 | Coding | 10 | 648 | ccaaagtcaggccaggtggt | 63 | 134 |
| 111563 | Coding | 10 | 654 | gggactccaaagtcaggcca | 31 | 135 |

TABLE 2-continued

Inhibition of rat PTP1B mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 113693 | Coding | 10 | 655 | agggactccaaagtcaggcc | 50 | 136 |
| 113694 | Coding | 10 | 656 | cagggactccaaagtcaggc | 45 | 137 |
| 113695 | Coding | 10 | 657 | tcagggactccaaagtcagg | 49 | 138 |
| 113696 | Coding | 10 | 663 | ggtgactcagggactccaaa | 34 | 139 |
| 111564 | Coding | 10 | 705 | cctgactctcggactttgaa | 53 | 140 |
| 113697 | Coding | 10 | 715 | gctgagtgagcctgactctc | 57 | 141 |
| 113698 | Coding | 10 | 726 | ccgtgctctgggctgagtga | 48 | 142 |
| 111565 | Coding | 10 | 774 | aaggtccctgacctgccaat | 28 | 143 |
| 111566 | Coding | 10 | 819 | tctttcctcttgtccatcag | 34 | 144 |
| 113699 | Coding | 10 | 820 | gtctttcctcttgtccatca | 41 | 145 |
| 113700 | Coding | 10 | 821 | ggtctttcctcttgtccatc | 66 | 146 |
| 113701 | Coding | 10 | 822 | gggtctttcctcttgtccat | 71 | 147 |
| 113702 | Coding | 10 | 852 | aacagcactttcttgatgtc | 39 | 148 |
| 111567 | Coding | 10 | 869 | ggaacctgcgcatctccaac | 0 | 149 |
| 111568 | Coding | 10 | 897 | tggtcggccgtctggatgag | 29 | 150 |
| 113703 | Coding | 10 | 909 | gagaagcgcagttggtcggc | 48 | 151 |
| 113704 | Coding | 10 | 915 | aggtaggagaagcgcagttg | 31 | 152 |
| 113705 | Coding | 10 | 918 | gccaggtaggagaagcgcag | 41 | 153 |
| 111569 | Coding | 10 | 919 | agccaggtaggagaagcgca | 56 | 154 |
| 113706 | Coding | 10 | 920 | cagccaggtaggagaagcgc | 58 | 155 |
| 113707 | Coding | 10 | 921 | acagccaggtaggagaagcg | 43 | 156 |
| 113708 | Coding | 10 | 922 | cacagccaggtaggagaagc | 49 | 157 |
| 113709 | Coding | 10 | 923 | tcacagccaggtaggagaag | 47 | 158 |
| 111570 | Coding | 10 | 924 | atcacagccaggtaggagaa | 51 | 159 |
| 113710 | Coding | 10 | 925 | gatcacagccaggtaggaga | 51 | 160 |
| 113711 | Coding | 10 | 926 | cgatcacagccaggtaggag | 63 | 161 |
| 113712 | Coding | 10 | 927 | tcgatcacagccaggtagga | 71 | 162 |
| 113713 | Coding | 10 | 932 | caccctcgatcacagccagg | 75 | 163 |
| 113714 | Coding | 10 | 978 | tccttccactgatcctgcac | 97 | 164 |
| 111571 | Coding | 10 | 979 | ctccttccactgatcctgca | 89 | 165 |
| 113715 | Coding | 10 | 980 | gctccttccactgatcctgc | 99 | 166 |
| 107799 | Coding | 10 | 981 | agctccttccactgatcctg | 99 | 167 |
| 113716 | Coding | 10 | 982 | aagctccttccactgatcct | 97 | 168 |
| 113717 | Coding | 10 | 983 | aaagctccttccactgatcc | 95 | 169 |
| 113718 | Coding | 10 | 984 | gaaagctccttccactgatc | 95 | 170 |
| 113719 | Coding | 10 | 985 | ggaaagctccttccactgat | 95 | 171 |
| 111572 | Coding | 10 | 986 | gggaaagctccttccactga | 89 | 172 |

TABLE 2-continued

Inhibition of rat PTP1B mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 113720 | Coding | 10 | 987 | tgggaaagctccttccactg | 97 | 173 |
| 113721 | Coding | 10 | 1036 | tggccggggaggtgggggca | 20 | 174 |
| 111573 | Coding | 10 | 1040 | tgggtggccggggaggtggg | 20 | 175 |
| 113722 | Coding | 10 | 1046 | tgcgtttgggtggccgggga | 18 | 176 |
| 111574 | Coding | 10 | 1073 | tgcacttgccattgtgaggc | 38 | 177 |
| 113723 | Coding | 10 | 1206 | acttcagtgtcttgactcat | 67 | 178 |
| 113724 | Coding | 10 | 1207 | aacttcagtgtcttgactca | 60 | 179 |
| 111575 | Coding | 10 | 1208 | taacttcagtgtcttgactc | 50 | 180 |
| 113725 | Coding | 10 | 1209 | ctaacttcagtgtcttgact | 53 | 181 |
| 111576 | Coding | 10 | 1255 | gacagatgcctgagcacttt | 32 | 182 |
| 106409 | Coding | 10 | 1333 | gaccaggaagggcttccagt | 32 | 183 |
| 113726 | Coding | 10 | 1334 | tgaccaggaagggcttccag | 39 | 184 |
| 111577 | Coding | 10 | 1335 | ttgaccaggaagggcttcca | 32 | 185 |
| 113727 | Coding | 10 | 1336 | gttgaccaggaagggcttcc | 41 | 186 |
| 113728 | Coding | 10 | 1342 | gcacacgttgaccaggaagg | 59 | 187 |
| 111578 | Coding | 10 | 1375 | gaggtacgcgccagtcgcca | 45 | 188 |
| 111579 | Coding | 10 | 1387 | tacccggtaacagaggtacg | 32 | 189 |
| 111580 | Coding | 10 | 1397 | agtgaaaacatacccggtaa | 30 | 190 |
| 111581 | 3' UTR | 10 | 1456 | caaatcctaacctgggcagt | 31 | 191 |
| 111582 | 3' UTR | 10 | 1519 | ttccagttccaccacaggct | 24 | 192 |
| 111583 | 3' UTR | 10 | 1552 | ccagtgcacagatgcccctc | 47 | 193 |
| 111584 | 3' UTR | 10 | 1609 | acaggttaaggccctgagat | 29 | 194 |
| 111585 | 3' UTR | 10 | 1783 | gcctagcatcttttgttttc | 43 | 195 |
| 111586 | 3' UTR | 10 | 1890 | aagccagcaggaactttaca | 36 | 196 |
| 111587 | 3' UTR | 10 | 2002 | gggacacctgagggaagcag | 16 | 197 |
| 111588 | 3' UTR | 10 | 2048 | ggtcatctgcaagatggcgg | 40 | 198 |
| 111589 | 3' UTR | 10 | 2118 | gccaacctctgatgaccctg | 25 | 199 |
| 111590 | 3' UTR | 10 | 2143 | tggaagcccagctctaagc | 25 | 200 |
| 111591 | 3' UTR | 10 | 2165 | tagtaatgactttccaatca | 44 | 201 |
| 111592 | 3' UTR | 10 | 2208 | tgagtcttgctttacacctc | 41 | 202 |
| 111593 | 3' UTR | 10 | 2252 | cctgcgcgcggagtgacttc | 22 | 203 |
| 111594 | 3' UTR | 10 | 2299 | aggacgtcactgcagcagga | 43 | 204 |
| 111595 | 3' UTR | 10 | 2346 | tcaggacaagtcttggcagt | 32 | 205 |
| 111596 | 3' UTR | 10 | 2405 | gaggctgcacagtaagcgct | 34 | 206 |
| 111597 | 3' UTR | 10 | 2422 | tcagccaaccagcatcagag | 20 | 207 |
| 111598 | 3' UTR | 10 | 2449 | acccacagtgtccacctccc | 30 | 208 |
| 111599 | 3' UTR | 10 | 2502 | agtgcgggctgtgctgctgg | 30 | 209 |

TABLE 2-continued

Inhibition of rat PTP1B mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 111600 | 3' UTR | 10 | 2553 | cagctcgctctggcggcctc | 8 | 210 |
| 111601 | 3' UTR | 10 | 2608 | aggaagggagctgcacgtcc | 32 | 211 |
| 111602 | 3' UTR | 10 | 2664 | ccctcacgattgctcgtggg | 24 | 212 |
| 111603 | 3' UTR | 10 | 2756 | cagtggagcggctcctctgg | 18 | 213 |
| 111604 | 3' UTR | 10 | 2830 | caggctgacaccttacacgg | 30 | 214 |
| 111605 | 3' UTR | 10 | 2883 | gtcctacctcaaccctagga | 37 | 215 |
| 111606 | 3' UTR | 10 | 2917 | ctgccccagcaccagccaca | 12 | 216 |
| 111607 | 3' UTR | 10 | 2946 | attgcttctaagaccctcag | 33 | 217 |
| 111608 | 3' UTR | 10 | 2978 | ttacatgtcaccactgttgt | 28 | 218 |
| 111609 | 3' UTR | 10 | 3007 | tacacatgtcatcagtagcc | 37 | 219 |
| 111610 | 3' UTR | 10 | 3080 | ttttctaactcacagggaaa | 30 | 220 |
| 111611 | 3' UTR | 10 | 3153 | gtcccgccagtgagcaggc | 23 | 221 |
| 111612 | 3' UTR | 10 | 3206 | cggcctcggcactggacagc | 27 | 222 |
| 111613 | 3' UTR | 10 | 3277 | gtggaatgtctgagatccag | 31 | 223 |
| 111614 | 3' UTR | 10 | 3322 | agggcgggcctgcttgccca | 23 | 224 |
| 111615 | 3' UTR | 10 | 3384 | cggtcctggcctgctccaga | 31 | 225 |
| 111616 | 3' UTR | 10 | 3428 | tacactgttcccaggagggt | 42 | 226 |
| 111617 | 3' UTR | 10 | 3471 | tggtgccagcagcgctagca | 10 | 227 |
| 111618 | 3' UTR | 10 | 3516 | cagtctcttcagcctcaaga | 43 | 228 |
| 113729 | 3' UTR | 10 | 3537 | aagagtcatgagcaccatca | 56 | 229 |
| 111619 | 3' UTR | 10 | 3560 | tgaaggtcaagttcccctca | 40 | 230 |
| 111620 | 3' UTR | 10 | 3622 | ctggcaagaggcagactgga | 30 | 231 |
| 111621 | 3' UTR | 10 | 3666 | ggctctgtgctggcttctct | 52 | 232 |
| 111622 | 3' UTR | 10 | 3711 | gccatctcctcagcctgtgc | 39 | 233 |
| 111623 | 3' UTR | 10 | 3787 | agcgcctgctctgaggcccc | 16 | 234 |
| 111624 | 3' UTR | 10 | 3854 | tgctgagtaagtattgactt | 35 | 235 |
| 111625 | 3' UTR | 10 | 3927 | ctatggccatttagagagag | 36 | 236 |
| 113730 | 3' UTR | 10 | 3936 | tggtttattctatggccatt | 59 | 237 |
| 111626 | 3' UTR | 10 | 3994 | cgctcctgcaaaggtgctat | 11 | 238 |
| 111627 | 3' UTR | 10 | 4053 | gttggaaacggtgcagtcgg | 39 | 239 |
| 111628 | 3' UTR | 10 | 4095 | atttattgttgcaactaatg | 33 | 240 |

As shown in Table 2, SEQ ID NOs 97, 99, 100, 101, 102, 103, 104, 106, 107, 108, 109, 110, 112, 113, 114, 115, 117, 120, 121, 122, 123, 124, 126, 127, 128, 130, 131, 133, 134, 135, 136, 137, 138, 139, 140, 141, 142, 144, 145, 146, 147, 148, 151, 152, 153, 154, 155, 156, 157, 158, 159, 160, 161, 162, 163, 164, 165, 166, 167, 168, 169, 170, 171, 172, 173, 177, 178, 179, 180, 181, 182, 183, 184, 185, 186, 187, 188, 189, 191, 193, 195, 196, 198, 201, 202, 204, 205, 206, 211, 215, 217, 219, 223, 225, 226, 228, 229, 230, 232, 233, 235, 236, 237, 239 and 240 demonstrated at least 30% inhibition of rat PTP1B expression in this experiment and are therefore preferred.

Example 17

Western Blot Analysis of PTP1B Protein Levels

Western blot analysis (immunoblot analysis) is carried out using standard methods. Cells are harvested 16-20 h after oligonucleotide treatment, washed once with PBS, suspended in Laemmli buffer (100 µL/well), boiled for 5 minutes and loaded on a 16% SDS-PAGE gel. Gels are run for 1.5 hours at 150 V, and transferred to membrane for western blotting. Appropriate primary antibody directed to PTP1B is used, with a radiolabelled or fluorescently labeled secondary antibody directed against the primary antibody species. Bands are visualized using a PHOSPHORIMAGER™ instrument (Molecular Dynamics, Sunnyvale Calif.).

Example 18

Effects of Antisense Inhibition of PTP1B (ISIS 113715) on Blood Glucose Levels db/db mice are used as a model of Type 2 diabetes. These mice are hyperglycemic, obese, hyperlipidemic, and insulin resistant. The db/db phenotype is due to a mutation in the leptin receptor on a C57BLKS background. However, a mutation in the leptin gene on a different mouse background can produce obesity without diabetes (ob/ob mice). Leptin is a hormone produced by fat that regulates appetite and animals or humans with leptin deficiencies become obese. Heterozygous db/wt mice (known as lean littermates) do not display the hyperglycemia/hyperlipidemia or obesity phenotype and are used as controls.

In accordance with the present invention, ISIS 113715 (GCTCCTTCCACTGATCCTGC, SEQ ID No: 166) was investigated in experiments designed to address the role of PTP1B in glucose metabolism and homeostasis. ISIS 113715 is completely complementary to sequences in the coding region of the human, rat, and mouse PTP1B nucleotide sequences incorporated herein as SEQ ID No: 3 (starting at nucleotide 951 of human PTP1B; Genbank Accession No. M31724), SEQ ID No: (starting at nucleotide 980 of rat PTP1B; Genbank Accession No. M33962) and SEQ ID No: 241 (starting at nucleotide 1570 of mouse PTP1B; Genbank Accession No. U24700). The control used is ISIS 29848 (NNNNNNNNNNNNNNNNNNNN, SEQ ID No: 242) where N is a mixture of A, G, T and C.

Male db/db mice and lean (heterozygous, i.e., db/wt) littermates (age 9 weeks at time 0) were divided into matched groups (n=6) with the same average blood glucose levels and treated by intraperitoneal injection once a week with saline, ISIS 29848 (the control oligonucleotide) or ISIS 113715. db/db mice were treated at a dose of 10, 25 or 50 mg/kg of ISIS 113715 or 50 mg/kg of ISIS 29848 while lean littermates were treated at a dose of 50 or 100 mg/kg of ISIS 113715 or 100 mg/kg of ISIS 29848. Treatment was continued for 4 weeks with blood glucose levels being measured on day 0, 7, 14, 21 and 28.

By day 28 in db/db mice, blood glucose levels were reduced at all doses from a starting level of 300 mg/dL to 225 mg/dL for the 10 mg/kg dose, 175 mg/dL for the 25 mg/kg dose and 125 mg/dL for the 50 mg/kg dose. These final levels are within normal range for wild-type mice (170 mg/dL). The mismatch control and saline treated levels were 320 mg/dL and 370 mg/dL at day 28, respectively.

In lean littermates, blood glucose levels remained constant throughout the study for all treatment groups (average 120 mg/dL). These results indicate that treatment with ISIS 113715 reduces blood glucose in db/db mice and that there is no hypoglycemia induced in the db/db or the lean littermate mice as a result of the oligonucleotide treatment.

In a similar experiment, ob/ob mice and their lean littermates (heterozygous, i.e., ob/wt) were dosed twice a week at 50 mg/kg with ISIS 113715, ISIS 29848 or saline control and blood glucose levels were measured at the end of day 7, 14 and 21. Treatment of ob/ob mice with ISIS 113715 resulted in the largest decrease in blood glucose over time going from 225 mg/dL at day 7 to 95 mg/dL at day 21. Ob/ob mice displayed an increase in plasma glucose over time from 300 mg/dL to 325 mg/dL while treatment with the control oligonucleotide reduced plasma glucose from an average of 280 mg/dL to 130 mg/dL. In the lean littermates plasma glucose levels remained unchanged in all treatment groups (average level 100 mg/dL).

Example 19

Effects of Antisense Inhibition of PTP1B (ISIS 113715) on mRNA Expression in Liver Male db/db mice and lean littermates (age 9 weeks at time 0) were divided into matched groups (n=6) with the same average blood glucose levels and treated by intraperitoneal injection once a week with saline, ISIS 29848 (the control oligonucleotide) or ISIS 113715. db/db mice were treated at a dose of 10, 25 or 50 mg/kg of ISIS 113715 or 50 mg/kg of ISIS 29848 while lean littermates were treated at a dose of 50 or 100 mg/kg of ISIS 113715 or 100 mg/kg of ISIS 29848. Treatment was continued for 4 weeks after which the mice were sacrificed and tissues collected for mRNA analysis. RNA values were normalized and are expressed as a percentage of saline treated control.

ISIS 113715 successfully reduced PTP1B mRNA levels in the livers of db/db mice at all doses examined (60% reduction of PTP1B mRNA), whereas the control oligonucleotide treated animals showed no reduction in PTP1B mRNA, remaining at the level of the saline treated control. Treatment of lean littermates with ISIS 113715 also reduced mRNA levels to 45% of control at the 50 mg/kg dose and 25% of control at the 100 mg/kg dose. The control oligonucleotide (ISIS 29848) failed to show any reduction in mRNA levels.

Example 20

Effects of Antisense Inhibition of PTP1B (ISIS 113715) on Body Weight

Male db/db mice and lean littermates (age 9 weeks at time 0) were divided into matched groups (n=6) with the same average blood glucose levels and treated by intraperitoneal injection once a week with saline, ISIS 29848 (the control oligonucleotide) or ISIS 113715. db/db mice were treated at a dose of 10, 25 or 50 mg/kg of ISIS 113715 or 50 mg/kg of ISIS 29848 while lean littermates were treated at a dose of 50 or 100 mg/kg of ISIS 113715 or 100 mg/kg of ISIS 29848. Treatment was continued for 4 weeks. At day 28 mice were sacrificed and final body weights were measured.

Treatment of ob/ob mice with ISIS 113715 resulted in an increase in body weight which was constant over the dose range with animals gaining an average of 11.0 grams while saline treated controls gained 5.5 grams. Animals treated with the control oligonucleotide gained an average of 7.8 grams of body weight.

Lean littermate animals treated with 50 or 100 mg/kg of ISIS 113715 gained 3.8 grams of body weight compared to a gain of 3.0 grams for the saline controls.

In a similar experiment, ob/ob mice and their lean littermates were dosed twice a week at 50 mg/kg with ISIS 113715, ISIS 29848 or saline control and body weights were measured at the end of day 7, 14 and 21.

Treatment of the ob/ob mice with ISIS 113715, ISIS 29848 or saline control all resulted in a similar increase in body weight across the 21-day timecourse. At the end of day 7 all ob/ob treatment groups had an average weight of 42 grams. By day 21, animals treated with ISIS 113715 had an average body weight of 48 grams, while those in the ISIS 29848 (control oligonucleotide) and saline control group each had an average body weight of 52 grams. All of the lean littermates had an average body weight of 25 grams at the beginning of the timecourse and all lean littermate treatment groups showed an increase in body weight, to 28 grams, by day 21.

Example 21

Effects of Antisense Inhibition of PTP1B (ISIS 113715) on Plasma Insulin Levels

Male db/db mice (age 9 weeks at time 0) were divided into matched groups (n=6) with the same average blood glucose levels and treated by intraperitoneal injection twice a week with saline, ISIS 29848 (the control oligonucleotide) or ISIS 113715 at a dose of 50 mg/kg. Treatment was continued for 3 weeks with plasma insulin levels being measured on day 7, 14, and 21.

Mice treated with ISIS 113715 showed a decrease in plasma insulin levels from 15 ng/mL at day 7 to 7.5 ng/mL on day 21. Saline treated animals have plasma insulin levels of 37 ng/mL at day 7, which dropped to 25 ng/mL on day 14, but rose again to 33 ng/mL by day 21. Mice treated with the control oligonucleotide also showed a decrease in plasma insulin levels across the timecourse of the study from 25 ng/mL at day 7 to 10 ng/mL on day 21. However, ISIS 113715 was the most effective at reducing plasma insulin over time.

Example 22

Antisense Inhibition of Human PTP1B Expression by Additional Chimeric Phosphorothioate Oligonucleotides Having 2'-MOE Wings and a Deoxy Gap In accordance with the present invention, an additional series of oligonucleotides were designed to target different genomic regions of the human PTP1B RNA, using published sequences (GenBank accession number M31724, incorporated herein as SEQ ID NO: 3), and concatenated genomic sequence derived from nucleotide residues 1-31000 of Genbank accession number AL034429 followed by nucleotide residues 1-45000 of Genbank accession number AL133230, incorporated herein as SEQ ID NO: 243). The oligonucleotides are shown in Table 3. "Target site" indicates the first (5'-most) nucleotide number on the particular target sequence to which the oligonucleotide binds. All compounds in Table 3 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphoro-thioate (P=S) throughout the oligonucleotide. All cytidine residues are 5-methylcytidines. The compounds were analyzed for their effect on human PTP1B mRNA levels by quantitative real-time PCR as described in other examples herein. Data are averages from two experiments. If present, "N.D." indicates "no data".

TABLE 3

Inhibition of human PTP1B mRNA levels by chimeric phosphorothioate oligonucleotides having 2'-MOE wings and a deoxy gap

| Isis # | REGION | TARGET SEQ ID NO | TARGET SITE | SEQUENCE | % INHIB | SEQ ID NO |
|---|---|---|---|---|---|---|
| 142020 | 5' UTR | 3 | 6 | GCGCTCTTAGCCCCGAGGCC | 61 | 244 |
| 142021 | 5' UTR | 3 | 65 | CCAGGGCGGCTGCTGCGCCT | 56 | 245 |
| 142022 | Start Codon | 3 | 80 | CATCTCCATGACGGGCCAGG | 4 | 246 |
| 142023 | Start Codon | 3 | 85 | TTTTCCATCTCCATGACGGG | 67 | 247 |
| 142024 | Start Codon | 3 | 90 | ACTCCTTTTCCATCTCCATG | 71 | 248 |
| 142025 | Exon 1 | 3 | 106 | TTGTCGATCTGCTCGAACTC | 61 | 249 |
| 142026 | Exon 1 | 3 | 109 | GACTTGTCGATCTGCTCGAA | 66 | 250 |
| 142027 | Exon 1 | 3 | 116 | GCTCCCGGACTTGTCGATCT | 95 | 251 |
| 142028 | Exon 1 | 3 | 119 | CCAGCTCCCGGACTTGTCGA | 92 | 252 |
| 142029 | Exon:Exon Junction | 3 | 945 | TCCACTGATCCTGCACGGAA | 44 | 253 |
| 142030 | Exon:Exon Junction | 3 | 948 | CCTTCCACTGATCCTGCACG | 55 | 254 |
| 142031 | 3' UTR | 3 | 1453 | ATGCCTGCTAGTCGGGCGTG | 67 | 255 |
| 142032 | 3' UTR | 3 | 1670 | CGGGTGTAGGCCCCTTCCCT | 74 | 256 |

TABLE 3-continued

Inhibition of human PTP1B mRNA levels by chimeric phosphorothioate oligonucleotides having 2'-MOE wings and a deoxy gap

| Isis # | REGION | TARGET SEQ ID NO | TARGET SITE | SEQUENCE | % INHIB | SEQ ID NO |
|---|---|---|---|---|---|---|
| 142033 | 3' UTR | 3 | 1772 | ATGGAGTGGAGAGTTGCTCC | 63 | 257 |
| 142034 | 3' UTR | 3 | 1893 | TTGTACTTTTTGATAAAGCC | 61 | 258 |
| 142035 | 3' UTR | 3 | 1962 | CAGTACTGGTCTGACGCAGC | 68 | 259 |
| 142036 | 3' UTR | 3 | 2018 | TCTCACGTTACCCACAATAT | 74 | 260 |
| 142037 | 3' UTR | 3 | 2070 | TTTCTTATTAAATACCCACG | 61 | 261 |
| 142038 | 3' UTR | 3 | 2088 | AAGTAATCTCACATCATGTT | 79 | 262 |
| 142039 | 3' UTR | 3 | 2314 | TTCAGCAACAGGCTTAGGAA | 51 | 263 |
| 142040 | 3' UTR | 3 | 2323 | GACAATGACTTCAGCAACAG | 43 | 264 |
| 142041 | 3' UTR | 3 | 2359 | TGCCTATTCCTGGAAAACTG | 43 | 265 |
| 142042 | 3' UTR | 3 | 2395 | GGAAGTCACTAGAGTGTCAT | 14 | 266 |
| 142043 | 3' UTR | 3 | 2418 | CCAGGACAGGCTGGGCCTCA | 67 | 267 |
| 142044 | 3' UTR | 3 | 2426 | CTGCTGTACCAGGACAGGCT | 73 | 268 |
| 142045 | 3' UTR | 3 | 2452 | TGGAATGTCTGAGTTACAGC | 74 | 269 |
| 142046 | 3' UTR | 3 | 2566 | AGAGTGTTGACTTGGAATGG | 43 | 270 |
| 142047 | 3' UTR | 3 | 2574 | GCTCAAGAAGAGTGTTGACT | 76 | 271 |
| 142048 | 3' UTR | 3 | 2598 | TGCCTCTCTTCCAAATCACG | 43 | 272 |
| 142049 | 3' UTR | 3 | 2800 | TGTTTTTCATGTTAAAAAGC | 44 | 273 |
| 142050 | 3' UTR | 3 | 2895 | TCCCACCACAGAATTTCTCT | 21 | 274 |
| 142051 | 3' UTR | 3 | 2921 | GCTCTGCAGGGTGACACCTC | 74 | 275 |
| 142052 | 3' UTR | 3 | 3066 | AGGAGGTTAAACCAGTACGT | 78 | 276 |
| 142053 | 3' UTR | 3 | 3094 | GGTGGAGAGCCAGCTGCTCT | 59 | 277 |
| 142054 | 3' UTR | 3 | 3153 | TATTGGCTTAAGGCATATAG | 72 | 278 |
| 142055 | 3' UTR | 3 | 3168 | GACCTGATGAGTAAATATTG | 58 | 279 |
| 142084 | 5' UTR | 243 | 859 | TTCTTCATGTCAACCGGCAG | 11 | 280 |
| 142085 | 5' UTR | 243 | 919 | GCCCCGAGGCCCGCTGCAAT | 83 | 281 |
| 142056 | Intron 1 | 243 | 4206 | TAGTGAACTATTGTTACAAC | 70 | 282 |
| 142057 | Intron 1 | 243 | 27032 | TGCTAAGCCACTTCTAATCA | 72 | 283 |
| 142058 | Intron 1 | 243 | 27203 | CAGGATTCTAAGTTATTAAA | 32 | 284 |
| 142059 | Intron 1 | 243 | 33720 | TGGGCAGGATGGCTCTGGTA | 21 | 285 |
| 142060 | Intron 1 | 243 | 48065 | TACAATACTATCTGTGACTA | 34 | 286 |
| 142061 | Exon: Intron Junction | 243 | 51931 | GATACTTACAGGGACTGACG | 39 | 287 |
| 142086 | Intron 2 | 243 | 52005 | AACCCTGAGGCGAAAGGAG | 64 | 288 |
| 142062 | Intron 2 | 243 | 54384 | CCCCAGGTCACTAAAATTAA | 48 | 289 |
| 142063 | Intron 2 | 243 | 55362 | AAAGCAAAGGTGAGTTGGT | 56 | 290 |
| 142064 | Intron 3 | 243 | 56093 | GCTCAATTATTAAACCACTT | 64 | 291 |
| 142065 | Intron 3 | 243 | 56717 | AGTCCTCAAGAAGTCACTTT | 70 | 292 |

TABLE 3-continued

Inhibition of human PTP1B mRNA levels by chimeric phosphorothioate oligonucleotides having 2'-MOE wings and a deoxy gap

| Isis # | REGION | TARGET SEQ ID NO | TARGET SITE | SEQUENCE | % INHIB | SEQ ID NO |
|---|---|---|---|---|---|---|
| 142066 | Intron 4 | 243 | 61780 | GAAAGCAGGGACTGCTGGC | 39 | 293 |
| 142067 | Intron 4 | 243 | 64554 | AAAACTGGGAGAGACAGCA | 71 | 294 |
| 142068 | Intron 4 | 243 | 64869 | ACATGGAAGCCATGGTCAGC | 24 | 295 |
| 142069 | Intron 5 | 243 | 67516 | ATTGCTAGACTCACACTAGG | 68 | 296 |
| 142070 | Intron 5 | 243 | 68052 | GGCTGTGATCAAAAGGCAG | 51 | 297 |
| 142087 | Intron 5 | 243 | 68481 | CACTGGCTCTGGGCAACTTT | 70 | 298 |
| 142088 | Intron 5 | 243 | 68563 | GCTGGGCAGCCACCCATAAA | 71 | 299 |
| 142071 | Intron 5 | 243 | 68648 | AGTCCCCTCACCTCTTTTCT | 59 | 300 |
| 142072 | Exon: Intron | 243 | 69107 | CCTCCTTACCAGCAAGAGGC | 26 | 301 |
| 142089 | Intron 6 | 243 | 69198 | TGTATTTTGGAAGAGGAGCG | 53 | 302 |
| 142090 | Intron 6 | 243 | 69220 | ACAGACTAACACAGTGAGTC | 53 | 303 |
| 142073 | Intron 6 | 243 | 69264 | ACAAATTACCGAGTCTCAGG | 47 | 304 |
| 142074 | Intron 6 | 243 | 69472 | TCATGAAAGGCTTGGTGCCC | 41 | 305 |
| 142075 | Intron 7 | 243 | 70042 | TTGGAAGATGAAATCTTTTG | 30 | 306 |
| 142076 | Intron 7 | 243 | 70052 | AGCCATGTACTTGGAAGATG | 69 | 307 |
| 142077 | Intron 8 | 243 | 70661 | CGAGCCCCTCATTCCAACAA | 42 | 308 |
| 142078 | Intron 8 | 243 | 71005 | CACCTCAGCGGACACCTCTA | 6 | 309 |
| 142079 | Exon: Intron | 243 | 71938 | GAAACATACCCTGTAGCAGA | 52 | 310 |
| 142091 | Intron 9 | 243 | 72131 | CAGAGGGCTCCTTAAAACCC | 61 | 311 |
| 142092 | Intron 9 | 243 | 72430 | ATTCGTAAAAGTTTGGGATT | 34 | 312 |
| 142080 | Intron 9 | 243 | 72453 | CCCTCTTCTCCAAGGGAGTT | 73 | 313 |
| 142081 | Intron 9 | 243 | 73158 | GGAATGAAACCAAACAGTT | 42 | 314 |
| 142082 | Exon 10 | 243 | 75012 | AAATGGTTTATTCCATGGCC | 66 | 315 |
| 142083 | Exon 10 | 243 | 75215 | AAAAATTTTATTGTTGCAGC | 48 | 316 |
| 142093 | 3' UTR | 243 | 75095 | CCGGTCATGCAGCCACGTAT | 85 | 317 |
| 142094 | 3' UTR | 243 | 75165 | GTTGGAAAACTGTACAGTCT | 77 | 318 |
| 142095 | 3' UTR | 243 | 75211 | ATTTTATTGTTGCAGCTAAA | 46 | 319 |

As shown in Table 3, SEQ ID NOs, 244, 245, 247, 248, 249, 250, 251, 252, 254, 255, 256, 257, 258, 259, 260, 261, 262, 263, 267, 268, 269, 271, 275, 276, 277, 278, 279, 281, 282, 283, 288, 290, 291, 292, 294, 296, 297, 298, 299, 300, 302, 303, 307, 310, 311, 313, 315, 317, and 318, demonstrated at least 50% inhibition of human PTP1B expression in this assay and are therefore preferred.

Example 23

Antisense Inhibition of Human PTP1B Expression by Additional Chimeric Phosphorothioate Oligonucleotides Having 2'-MOE Wings and a Deoxy Gap In accordance with the present invention, an additional series of oligonucleotides were designed to target either the 3'UTR or the 5'UTR of the human PTP1B RNA, using published sequences (GenBank accession number M31724, incorporated herein as SEQ ID NO: 3) and concatenated genomic sequence derived from nucleotide residues 1-31000 of Genbank accession number AL034429 followed by nucleotide residues 1-45000 of Genbank accession number AL133230, incorporated herein as SEQ ID NO: 243. The oligonucleotides are shown in Table 4. "Target site" indicates the first (5'-most) nucleotide number on the particular target sequence to which the oligonucleotide binds. All compounds in Table 3 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphoro-thioate (P=S) throughout the oligonucleotide. All cytidine residues are 5-methylcytidines. The compounds were analyzed for their effect on human PTP1B mRNA levels by quantitative real-time PCR as described in other examples herein. Data are averages from two experiments. If present, "N.D." indicates "no data".

TABLE 4

Inhibition of human PTP1B mRNA levels by chimeric phosphorothioate oligonucleotides having 2'-MOE wings and a deoxy gap

| ISIS # | REGION | TARGET SEQ ID NO. | TARGET SITE | SEQUENCE | % INHIB | SEQ ID NO. |
|---|---|---|---|---|---|---|
| 146879 | 5' UTR | 3 | 50 | CGCCTCCTTCTCGGCCCACT | 29 | 320 |
| 146880 | 5' UTR | 3 | 62 | GGGCGGCTGCTGCGCCTCCT | 34 | 321 |
| 146881 | 3' UTR | 3 | 1601 | GTGGATTTGGTACTCAAAGT | 72 | 322 |
| 146882 | 3' UTR | 3 | 1610 | AAATGGCTTGTGGATTTGGT | 72 | 323 |
| 146883 | 3' UTR | 3 | 1637 | ATGGTACTCTCTTTCACTCT | 61 | 324 |
| 146884 | 3' UTR | 3 | 1643 | GCCAGCATGGTACTCTCTTT | 63 | 325 |
| 146885 | 3' UTR | 3 | 1764 | GAGAGTTGCTCCCTGCAGAT | 62 | 326 |
| 146886 | 3' UTR | 3 | 1770 | GGAGTGGAGAGTTGCTCCC | 57 | 327 |
| 146887 | 3' UTR | 3 | 1874 | CCTTGATGCAAGGCTGACAT | 65 | 328 |
| 146888 | 3' UTR | 3 | 1879 | AAAGCCCTTGATGCAAGGC | 59 | 329 |
| 146889 | 3' UTR | 3 | 1915 | AGTACTACCTGAGGATTTAT | 46 | 330 |
| 146890 | 3' UTR | 3 | 1925 | TTCCATTCCCAGTACTACCT | 41 | 331 |
| 146891 | 3' UTR | 3 | 1938 | CCATGGCAAAGCCTTCCATT | 65 | 332 |
| 146892 | 3' UTR | 3 | 1943 | CAGGCCCATGGCAAAGCCT | 52 | 333 |
| 146893 | 3' UTR | 3 | 1988 | CAACTGCTTACAACCGTCCT | 60 | 334 |
| 146894 | 3' UTR | 3 | 2055 | CCACGTGTTCATTATATATT | 42 | 335 |
| 146895 | 3' UTR | 3 | 2063 | TTAAATACCCACGTGTTCAT | 27 | 336 |
| 146896 | 3' UTR | 3 | 2099 | TAAGCGGGACAAAGTAATC | 47 | 337 |
| 146897 | 3' UTR | 3 | 2118 | CAGATAACAGGGAGGAGAA | 31 | 338 |
| 146898 | 3' UTR | 3 | 2133 | GAGAACTAGATCTAGCAGA | 0 | 339 |
| 146899 | 3' UTR | 3 | 2140 | AGTGATTGAGAACTAGATC | 62 | 340 |
| 146900 | 3' UTR | 3 | 2184 | GACACAAGAAGACCTTACA | 49 | 341 |
| 146901 | 3' UTR | 3 | 2212 | CTCATTTCAAGCACATATTT | 60 | 342 |
| 146902 | 3' UTR | 3 | 2263 | GGCAGGTTGGACTTGGACA | 49 | 343 |
| 146903 | 3' UTR | 3 | 2296 | AACCACAGCCATGTAATGA | 43 | 344 |
| 146904 | 3' UTR | 3 | 2332 | TTGCTGAGCGACAATGACTT | 42 | 345 |
| 146905 | 3' UTR | 3 | 2350 | CTGGAAAACTGCACCCTATT | 31 | 346 |
| 146906 | 3' UTR | 3 | 2409 | GCTGGGCCTCACCAGGAAG | 77 | 347 |
| 146907 | 3' UTR | 3 | 2439 | TTACAGCAAGACCCTGCTGT | 28 | 348 |
| 146908 | 3' UTR | 3 | 2457 | ACCCTTGGAATGTCTGAGTT | 65 | 349 |

TABLE 4-continued

Inhibition of human PTP1B mRNA levels by chimeric phosphorothioate oligonucleotides having 2'-MOE wings and a deoxy gap

| ISIS # | REGION | TARGET SEQ ID NO. | TARGET SITE | SEQUENCE | % INHIB | SEQ ID NO. |
|---|---|---|---|---|---|---|
| 146909 | 3' UTR | 3 | 2464 | TTCCCATACCCTTGGAATGT | 62 | 350 |
| 146910 | 3' UTR | 3 | 2471 | ATATGGCTTCCCATACCCTT | 47 | 351 |
| 146911 | 3' UTR | 3 | 2477 | GTGTGAATATGGCTTCCCAT | 54 | 352 |
| 146912 | 3' UTR | 3 | 2509 | CCTGCTTCCCTAAATCATGT | 65 | 353 |
| 146913 | 3' UTR | 3 | 2514 | GTGTCCCTGCTTCCCTAAAT | 55 | 354 |
| 146914 | 3' UTR | 3 | 2546 | CGGAGGCTGATCCCAAAGG | 55 | 355 |
| 146915 | 3' UTR | 3 | 2602 | CAGGTGCCTCTCTTCCAAAT | 60 | 356 |
| 146916 | 3' UTR | 3 | 2613 | GTGGTTTCCAGCAGGTGCCT | 63 | 357 |
| 146917 | 3' UTR | 3 | 2628 | GCTGTTTCAAGAAGTGTGGT | 43 | 358 |
| 146918 | 3' UTR | 3 | 2642 | GGACCGTCACCCAGGCTGTT | 32 | 359 |
| 146919 | 3' UTR | 3 | 2655 | CAGGCTGCCTAAAGGACCG | 60 | 360 |
| 146920 | 3' UTR | 3 | 2732 | ACCATCAGGCCCCACAGGG | 58 | 361 |
| 146921 | 3' UTR | 3 | 2759 | GTTCCCTTTGCAGGAAGAGT | 69 | 362 |
| 146922 | 3' UTR | 3 | 2772 | GTGGAGGTCTTCAGTTCCCT | 64 | 363 |
| 146923 | 3' UTR | 3 | 2781 | CCACTTAATGTGGAGGTCTT | 54 | 364 |
| 146924 | 3' UTR | 3 | 2814 | AGCTACAGCTGCCGTGTTTT | 51 | 365 |
| 146925 | 3' UTR | 3 | 2862 | CCACAGAGAAAGGCAAAATG | 50 | 366 |
| 146926 | 3' UTR | 3 | 2885 | GAATTTCTCTGTACTGGCTT | 23 | 367 |
| 146927 | 3' UTR | 3 | 2890 | CCACAGAATTTCTCTGTACT | 61 | 368 |
| 146928 | 3' UTR | 3 | 2901 | GAATGTTCCCACCACAGAA | 61 | 369 |
| 146929 | 3' UTR | 3 | 2956 | GCCTGGCACCTAAGCCTTAT | 0 | 370 |
| 146930 | 3' UTR | 3 | 2965 | ATGCTTACAGCCTGGCACCT | 55 | 371 |
| 146931 | 3' UTR | 3 | 3008 | CTACATACATATACAGGACT | 65 | 372 |
| 146932 | 3' UTR | 3 | 3042 | TTTGAAATGCTACTATATAT | 44 | 373 |
| 146933 | 3' UTR | 3 | 3070 | GGATAGGAGGTTAAACCAG | 67 | 374 |
| 146934 | 3' UTR | 3 | 3086 | GCCAGCTGCTCTCCAAGGAT | 42 | 375 |
| 146935 | 3' UTR | 3 | 3121 | CTACCTCTCTAACATAATGT | 39 | 376 |
| 146936 | 3' UTR | 3 | 3126 | GCTCGCTACCTCTCTAACAT | 68 | 377 |
| 146937 | 3' UTR | 3 | 3143 | AGGCATATAGCAGAGCAGC | 61 | 378 |
| 146938 | 5' UTR | 243 | 851 | GTCAACCGGCAGCCGGAAC | 14 | 379 |
| 146942 | 5' UTR | 243 | 891 | CCTGCAGCTACCGCCGCCCT | 69 | 380 |
| 146943 | 5' UTR | 243 | 908 | CGCTGCAATCCCCGACCCCT | 87 | 381 |
| 146944 | 3' UTR | 243 | 75050 | ACCAAAACACCTTGCTTTTT | 27 | 382 |
| 146945 | 3' UTR | 243 | 75057 | GTATTATACCAAAACACCTT | 39 | 383 |
| 146946 | 3' UTR | 243 | 75072 | CACACACCTGAAAGGTAT | 42 | 384 |
| 146947 | 3' UTR | 243 | 75097 | ACCCGGTCATGCAGCCACG | 49 | 385 |
| 146948 | 3' UTR | 243 | 75136 | GTGAGGTCACAGAAGACCC | 49 | 386 |

TABLE 4-continued

Inhibition of human PTP1B mRNA levels by chimeric phosphorothioate oligonucleotides having 2'-MOE wings and a deoxy gap

| ISIS # | REGION | TARGET SEQ ID NO. | TARGET SITE | SEQUENCE | % INHIB | SEQ ID NO. |
|---|---|---|---|---|---|---|
| 146949 | 3' UTR | 243 | 75154 | GTACAGTCTGACAGTTCTGT | 40 | 387 |
| 146950 | 3' UTR | 243 | 75172 | ATGGCAAGTTGGAAAACTG | 65 | 388 |
| 146951 | 3' UTR | 243 | 75192 | AATGCAAACCCATCATGAA | 43 | 389 |

As shown in Table 4, SEQ ID NOs, 322, 323, 324, 325, 326, 327, 328, 329, 330, 331, 332, 333, 334, 335, 337, 340, 341, 342, 343, 344, 345, 347, 349, 350, 351, 352, 353, 354, 355, 356, 357, 358, 360, 361, 362, 363, 364, 365, 366, 368, 369, 371, 372, 373, 374, 375, 377, 378, 380, 381, 384, 385, 386, 387, 388, and 389 demonstrated at least 40% inhibition of human PTP1B expression in this assay and are therefore preferred.

Example 24

Antisense Inhibition of PTP1B Expression (ISIS 113715) in Liver, Muscle and Adipose Tissue of the Cynomolgus Monkey In a further embodiment, male cynomolgus monkeys were treated with ISIS 113715 (SEQ ID NO: 166) and levels of PTP1B mRNA and protein were measured in muscle, adipose and liver tissue. Serum samples were also measured for insulin levels.

Male cynomolgus monkeys were divided into two treatment groups, control animals (n=4; saline treatment only) and treated animals (n=8; treated with ISIS 113715). All animals had two pre-dosing glucose tolerance tests (GTTs) performed to establish insulin and glucose baseline values. Animals in the treatment group were dosed subcutaneously on days 1, 8, and 15 with 3 mg/kg, 6 mg/kg and 12 mg/kg of ISIS 113715, respectively. Animals in the control group were untreated. All animals had GTTs performed on days 5, 13 and 19, four days post-dosing. Ten days after the last dose of 12 mg/kg, all animals in the treatment group (ISIS 113715) received a one-time dose of 6 mg/kg of ISIS 113715. Three days later, all animals were sacrificed and tissues were taken for analysis of PTP1B mRNA and protein levels. Levels of mRNA and protein were normalized to those of the saline treated animals. Of the tissue examined, PTP1B mRNA levels were reduced to the greatest extent in the fat and liver, being reduced by 41% and 40%, respectively. mRNA levels in muscle were reduced by 10%. Protein levels were reduced by 60% in the liver and by 45% in the muscle but were shown to increase by 10% in the fat.

Levels of the liver enzymes ALT and AST were measured weekly and showed no change, indicating no ongoing toxic effects of the oligonucleotide treatment.

The results of this study demonstrate a significant reduction in liver PTP1B mRNA and protein upon treatment with ISIS 113715. Furthermore, there was no change seen in the fasting insulin levels either between groups or between pre-treatment and post-treatment of the same group. There was, however, a significant lowering of insulin levels with no decrease in fasting glucose levels in all groups suggesting that insulin efficiency (sensitivity) was increased upon treatment with ISIS 113715.

Example 25

Effects of Antisense Inhibition of PTP1B (ISIS 113715) on mRNA Expression in Fractionated Liver Male db/db mice (age 9 weeks at time 0) were divided into matched groups (n=6) with the same average blood glucose levels and treated by intraperitoneal injection once a week with saline, ISIS 29848 (the control oligonucleotide) or ISIS 113715. db/db mice were treated at a dose of 50 mg/kg of ISIS 113715 or 50 mg/kg of ISIS 29848 or 100 mg/kg of ISIS 29848. Treatment was continued for 3 weeks after which the mice were sacrificed and tissues were collected for analysis. Liver tissue was removed and homogenized whole or fractionated into hepatocytes and non-parenchymal (NP) cell fractions by standard methods (Graham et al., *J. Pharmacol. Exp. Ther.*, 1998, 286, 447-458). During the study, plasma glucose levels were measured as were PTP1B mRNA levels in both cell fractions. RNA values were normalized and are expressed as a percentage of saline treated control.

Treatment of db/db mice with ISIS 113715 caused a significant reduction in plasma glucose levels (saline=500+/−25 vs. treated=223+/−21 mg/dL; p=0.0001).

ISIS 113715 successfully reduced PTP1B mRNA levels in both hepatocytes and NP cell fractions, with an 80% reduction in hepatocytes and a 30% reduction in the NP cell fraction. In addition, PTP1B expression in the two cell fractions was found to be dramatically different with a 5-8 fold greater level of expression being found in the NP fraction. Thus, the inability of ISIS 113715 to reduce PTP1B expression by no more than 60% in whole liver as seen in previous experiments may result from a combination of a relatively high expression of PTP1B in NP cells with a reduced ability of ISIS 113715 to inhibit expression in this same cell fraction. Consequently, distinct targeting of the compound to hepatocytes, the key metabolic cell type in liver, results in a much greater inhibition of PTP1B levels.

Example 26

Effects of Antisense Inhibition of PTP1B Expression (ISIS 113715) in the Obese Insulin-Resistant Hyperinsulinemic Rhesus Monkey-Improved Insulin Sensitivity In a further embodiment, male obese insulin-resistant hyperinsulinemic Rhesus monkeys were treated with ISIS 113715 (SEQ ID NO: 166) and insulin sensitivity, glucose tolerance and PTP1B mRNA and protein were measured. Serum samples were also measured for insulin levels.

Male rhesus monkeys were divided into two treatment groups, control animals (n=4; saline treatment only) and treated animals (n=8; treated with ISIS 113715). All animals had two pre-dosing glucose tolerance tests (GTTs) performed to establish insulin and glucose baseline values. Animals in the treatment group were dosed subcutaneously at a dose of 20 mg/kg (3 injections on alternate days the first week followed by one injection per week for the next two weeks). Fasted glucose/insulin levels and glucose tolerance (IVGTTs) were measured as pharmacologic endpoints.

As compared to baseline values, a 50% reduction in fasting insulin levels was observed (treated: 31±9 vs. baseline: 67±7 µU/mL, p=0.0001), which was not accompanied by any change in plasma glucose levels. Furthermore, a marked reduction in insulin levels (AUC) was observed after IVGTTs (treated: 7295±3178 vs. baseline: 18968±2113 µU-min/mL, p=0.0002). Insulin sensitivity was also significantly increased (glucose slope/insulin AUC; 5-20 minutes).

Hypoglycemia was not observed, even in the 16 hour-fasted animals. Levels of the liver enzymes ALT and AST were measured weekly and showed no change, indicating no ongoing toxic effects of the oligonucleotide treatment. Renal function tests were also normal.

The results of this study are consistent with those seen in previous rodent and monkey studies described herein which demonstrate a significant lowering of insulin levels suggesting that insulin efficiency (sensitivity) was increased upon treatment with ISIS 113715.

Example 27

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2'hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group, which has the following important properties. It is stable to the conditions of nucleoside phosphoramidite synthesis and oligonucleotide synthesis. However, after oligonucleotide synthesis the oligonucleotide is treated with methylamine, which not only cleaves the oligonucleotide from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis. Yet, when subsequently modified, it permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe, S. A., et al., *J. Am. Chem. Soc.*, 1998, 120, 11820-11821; Matteucci, M. D. and Caruthers, M. H. *J. Am. Chem. Soc.*, 1981, 103, 3185-3191; Beaucage, S. L. and Caruthers, M. H. *Tetrahedron Lett.*, 1981, 22, 1859-1862; Dahl, B. J., et al., *Acta Chem. Scand.*, 1990, 44, 639-641; Reddy, M. P., et al., *Tetrahedron Lett.*, 1994, 25, 4311-4314; Wincott, F. et al., *Nucleic Acids Res.*, 1995, 23, 2677-2684; Griffin, B. E., et al., *Tetrahedron*, 1967, 23, 2301-2313; Griffin, B. E., et al., *Tetrahedron*, 1967, 23, 2315-2331).

RNA antisense compounds (RNA oligonucleotides) of the present invention can be synthesized by the methods herein or purchased from Dharmacon Research, Inc (Lafayette, Colo.). Once synthesized, complementary RNA antisense compounds can then be annealed by methods known in the art to form double stranded (duplexed) antisense compounds. For example, duplexes can be formed by combining 30 µl of each of the complementary strands of RNA oligonucleotides (50 µM RNA oligonucleotide solution) and 15 µl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense compounds can be used in kits, assays, screens, or other methods to investigate the role of a target nucleic acid.

Example 28

Design and Screening of Duplexed Antisense Compounds Targeting PTP1B

In accordance with the present invention, a series of nucleic acid duplexes comprising the antisense compounds of the present invention and their complements can be designed to target PTP1B. The nucleobase sequence of the antisense strand of the duplex comprises at least a portion of an oligonucleotide in Table 1. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini.

For example, a duplex comprising an antisense strand having the sequence CGAGAGGCGGACGGGACCG (nucleotides 1-19 of SEQ ID NO: 414) and having a two-nucleobase overhang of deoxythymidine (dT) would have the following structure:

```
cgagaggcggacgggaccgTT  Antisense Strand (SEQ ID NO: 414)
||||||||||||||||||
TTgctctccgcctgccctggc         Complement (SEQ ID NO: 415)
```

The one or more nucleobases forming the single-stranded overhang(s) may be dT as shown or may be another modified or unmodified nucleobase.

A duplex comprising an antisense strand having the sequence CGAGAGGCGGACGGGACCG (nucleotides 1-19 of SEQ ID NO: 414) may also prepared with blunt ends (no single stranded overhang) as shown (antisense strand below is nucleotides 1-19 of SEQ ID NO: 414; complement below is nucleotides 1-19 of SEQ ID NO: 415):

```
cgagaggcggacgggaccg  Antisense Strand
|||||||||||||||||||
gctctccgcctgccctggc         Complement
```

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 μM. Once diluted, 30 μL of each strand is combined with 15 μL of a 5× solution of annealing buffer. The final concentration of said buffer is 100 mM potassium acetate, 30 mM HEPES-KOH pH 7.4, and 2 mM magnesium acetate. The final volume is 75¼. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 μM. This solution can be stored frozen (−20° C.) and freeze-thawed up to 5 times.

Once prepared, the duplexed antisense compounds are evaluated for their ability to modulate PTP1B expression. When cells reached 80% confluency, they are treated with duplexed antisense compounds of the invention. For cells grown in 96-well plates, wells are washed once with 200 μL OPTI-MEM™-1 reduced-serum medium (Gibco BRL) and then treated with 130 μL of OPTI-MEM™-1 medium containing 12 μg/mL LIPOFECTIN™ reagent (Gibco BRL) and the desired duplex antisense compound at a final concentration of 200 nM. After 5 hours of treatment, the medium is replaced with fresh medium. Cells are harvested 16 hours after treatment, at which time RNA is isolated and target reduction measured by RT-PCR.

A series of siRNA duplexes were prepared as described above and were tested in A549 cells for their ability to reduce human PTP1b expression. Also tested for comparison were several single-stranded 2'-MOE gapped (chimeric) oligonucleotides as well as two single-stranded controls (ISIS 116847, targeted to PTEN, and ISIS 129700, a scrambled control) and two RNA duplex unrelated controls (ISIS 271783:ISIS 297802 duplex and ISIS 263188:263189 duplex), which are targeted to PTEN. These compounds were tested at two concentrations, 75 nM and 150 nM. The results are shown in Table 5.

TABLE 5

Inhibition of human PTP1B expression by siRNA duplexes

| Isis No. anti-sense: sense | Antisense strand sequence | Anti-sense strand SEQ ID NO | Sense Strand SEQ ID NO | Target site on SEQ ID NO: 3 | % Inhib 75 nM | % Inhib 150 nM | Chem-istry[1] |
|---|---|---|---|---|---|---|---|
| 348290: 348274 | UUCAUGUCGGAUAUCCUGGdTdA | 390 | 403 | 148 | 53 | 70 | R |
| 348291: 348275 | UCACUGGCUUCAUGUCGGAdTdA | 391 | 404 | 156 | 0 | 12 | R |
| 348292: 348276 | GGUAAGAAUGUAACUCCUUdTdG | 392 | 405 | 322 | 8 | 9 | R |
| 348293: 348277 | CUUCAGAGAUCAAUGUUAAdTdT | 393 | 406 | 512 | 0 | 28 | R |
| 348294: 348278 | UAGCUGUCGCACUGUAUAAdTdA | 394 | 407 | 544 | 44 | 52 | R |
| 348295: 348279 | CCAAUUCUAGCUGUCGCACdTdG | 395 | 408 | 551 | 67 | 79 | R |
| 342914: 342934 | UUGAUAAAGCCCUUGAUGCA | 396 | 409 | 1884 | 66 | 80 | R |
| 342916: 342936 | GGUCAUGCACAGGCAGGUUG | 397 | 410 | 2274 | 55 | 72 | R |
| 342908: 342928 | GAAGAAGGGUCUUUCCUCUU | 398 | 411 | 799 | 61 | 77 | R |
| 107772 | CCCGGACTTGTCGATCTGCT | 20 | N/A | 113 | 76 | 90 | G |
| 107804 | CAGTGTCTTGACTCATGCTT | 52 | N/A | 1176 | 85 | 95 | G |

TABLE 5-continued

Inhibition of human PTP1B expression by siRNA duplexes

| Isis No. antisense: sense | Antisense strand sequence | Anti-sense strand SEQ ID NO | Sense Strand SEQ ID NO | Target site on SEQ ID NO: 3 | % Inhib7 5 nM | % Inhib7 150 nM | Chem-istry[1] |
|---|---|---|---|---|---|---|---|
| 107813 | CCGCGGCATGCCTGCTAGTC | 61 | N/A | 1460 | 71 | 88 | G |
| 107831 | GGTCATGCACAGGCAGGTTG | 79 | N/A | 2274 | 83 | 88 | G |
| 116847 | CTGCTAGCCTCTGGATTTGA | 399 | N/A | N/A | 0 | 0 | G |
| 129700 | TAGTGCGGACCTACCCACGA | 400 | N/A | N/A | 17 | 13 | G |
| 271783: 297802 | GGGACGAACUGGUGUAAUGdTdT | 401 | 412 | N/A | 0 | 4 | R |
| 263188: 263189 | CUUCUGGCAUCCGGUUUAGdTdT | 402 | 413 | N/A | 28 | 9 | R |

[1]Chemistry:
"R" indicates an RNA duplex in which both strands are 2' ribonucleic acid, except where 2' deoxynucleotides are indicated by a "d" preceding the base. All linkages are P = S.
"G" indicates a single-stranded 2' MOE gapmer in which nucleotides 1-5 and 16-20 are 2' MOE nucleotides and nucleotides 6-15 are 2'-deoxy. All linkages are P = S and all cytosines are 5-methylcytosines.

As can be seen from the data in Table 5, both siRNA duplexes 25 and single stranded 2'MOE gapped oligonucleotides inhibit human PTP1b target expression in a dose-dependent manner.

What is claimed is:

1. A chimeric antisense oligonucleotide 20 to 50 nucleobases in length targeted to a nucleic acid molecule encoding PTP1B (SEQ ID NO: 3 or 243), wherein said oligonucleotide comprises the sequence selected from the group consisting of SEQ ID NO: 244, 245, 247, 248, 249, 250, 251, 252, 254, 255, 256, 257, 258, 259, 260, 261, 262, 263, 267, 268, 269, 271, 275, 276, 277, 278, 279, 281, 282, 283, 288, 290, 291, 292, 294, 296, 297, 298, 299, 300, 302, 303, 307, 310, 311, 313, 317, 318, 322, 323, 324, 325, 326, 327, 328, 329, 330, 331, 332, 333, 334, 340, 342, 347, 349, 350, 352, 353, 354, 355, 356, 357, 360, 361, 362, 363, 364, 365, 366, 368, 369, 371, 372, 374, 377, 378, 380, 381, and 388 wherein said oligonucleotide specifically hybridizes with said nucleic acid molecule encoding PTP and inhibits the expression of human PTP1B.

2. The oligonucleotide of claim 1, which comprises at least one modified internucleoside linkage.

3. The oligonucleotide of claim 2 wherein the modified internucleoside linkage is a phosphorothioate linkage.

4. The oligonucleotide of claim 1, which comprises at least one modified sugar moiety.

5. The oligonucleotide of claim 1, which comprises at least one modified nucleobase.

6. A composition comprising the oligonucleotide of claim 1 and a pharmaceutically acceptable carrier, diluent, enhancer or excipient.

7. A method of inhibiting the expression of PTP1B in cells or tissues comprising contacting said cells or tissues with the oligonucleotide of claim 1 so that expression of PTP1B is inhibited.

8. The oligonucleotide of claim 4, wherein the at least one modified sugar moiety is a 2'-O-methoxyethyl sugar moiety.

9. The oligonucleotide of claim 5, wherein the at least one modified nucleobase is a 5-methylcytosine.

10. The method of claim 7, wherein the cells or tissues are human cells or tissues.

11. A method of treating a disease or condition associated with PTP1B in an animal with the oligonucleotide of claim 1, wherein the disease or condition is selected from a metabolic disease or condition, diabetes, Type 2 diabetes, obesity, and hyperlipidemia.

12. The method of claim 11, wherein the animal is a human.

13. The method of claim 11, wherein the oligonucleotide decreases blood glucose levels in the animal.

14. The method of claim 13, wherein the animal is a diabetic animal.

15. A method of preventing or delaying the onset of a disease or condition associated with PTP1B in an animal with the oligonucleotide of claim 1, wherein the disease or condition is selected from a metabolic disease or condition, diabetes, Type 2 diabetes, obesity, and hyperlipidemia.

16. The method of claim 15, wherein the animal is human.

17. The method of claim 15, wherein treatment with the oligonucleotide prevents or delays the onset of an increase in blood glucose levels in an animal.

18. The method of claim 17, wherein the animal is a diabetic animal.

* * * * *

UNITED STATES PATENT AND TRADEMARK OFFICE
CERTIFICATE OF CORRECTION

PATENT NO. : 8,853,178 B2
APPLICATION NO. : 13/177462
DATED : October 7, 2014
INVENTOR(S) : Sanjay Bhanot It is certified that error appears in the above-identified patent and that said Letters Patent is hereby corrected as shown below:

Title page
   (Item 74, Attorney) at line 2, Change "Patent Dept. Knobbe Martens" to --Patent Dept.; Knobbe, Martens, Olson & Bear, LLP--.
   In column 1 (page 2, item 56) at line 10, References Cited Under Other Publications, change "transolcation" to --translocation--.
   In column 1 (page 2, item 56) at line 25, References Cited Under Other Publications, change "rosigitazone," to --rosiglitazone,--.
   In column 1 (page 2, item 56) at line 48, References Cited Under Other Publications, change "ceullular" to --cellular--.
   In column 1 (page 3, item 56) at line 23, References Cited Under Other Publications, change "P13-Kinase" to --P13-kinase--.
   In column 1 (page 3, item 56) at line 34, References Cited Under Other Publications, change "insuliun" to --insulin--.
   In column 2 (page 3, item 56) at line 21, References Cited Under Other Publications, change "phsphatase" to --phosphatase--.

In the Specification
   In column 1 at line 16, Change "12/046,721" to --12/046,421--.
   In column 1 at line 26, Change "BIOL0001 USC4SEQ.txt," to --BIOL0001USC4SEQ.txt,--.
   In column 2 at line 11, Change "PTP1B-/- mice" to --PTP1B -/- mice--.
   In column 2 at line 32, Change "PT1B" to --PTP1B--.
   In column 4 at line 5, Change "408" to --408.--.
   In column 10 at line 23, Change "regimes" to --regimens--.

Signed and Sealed this
Eighth Day of September, 2015

Michelle K. Lee
*Director of the United States Patent and Trademark Office*

CERTIFICATE OF CORRECTION (continued)

U.S. Pat. No. 8,853,178 B2

In column 14 at line 32, Change "hexyl-5-tritylthiol" to --hexyl-S-tritylthiol--.

In column 14 at line 36, Change "dodecandiol" to --dodecanediol--.

In column 18 at lines 57-58, Change "heterogenous" to --heterogeneous--.

In column 24 at line 41, Change "Ilium" to --Illum--.

In column 24 at line 57, Change "131B1" to --131 B1--.

In column 26 at lines 49-50, Change "acylcholines," to --acetylcholines,--.

In column 28 at line 15, Change "polycytidic" to --polycytidylic--.

In column 29 at line 35, Change "ribivirin," to --ribavirin,--.

In column 31 at line 10, Change "5'-DMT-3' phosphoramidites." to --5'-DMT-3'-phosphoramidites.--.

In column 31 at lines 17-18, Change "5'-DMT-3' phosphoramidites." to --5'-DMT-3'-phosphoramidites.--.

In column 32 at line 4 (approx.), Change "2'O-Methoxyethyl" to --2'-O-methoxyethyl--.

In column 34 at line 57 (approx.), Change "phthaliamidoxy" to --phthalimidoxy--.

In column 36 at line 30, Change "tetrazonide" to --tetrazolide--.

In column 37 at line 5, Change "2-N-isobutyryl-6-O- diphenylcarbamoyl" to --2-N-isobutyryl-6-O-diphenylcarbamoyl--.

In column 37 at line 9 (approx.), Change "phosphitylated" to --phosphorylated--.

In column 39 at line 65, Change "[2'-deoxy]-[-2'-O-" to --[2'-deoxy]-[2'-O- --.

In column 40 at line 8 (approx.), Change "2-Methoxyethyl Phosphodiester" to --2-Methoxyethyl)Phosphodiester--.

In column 40 at line 9 (approx.), Change "2'-O-(methoxyethyl)phosphodiester" to --2'-O-(2-Methoxyethyl)Phosphodiester--.

In column 42 at line 43, Change "200 µl," to --200 µL--.

In column 42 at line 44, Change "130 µl" to --130 µL--.

In column 44 at line 28, Change "200 µl" to --200 µL--.

In column 44 at line 64, Change "60 µl," to --60 µL--.

In column 46 at line 32, Change "5'JOE-" to --5' JOE- --.

In column 48 at line 12 (approx.), Change "(T-MOE)" to --(2'-MOE)--.

In column 61 at line 41, Change "SEQ ID NO:" to --SEQ ID NO: 10--.

In column 77 at line 30, Change "754." to --75 µL.--.

In columns 79-80 at line 17 (approx., Table 5-Continued), Change "2' MOE" to --2'-MOE--.

In columns 79-80 at line 17 (approx., Table 5-Continued), Change "2' MOE" to --2'-MOE--.

In column 79 at line 27, Change "PTP1b" to --PTP1B--.

In the Claims

In column 283 at line 28, In Claim 1, change "PTP" to --PTP1B--.

SEQUENCE LISTING

<160> NUMBER OF SEQ ID NOS: 415

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 1
tccgtcatcg ctcctcaggg                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 2
atgcattctg cccccaagga                                              20

<210> SEQ ID NO 3
<211> LENGTH: 3247
<212> TYPE: DNA
<213> ORGANISM: Homo sapiens
<220> FEATURE:
<221> NAME/KEY: CDS
<222> LOCATION: (91)...(1398)

<400> SEQUENCE: 3
gggcgggcct cggggctaag agcgcgacgc ctagagcggc agacggcgca gtgggccgag    60
aaggaggcgc agcagccgcc ctggcccgtc  atg gag atg gaa aag gag ttc gag   114
                                  Met Glu Met Glu Lys Glu Phe Glu
                                   1               5 cag atc gac aag tcc ggg agc tgg gcg gcc att tac cag gat atc cga   162

```
                Gln Ile Asp Lys Ser Gly Ser Trp Ala Ala Ile Tyr Gln Asp Ile Arg
                     10                  15                  20 cat gaa gcc agt gac ttc cca tgt aga gtg gcc aag ctt cct aag aac        210
His Glu Ala Ser Asp Phe Pro Cys Arg Val Ala Lys Leu Pro Lys Asn
 25                  30                  35                  40 aaa aac cga aat agg tac aga gac gtc agt ccc ttt gac cat agt cgg        258
Lys Asn Arg Asn Arg Tyr Arg Asp Val Ser Pro Phe Asp His Ser Arg
                     45                  50                  55 att aaa cta cat caa gaa gat aat gac tat atc aac gct agt ttg ata        306
Ile Lys Leu His Gln Glu Asp Asn Asp Tyr Ile Asn Ala Ser Leu Ile
                 60                  65                  70 aaa atg gaa gaa gcc caa agg agt tac att ctt acc cag ggc cct ttg        354
Lys Met Glu Glu Ala Gln Arg Ser Tyr Ile Leu Thr Gln Gly Pro Leu
             75                  80                  85 cct aac aca tgc ggt cac ttt tgg gag atg gtg tgg gag cag aaa agc        402
Pro Asn Thr Cys Gly His Phe Trp Glu Met Val Trp Glu Gln Lys Ser
         90                  95                  100 agg ggt gtc gtc atg ctc aac aga gtg atg gag aaa ggt tcg tta aaa        450
Arg Gly Val Val Met Leu Asn Arg Val Met Glu Lys Gly Ser Leu Lys
105                 110                 115                 120 tgc gca caa tac tgg cca caa aaa gaa gaa aaa gag atg atc ttt gaa        498
Cys Ala Gln Tyr Trp Pro Gln Lys Glu Glu Lys Glu Met Ile Phe Glu
                    125                 130                 135 gac aca aat ttg aaa tta aca ttg atc tct gaa gat atc aag tca tat        546
Asp Thr Asn Leu Lys Leu Thr Leu Ile Ser Glu Asp Ile Lys Ser Tyr
                140                 145                 150 tat aca gtg cga cag cta gaa ttg gaa aac ctt aca acc caa gaa act        594
Tyr Thr Val Arg Gln Leu Glu Leu Glu Asn Leu Thr Thr Gln Glu Thr
            155                 160                 165 cga gag atc tta cat ttc cac tat acc aca tgg cct gac ttt gga gtc        642
Arg Glu Ile Leu His Phe His Tyr Thr Thr Trp Pro Asp Phe Gly Val
170                 175                 180 cct gaa tca cca gcc tca ttc ttg aac ttt ctt ttc aaa gtc cga gag        690
Pro Glu Ser Pro Ala Ser Phe Leu Asn Phe Leu Phe Lys Val Arg Glu
185                 190                 195                 200 tca ggg tca ctc agc ccg gag cac ggg ccc gtt gtg gtg cac tgc agt        738
Ser Gly Ser Leu Ser Pro Glu His Gly Pro Val Val Val His Cys Ser
                    205                 210                 215 gca ggc atc ggc agg tct gga acc ttc tgt ctg gct gat acc tgc ctc        786
Ala Gly Ile Gly Arg Ser Gly Thr Phe Cys Leu Ala Asp Thr Cys Leu
                220                 225                 230 ctg ctg atg gac aag agg aaa gac cct tct tcc gtt gat atc aag aaa        834
Leu Leu Met Asp Lys Arg Lys Asp Pro Ser Ser Val Asp Ile Lys Lys
            235                 240                 245 gtg ctg tta gaa atg agg aag ttt cgg atg ggg ttg atc cag aca gcc        882
Val Leu Leu Glu Met Arg Lys Phe Arg Met Gly Leu Ile Gln Thr Ala
250                 255                 260 gac cag ctg cgc ttc tcc tac ctg gct gtg atc gaa ggt gcc aaa ttc        930
Asp Gln Leu Arg Phe Ser Tyr Leu Ala Val Ile Glu Gly Ala Lys Phe
265                 270                 275                 280 atc atg ggg gac tct tcc gtg cag gat cag tgg aag gag ctt tcc cac        978
Ile Met Gly Asp Ser Ser Val Gln Asp Gln Trp Lys Glu Leu Ser His
                    285                 290                 295 gag gac ctg gag ccc cca ccc gag cat atc ccc cca cct ccc cgg cca       1026
Glu Asp Leu Glu Pro Pro Pro Glu His Ile Pro Pro Pro Pro Arg Pro
                300                 305                 310 ccc aaa cga atc ctg gag cca cac aat ggg aaa tgc agg gag ttc ttc       1074
Pro Lys Arg Ile Leu Glu Pro His Asn Gly Lys Cys Arg Glu Phe Phe
            315                 320                 325
```

```
cca aat cac cag tgg gtg aag gaa gag acc cag gag gat aaa gac tgc    1122
Pro Asn His Gln Trp Val Lys Glu Glu Thr Gln Glu Asp Lys Asp Cys
        330                 335                 340 ccc atc aag gaa gaa aaa gga agc ccc tta aat gcc gca ccc tac ggc    1170
Pro Ile Lys Glu Glu Lys Gly Ser Pro Leu Asn Ala Ala Pro Tyr Gly
345                 350                 355                 360 atc gaa agc atg agt caa gac act gaa gtt aga agt cgg gtc gtg ggg    1218
Ile Glu Ser Met Ser Gln Asp Thr Glu Val Arg Ser Arg Val Val Gly
                365                 370                 375 gga agt ctt cga ggt gcc cag gct gcc tcc cca gcc aaa ggg gag ccg    1266
Gly Ser Leu Arg Gly Ala Gln Ala Ala Ser Pro Ala Lys Gly Glu Pro
            380                 385                 390 tca ctg ccc gag aag gac gag gac cat gca ctg agt tac tgg aag ccc    1314
Ser Leu Pro Glu Lys Asp Glu Asp His Ala Leu Ser Tyr Trp Lys Pro
                395                 400                 405 ttc ctg gtc aac atg tgc gtg gct acg gtc ctc acg gcc ggc gct tac    1362
Phe Leu Val Asn Met Cys Val Ala Thr Val Leu Thr Ala Gly Ala Tyr
410                 415                 420 ctc tgc tac agg ttc ctg ttc aac agc aac aca tag cctgaccctc         1408
Leu Cys Tyr Arg Phe Leu Phe Asn Ser Asn Thr
425                 430                 435 ctccactcca cctccaccca ctgtccgcct ctgcccgcag agcccacgcc cgactagcag  1468
gcatgccgcg gtaggtaagg gccgccggac cgcgtagaga gccgggcccc ggacggacgt  1528
tggttctgca ctaaaaccca tcttccccgg atgtgtgtct caccccctcat ccttttactt  1588
tttgcccctt ccactttgag taccaaatcc acaagccatt ttttgaggag agtgaaagag  1648
agtaccatgc tggcggcgca gagggaaggg gcctacaccc gtcttgggc tcgccccacc   1708
cagggctccc tcctggagca tcccaggcgg cgcacgccaa cagcccccc cttgaatctg   1768
cagggagcaa ctctccactc catatttatt taaacaattt ttttccccaaa ggcatccata  1828
gtgcactagc attttcttga accaataatg tattaaaatt ttttgatgtc agccttgcat  1888
caagggcttt atcaaaaagt acaataataa atcctcaggt agtactggga atggaaggct  1948
ttgccatggg cctgctgcgt cagaccagta ctgggaagga ggacggttgt aagcagttgt  2008
tatttagtga tattgtgggt aacgtgagaa gatagaacaa tgctataata tataatgaac  2068
acgtgggtat ttaataagaa acatgatgtg agattacttt gtcccgctta ttctcctccc  2128
tgttatctgc tagatctagt tctcaatcac tgctcccccg tgtgtattag aatgcatgta  2188
aggtcttctt gtgtcctgat gaaaaatatg tgcttgaaat gagaaacttt gatctctgct  2248
tactaatgtg ccccatgtcc aagtccaacc tgcctgtgca tgacctgatc attacatggc  2308
tgtggttcct aagcctgttg ctgaagtcat tgtcgctcag caatagggtg cagttttcca  2368
ggaataggca tttgctaatt cctggcatga cactctagtg acttcctggt gaggcccagc  2428
ctgtcctggt acagcagggt cttgctgtaa ctcagacatt ccaagggtat gggaagccat  2488
attcacacct cacgctctgg acatgattta gggaagcagg gacacccccc gccccccacc  2548
tttgggatca gcctccgcca ttccaagtca acactcttct tgagcagacc gtgatttgga  2608
agagaggcac ctgctggaaa ccacacttct tgaaacagcc tgggtgacgg tcctttaggc  2668
agcctgccgc cgtctctgtc ccggttcacc ttgccgagag aggcgcgtct gccccaccct  2728
caaaccctgt ggggcctgat ggtgctcacg actcttcctg caaagggaac tgaagacctc  2788
cacattaagt ggctttttaa catgaaaaac acggcagctg tagctcccga gctactctct  2848
tgccagcatt ttcacatttt gcctttctcg tggtagaagc cagtacagag aaattctgtg  2908
gtgggaacat tcgaggtgtc accctgcaga gctatggtga ggtgtggata aggcttaggt  2968
```

```
gccaggctgt aagcattctg agctggcttg ttgtttttaa gtcctgtata tgtatgtagt    3028
agtttgggtg tgtatatata gtagcatttc aaaatggacg tactggttta acctcctatc    3088
cttggagagc agctggctct ccaccttgtt acacattatg ttagagaggt agcgagctgc    3148
tctgctatat gccttaagcc aatatttact catcaggtca ttatttttta caatggccat    3208
ggaataaacc atttttacaa aaataaaaac aaaaaaagc                           3247

<210> SEQ ID NO 4
<211> LENGTH: 21
<212> TYPE: DNA
<213> ORGANISM: Artificial Sequence
<220> FEATURE:
<223> OTHER INFORMATION: PCR Primer

<400> SEQUENCE: 4
ggagttcgag cagatcgaca a                                               21

<210> SEQ ID NO 5
<211> LENGTH: 21
<212> TYPE: DNA
<213> ORGANISM: Artificial Sequence
<220> FEATURE:
<223> OTHER INFORMATION: PCR Primer

<400> SEQUENCE: 5
ggccactcta catgggaagt c                                               21

<210> SEQ ID NO 6
<211> LENGTH: 24
<212> TYPE: DNA
<213> ORGANISM: Artificial Sequence
<220> FEATURE:
<223> OTHER INFORMATION: PCR Probe

<400> SEQUENCE: 6
agctgggcgg ccatttacca ggat                                            24

<210> SEQ ID NO 7
<211> LENGTH: 19
<212> TYPE: DNA
<213> ORGANISM: Artificial Sequence
<220> FEATURE:
<223> OTHER INFORMATION: PCR Primer

<400> SEQUENCE: 7
gaaggtgaag gtcggagtc                                                  19

<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8
gaagatggtg atgggatttc                                                 20

<210> SEQ ID NO 9
<211> LENGTH: 20
<212> TYPE: DNA
<213> ORGANISM: Artificial Sequence
<220> FEATURE:
<223> OTHER INFORMATION: PCR Probe
```

```
<400> SEQUENCE: 9
caagcttccc gttctcagcc                                               20

<210> SEQ ID NO 10
<211> LENGTH: 4127
<212> TYPE: DNA
<213> ORGANISM: Rattus norvegicus
<220> FEATURE:
<221> NAME/KEY: CDS
<222> LOCATION: (120)...(1418)

<400> SEQUENCE: 10
agccgctgct ggggaggttg gggctgaggt ggtggcgggc gacgggcctc gagacgcgga   60
gcgacgcggc ctagcgcggc ggacggccga gggaactcgg gcagtcgtcc cgtcccgcc   119 atg gaa atg gag aag gaa ttc gag cag atc gat aag gct ggg aac tgg   167
Met Glu Met Glu Lys Glu Phe Glu Gln Ile Asp Lys Ala Gly Asn Trp
 1               5                  10                  15 gcg gct att tac cag gat att cga cat gaa gcc agt gac ttc cca tgc   215
Ala Ala Ile Tyr Gln Asp Ile Arg His Glu Ala Ser Asp Phe Pro Cys
             20                  25                  30 aga ata gcg aaa ctt cct aag aac aaa aac cgg aac agg tac cga gat   263
Arg Ile Ala Lys Leu Pro Lys Asn Lys Asn Arg Asn Arg Tyr Arg Asp
         35                  40                  45 gtc agc cct ttt gac cac agt cgg att aaa ttg cat cag gaa gat aat   311
Val Ser Pro Phe Asp His Ser Arg Ile Lys Leu His Gln Glu Asp Asn
     50                  55                  60 gac tat atc aat gcc agc ttg ata aaa atg gag gaa gcc cag agg agc   359
Asp Tyr Ile Asn Ala Ser Leu Ile Lys Met Glu Glu Ala Gln Arg Ser
 65                  70                  75                  80 tat atc ctc acc cag ggc cct tta cca aac acg tgc ggg cac ttc tgg   407
Tyr Ile Leu Thr Gln Gly Pro Leu Pro Asn Thr Cys Gly His Phe Trp
                 85                  90                  95 gag atg gtg tgg gag cag aag agc agg ggc gtg gtc atg ctc aac cgc   455
Glu Met Val Trp Glu Gln Lys Ser Arg Gly Val Val Met Leu Asn Arg
            100                 105                 110 atc atg gag aaa ggc tcg tta aaa tgt gcc cag tat tgg cca cag aaa   503
Ile Met Glu Lys Gly Ser Leu Lys Cys Ala Gln Tyr Trp Pro Gln Lys
        115                 120                 125 gaa gaa aaa gag atg gtc ttc gat gac acc aat ttg aag ctg aca ctg   551
Glu Glu Lys Glu Met Val Phe Asp Asp Thr Asn Leu Lys Leu Thr Leu
    130                 135                 140 atc tct gaa gat gtc aag tca tat tac aca gta cgg cag ttg gag ttg   599
Ile Ser Glu Asp Val Lys Ser Tyr Tyr Thr Val Arg Gln Leu Glu Leu
145                 150                 155                 160 gag aac ctg gct acc cag gag gct cga gag atc ctg cat ttc cac tac   647
Glu Asn Leu Ala Thr Gln Glu Ala Arg Glu Ile Leu His Phe His Tyr
                165                 170                 175 acc acc tgg cct gac ttt gga gtc cct gag tca cct gcc tct ttc ctc   695
Thr Thr Trp Pro Asp Phe Gly Val Pro Glu Ser Pro Ala Ser Phe Leu
            180                 185                 190 aat ttc cta ttc aaa gtc cga gag tca ggc tca ctc agc cca gag cac   743
Asn Phe Leu Phe Lys Val Arg Glu Ser Gly Ser Leu Ser Pro Glu His
        195                 200                 205 ggc ccc att gtg gtc cac tgc agt gct ggc att ggc agg tca ggg acc   791
Gly Pro Ile Val Val His Cys Ser Ala Gly Ile Gly Arg Ser Gly Thr
    210                 215                 220 ttc tgc ctg gct gac acc tgc ctc tta ctg atg gac aag agg aaa gac   839
Phe Cys Leu Ala Asp Thr Cys Leu Leu Leu Met Asp Lys Arg Lys Asp
225                 230                 235                 240
```

| | | |
|---|---|---|
| ccg tcc tct gtg gac atc aag aaa gtg ctg ttg gag atg cgc agg ttc<br>Pro Ser Ser Val Asp Ile Lys Lys Val Leu Leu Glu Met Arg Arg Phe<br>245 250 255 | | 887 |
| cgc atg ggg ctc atc cag acg gcc gac caa ctg cgc ttc tcc tac ctg<br>Arg Met Gly Leu Ile Gln Thr Ala Asp Gln Leu Arg Phe Ser Tyr Leu<br>260 265 270 | | 935 |
| gct gtg atc gag ggt gca aag ttc atc atg ggc gac tcg tca gtg cag<br>Ala Val Ile Glu Gly Ala Lys Phe Ile Met Gly Asp Ser Ser Val Gln<br>275 280 285 | | 983 |
| gat cag tgg aag gag ctt tcc cat gaa gac ctg gag cct ccc cct gag<br>Asp Gln Trp Lys Glu Leu Ser His Glu Asp Leu Glu Pro Pro Pro Glu<br>290 295 300 | | 1031 |
| cac gtg ccc cca cct ccc cgg cca ccc aaa cgc aca ttg gag cct cac<br>His Val Pro Pro Pro Pro Arg Pro Pro Lys Arg Thr Leu Glu Pro His<br>305 310 315 320 | | 1079 |
| aat ggc aag tgc aag gag ctc ttc tcc aac cac cag tgg gtg agc gag<br>Asn Gly Lys Cys Lys Glu Leu Phe Ser Asn His Gln Trp Val Ser Glu<br>325 330 335 | | 1127 |
| gag agc tgt gag gat gag gac atc ctg gcc aga gag gaa agc aga gcc<br>Glu Ser Cys Glu Asp Glu Asp Ile Leu Ala Arg Glu Glu Ser Arg Ala<br>340 345 350 | | 1175 |
| ccc tca att gct gtg cac agc atg agc agt atg agt caa gac act gaa<br>Pro Ser Ile Ala Val His Ser Met Ser Ser Met Ser Gln Asp Thr Glu<br>355 360 365 | | 1223 |
| gtt agg aaa cgg atg gtg ggt gga ggt ctt caa agt gct cag gca tct<br>Val Arg Lys Arg Met Val Gly Gly Gly Leu Gln Ser Ala Gln Ala Ser<br>370 375 380 | | 1271 |
| gtc ccc act gag gaa gag ctg tcc cca acc gag gag gaa caa aag gca<br>Val Pro Thr Glu Glu Glu Leu Ser Pro Thr Glu Glu Glu Gln Lys Ala<br>385 390 395 400 | | 1319 |
| cac agg cca gtt cac tgg aag ccc ttc ctg gtc aac gtg tgc atg gcc<br>His Arg Pro Val His Trp Lys Pro Phe Leu Val Asn Val Cys Met Ala<br>405 410 415 | | 1367 |
| acg gcc ctg gcg act ggc gcg tac ctc tgt tac cgg gta tgt ttt cac<br>Thr Ala Leu Ala Thr Gly Ala Tyr Leu Cys Tyr Arg Val Cys Phe His<br>420 425 430 | | 1415 |
| tga cagactgctg tgaggcatga gcgtggtggg cgctgccact gcccaggtta | | 1468 |
| ggatttggtc tgcggcgtct aacctggtgt agaagaaaca acagcttaca agcctgtggt | | 1528 |
| ggaactggaa gggccagccc caggaggggc atctgtgcac tgggctttga aggagcccct | | 1588 |
| ggtcccaaga acagagtcta atctcagggc cttaacctgt tcaggagaag tagaggaaat | | 1648 |
| gccaaatact cttcttgctc tcacctcact cctcccctt ctctggttcg tttgtttttg | | 1708 |
| gaaaaaaaa aaaagaatt acaacacatt gttgtttta acatttataa aggcaggttt | | 1768 |
| ttgttatttt tagagaaaac aaaagatgct aggcactggt gagattctct tgtgcccttt | | 1828 |
| ggcatgtgat cagattcacg atttacgttt atttccgggg gagggtccca cctgtcagga | | 1888 |
| ctgtaaagtt cctgctggct tggtcagccc cccaccccc ccaccccgag cttgcaggtg | | 1948 |
| ccctgctgtg aggagagcag cagcagaggc tgccctgga cagaagccca gctctgcttc | | 2008 |
| cctcaggtgt ccctgcgttt ccatcctcct tctttgtgac cgccatcttg cagatgaccc | | 2068 |
| agtcctcagc accccacccc tgcagatggg tttctccgag gcctgcctc agggtcatca | | 2128 |
| gaggttggct gccagcttag agctggggct tccatttgat tggaaagtca ttactattct | | 2188 |
| atgtagaagc cactccactg aggtgtaaag caagactcat aaaggaggag ccttggtgtc | | 2248 |
| atggaagtca ctccgcgcgc aggacctgta acaacctctg aaacactcag tcctgctgca | | 2308 |
| gtgacgtcct tgaaggcatc agacagatga tttgcagact gccaagactt gtcctgagcc | | 2368 |

```
gtgattttta gagtctggac tcatgaaaca ccgccgagcg cttactgtgc agcctctgat    2428
gctggttggc tgaggctgcg gggaggtgga cactgtgggt gcatccagtg cagttgcttt    2488
tgtgcagttg ggtccagcag cacagcccgc actccagcct cagctgcagg ccacagtggc    2548
catggaggcc gccagagcga gctggggtgg atgcttgttc acttggagca gccttcccag    2608
gacgtgcagc tcccttcctg ctttgtcctt ctgcttcctt ccctggagta gcaagcccac    2668
gagcaatcgt gaggggtgtg agggagctgc agaggcatca gagtggcctg cagcggcgtg    2728
aggccccttc ccctccgaca ccccctcca gaggagccgc tccactgtta tttattcact    2788
ttgcccacag acacccctga gtgagcacac cctgaaactg accgtgtaag gtgtcagcct    2848
gcacccagga ccgtcaggtg cagcaccggg tcagtcctag ggttgaggta ggactgacac    2908
agccactgtg tggctggtgc tggggcaggg gcaggagctg agggtcttag aagcaatctt    2968
caggaacaga caacagtggt gacatgtaaa gtccctgtgg ctactgatga catgtgtagg    3028
atgaaggctg gcctttctcc catgactttc tagatcccgt tccccgtctg ctttccctgt    3088
gagttagaaa acacacaggc tcctgtcctg gtggtgccgt gtgcttgaca tgggaaactt    3148
agatgcctgc tcactggcgg gcacctcggc atcgccacca ctcagagtga gagcagtgct    3208
gtccagtgcc gaggccgcct gactcccggc aggactcttc aggctctggc ctgccccagc    3268 acacccgct ggatctcaga cattccacac ccacacctca ttccctggac acttgggcaa    3328
gcaggcccgc ccttccacct ctggggtcag cccctccatt ccgagttcac actgctctgg    3388
agcaggccag gaccggaagc aaggcagctg gtgaggagca ccctcctggg aacagtgtag    3448
gtgacagtcc tgagagtcag cttgctagcg ctgctggcac cagtcacctt gctcagaagt    3508
gtgtggctct tgaggctgaa gagactgatg atggtgctca tgactcttct gtgaggggaa    3568
cttgaccttc acattgggtg gcttttttta aaataagcga aggcagctgg aactccagtc    3628
tgcctcttgc cagcacttca cattttgcct ttcacccaga gaagccagca cagagccact    3688
ggggaaggcg atggccttgc ctgcacaggc tgaggagatg gctcagccgg cgtccaggct    3748
gtgtctggag caggggtgc acagcagcct cacaggtggg ggcctcagag caggcgctgc    3808
cctgtcccct gccccgctgg aggcagcaaa gctgctgcat gccttaagtc aatacttact    3868
cagcagggcg ctctcgttct ctctctctct ctctctctct ctctctctct ctctctctct    3928
ctctctaaat ggccatagaa taaaccattt tacaaaaata aaagccaaca acaaagtgct    3988
ctggaatagc acctttgcag gagcggggg tgtctcaggg tcttctgtga cctcaccgaa    4048
ctgtccgact gcaccgtttc caacttgtgt ctcactaatg ggtctgcatt agttgcaaca    4108
ataaatgttt ttaaagaac                                                4127
```

<210> SEQ ID NO 11
<211> LENGTH: 21
<212> TYPE: DNA
<213> ORGANISM: Artificial Sequence
<220> FEATURE:
<223> OTHER INFORMATION: PCR Primer

<400> SEQUENCE: 11
cgagggtgca aagttcatca t                                               21

<210> SEQ ID NO 12
<211> LENGTH: 21
<212> TYPE: DNA
<213> ORGANISM: Artificial Sequence
<220> FEATURE:

<223> OTHER INFORMATION: PCR Primer

<400> SEQUENCE: 12
ccaggtcttc atgggaaagc t                                              21

<210> SEQ ID NO 13
<211> LENGTH: 26
<212> TYPE: DNA
<213> ORGANISM: Artificial Sequence
<220> FEATURE:
<223> OTHER INFORMATION: PCR Probe

<400> SEQUENCE: 13
cgactcgtca gtgcaggatc agtgga                                         26

<210> SEQ ID NO 14
<211> LENGTH: 23
<212> TYPE: DNA
<213> ORGANISM: Artificial Sequence
<220> FEATURE:
<223> OTHER INFORMATION: PCR Primer

<400> SEQUENCE: 14
tgttctagag acagccgcat ctt                                            23

<210> SEQ ID NO 15
<211> LENGTH: 21
<212> TYPE: DNA
<213> ORGANISM: Artificial Sequence
<220> FEATURE:
<223> OTHER INFORMATION: PCR Primer

<400> SEQUENCE: 15
caccgacctt caccatcttg t                                              21

<210> SEQ ID NO 16
<211> LENGTH: 24
<212> TYPE: DNA
<213> ORGANISM: Artificial Sequence
<220> FEATURE:
<223> OTHER INFORMATION: PCR Probe

<400> SEQUENCE: 16
ttgtgcagtg ccagcctcgt ctca                                           24

<210> SEQ ID NO 17
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 17
cttagccccg aggcccgccc                                                20

<210> SEQ ID NO 18
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 18
ctcggcccac tgcgccgtct                                                20

```
<210> SEQ ID NO 19
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 19
catgacgggc cagggcggct                                                     20

<210> SEQ ID NO 20
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 20
cccggacttg tcgatctgct                                                     20

<210> SEQ ID NO 21
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 21
ctggcttcat gtcggatatc                                                     20

<210> SEQ ID NO 22
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 22
ttggccactc tacatgggaa                                                     20

<210> SEQ ID NO 23
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 23
ggactgacgt ctctgtacct                                                     20

<210> SEQ ID NO 24
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 24
gatgtagttt aatccgacta                                                     20

<210> SEQ ID NO 25
<211> LENGTH: 20
<212> TYPE: DNA
<213> ORGANISM: Artificial Sequence
<220> FEATURE:
<223> OTHER INFORMATION: Synthetic Oligonucleotide
```

```
<400> SEQUENCE: 25
ctagcgttga tatagtcatt                                              20

<210> SEQ ID NO 26
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 26
gggtaagaat gtaactcctt                                              20

<210> SEQ ID NO 27
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 27
tgaccgcatg tgttaggcaa                                              20

<210> SEQ ID NO 28
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 28
ttttctgctc ccacaccatc                                              20

<210> SEQ ID NO 29
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 29
ctctgttgag catgacgaca                                              20

<210> SEQ ID NO 30
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 30
gcgcatttta acgaaccttt                                              20

<210> SEQ ID NO 31
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 31
aaatttgtgt cttcaaagat                                              20

<210> SEQ ID NO 32
<211> LENGTH: 20
```

```
<212> TYPE: DNA
<213> ORGANISM: Artificial Sequence
<220> FEATURE:
<223> OTHER INFORMATION: Synthetic Oligonucleotide

<400> SEQUENCE: 32
tgatatcttc agagatcaat                                              20

<210> SEQ ID NO 33
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 33
tctagctgtc gcactgtata                                              20

<210> SEQ ID NO 34
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 34
agtttcttgg gttgtaaggt                                              20

<210> SEQ ID NO 35
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 35
gtggtatagt ggaaatgtaa                                              20

<210> SEQ ID NO 36
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 36
tgattcaggg actccaaagt                                              20

<210> SEQ ID NO 37
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 37
ttgaaaagaa agttcaagaa                                              20

<210> SEQ ID NO 38
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 38
```

```
gggctgagtg accctgactc                                              20

<210> SEQ ID NO 39
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 39
gcagtgcacc acaacgggcc                                              20

<210> SEQ ID NO 40
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 40
aggttccaga cctgccgatg                                              20

<210> SEQ ID NO 41
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 41
agcaggaggc aggtatcagc                                              20

<210> SEQ ID NO 42
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 42
gaagaagggt ctttcctctt                                              20

<210> SEQ ID NO 43
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 43
tctaacagca ctttcttgat                                              20

<210> SEQ ID NO 44
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 44
atcaacccca tccgaaactt                                              20

<210> SEQ ID NO 45
<211> LENGTH: 20
<212> TYPE: DNA
<213> ORGANISM: Artificial Sequence
```

```
<220> FEATURE:
<223> OTHER INFORMATION: Synthetic Oligonucleotide

<400> SEQUENCE: 45
gagaagcgca gctggtcggc                                               20

<210> SEQ ID NO 46
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 46
tttggcacct tcgatcacag                                               20

<210> SEQ ID NO 47
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 47
agctccttcc actgatcctg                                               20

<210> SEQ ID NO 48
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 48
tccaggattc gtttgggtgg                                               20

<210> SEQ ID NO 49
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 49
gaactccctg catttcccat                                               20

<210> SEQ ID NO 50
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 50
ttccttcacc cactggtgat                                               20

<210> SEQ ID NO 51
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 51
gtagggtgcg gcatttaagg                                               20
```

<210> SEQ ID NO 52
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 52
cagtgtcttg actcatgctt                                              20

<210> SEQ ID NO 53
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 53
gcctgggcac ctcgaagact                                              20

<210> SEQ ID NO 54
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 54
ctcgtccttc tcgggcagtg                                              20

<210> SEQ ID NO 55
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 55
gggcttccag taactcagtg                                              20

<210> SEQ ID NO 56
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 56
ccgtagccac gcacatgttg                                              20

<210> SEQ ID NO 57
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 57
tagcagaggt aagcgccggc                                              20

<210> SEQ ID NO 58
<211> LENGTH: 20
<212> TYPE: DNA
<213> ORGANISM: Artificial Sequence
<220> FEATURE:
<223> OTHER INFORMATION: Synthetic Oligonucleotide

```
<400> SEQUENCE: 58
ctatgtgttg ctgttgaaca                                          20

<210> SEQ ID NO 59
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 59
ggaggtggag tggaggaggg                                          20

<210> SEQ ID NO 60
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 60
ggctctgcgg gcagaggcgg                                          20

<210> SEQ ID NO 61
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 61
ccgcggcatg cctgctagtc                                          20

<210> SEQ ID NO 62
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 62
tctctacgcg gtccggcggc                                          20

<210> SEQ ID NO 63
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 63
aagatgggtt ttagtgcaga                                          20

<210> SEQ ID NO 64
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 64
gtactctctt tcactctcct                                          20

<210> SEQ ID NO 65
```

```
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 65
ggccccttcc ctctgcgccg                                              20

<210> SEQ ID NO 66
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 66
ctccaggagg gagccctggg                                              20

<210> SEQ ID NO 67
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 67
gggctgttgg cgtgcgccgc                                              20

<210> SEQ ID NO 68
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 68
tttaaataaa tatggagtgg                                              20

<210> SEQ ID NO 69
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 69
gttcaagaaa atgctagtgc                                              20

<210> SEQ ID NO 70
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 70
ttgataaagc ccttgatgca                                              20

<210> SEQ ID NO 71
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 71
```

| | |
|---|---|
| atggcaaagc cttccattcc | 20 |

<210> SEQ ID NO 72
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 72

| | |
|---|---|
| gtcctccttc ccagtactgg | 20 |

<210> SEQ ID NO 73
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 73

| | |
|---|---|
| ttacccacaa tatcactaaa | 20 |

<210> SEQ ID NO 74
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 74

| | |
|---|---|
| attatatatt atagcattgt | 20 |

<210> SEQ ID NO 75
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 75

| | |
|---|---|
| tcacatcatg tttcttatta | 20 |

<210> SEQ ID NO 76
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 76

| | |
|---|---|
| ataacaggga ggagaataag | 20 |

<210> SEQ ID NO 77
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 77

| | |
|---|---|
| ttacatgcat tctaatacac | 20 |

<210> SEQ ID NO 78
<211> LENGTH: 20
<212> TYPE: DNA

<213> ORGANISM: Artificial Sequence
<220> FEATURE:
<223> OTHER INFORMATION: Synthetic Oligonucleotide

<400> SEQUENCE: 78
gatcaaagtt tctcatttca                                               20

<210> SEQ ID NO 79
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 79
ggtcatgcac aggcaggttg                                               20

<210> SEQ ID NO 80
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 80
caacaggctt aggaaccaca                                               20

<210> SEQ ID NO 81
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 81
aactgcaccc tattgctgag                                               20

<210> SEQ ID NO 82
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 82
gtcatgccag gaattagcaa                                               20

<210> SEQ ID NO 83
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 83
acaggctggg cctcaccagg                                               20

<210> SEQ ID NO 84
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 84
tgagttacag caagaccctg                                               20

```
<210> SEQ ID NO 85
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 85
gaatatggct tcccataccc                                                  20

<210> SEQ ID NO 86
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 86
ccctaaatca tgtccagagc                                                  20

<210> SEQ ID NO 87
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 87
gacttggaat ggcggaggct                                                  20

<210> SEQ ID NO 88
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 88
caaatcacgg tctgctcaag                                                  20

<210> SEQ ID NO 89
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 89
gaagtgtggt ttccagcagg                                                  20

<210> SEQ ID NO 90
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 90
cctaaaggac cgtcacccag                                                  20

<210> SEQ ID NO 91
<211> LENGTH: 20
<212> TYPE: DNA
<213> ORGANISM: Artificial Sequence
<220> FEATURE:
```

<223> OTHER INFORMATION: Synthetic Oligonucleotide

<400> SEQUENCE: 91
gtgaaccggg acagagacgg                    20

<210> SEQ ID NO 92
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 92
gccccacagg gtttgagggt                    20

<210> SEQ ID NO 93
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 93
cctttgcagg aagagtcgtg                    20

<210> SEQ ID NO 94
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 94
aaagccactt aatgtggagg                    20

<210> SEQ ID NO 95
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 95
gtgaaaatgc tggcaagaga                    20

<210> SEQ ID NO 96
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 96
tcagaatgct tacagcctgg                    20

<210> SEQ ID NO 97
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 97
caacctcccc agcagcggct                    20

```
<210> SEQ ID NO 98
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 98
tcgaggcccg tcgcccgcca                                               20

<210> SEQ ID NO 99
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 99
cctcggccgt ccgccgcgct                                               20

<210> SEQ ID NO 100
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 100
tcgatctgct cgaattcctt                                               20

<210> SEQ ID NO 101
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 101
cctggtaaat agccgcccag                                               20

<210> SEQ ID NO 102
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 102
tgtcgaatat cctggtaaat                                               20

<210> SEQ ID NO 103
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 103
actggcttca tgtcgaatat                                               20

<210> SEQ ID NO 104
<211> LENGTH: 20
<212> TYPE: DNA
<213> ORGANISM: Artificial Sequence
<220> FEATURE:
<223> OTHER INFORMATION: Synthetic Oligonucleotide
```

<400> SEQUENCE: 104
aagtcactgg cttcatgtcg                                               20

<210> SEQ ID NO 105
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 105
gaagtcactg gcttcatgtc                                               20

<210> SEQ ID NO 106
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 106
ggaagtcact ggcttcatgt                                               20

<210> SEQ ID NO 107
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 107
gggaagtcac tggcttcatg                                               20

<210> SEQ ID NO 108
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 108
tgggaagtca ctggcttcat                                               20

<210> SEQ ID NO 109
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 109
atgggaagtc actggcttca                                               20

<210> SEQ ID NO 110
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 110
catgggaagt cactggcttc                                               20

<210> SEQ ID NO 111
<211> LENGTH: 20

-continued

<210> SEQ ID NO 111
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 111
tttttgttct taggaagttt                                        20

<210> SEQ ID NO 112
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 112
cggtttttgt tcttaggaag                                        20

<210> SEQ ID NO 113
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 113
tccgactgtg gtcaaaaggg                                        20

<210> SEQ ID NO 114
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 114
ttaatccgac tgtggtcaaa                                        20

<210> SEQ ID NO 115
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 115
atagtcatta tcttcctgat                                        20

<210> SEQ ID NO 116
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 116
ttgatatagt cattatcttc                                        20

<210> SEQ ID NO 117
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 117

```
gcttcctcca tttttatcaa                                              20

<210> SEQ ID NO 118
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 118
ggccctgggt gaggatatag                                              20

<210> SEQ ID NO 119
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 119
cacaccatct cccagaagtg                                              20

<210> SEQ ID NO 120
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 120
tgctcccaca ccatctccca                                              20

<210> SEQ ID NO 121
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 121
ctgctcccac accatctccc                                              20

<210> SEQ ID NO 122
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 122
tctgctccca caccatctcc                                              20

<210> SEQ ID NO 123
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 123
ttctgctccc acaccatctc                                              20

<210> SEQ ID NO 124
<211> LENGTH: 20
<212> TYPE: DNA
<213> ORGANISM: Artificial Sequence
```

```
<220> FEATURE:
<223> OTHER INFORMATION: Synthetic Oligonucleotide

<400> SEQUENCE: 124
cccctgctct tctgctccca                                               20

<210> SEQ ID NO 125
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 125
atgcggttga gcatgaccac                                               20

<210> SEQ ID NO 126
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 126
tttaacgagc ctttctccat                                               20

<210> SEQ ID NO 127
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 127
ttttcttctt tctgtggcca                                               20

<210> SEQ ID NO 128
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 128
gaccatctct ttttcttctt                                               20

<210> SEQ ID NO 129
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 129
tcagagatca gtgtcagctt                                               20

<210> SEQ ID NO 130
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 130
cttgacatct tcagagatca                                               20
```

```
<210> SEQ ID NO 131
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 131
taatatgact tgacatcttc                                               20

<210> SEQ ID NO 132
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 132
aactccaact gccgtactgt                                               20

<210> SEQ ID NO 133
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 133
tctctcgagc ctcctgggta                                               20

<210> SEQ ID NO 134
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 134
ccaaagtcag gccaggtggt                                               20

<210> SEQ ID NO 135
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 135
gggactccaa agtcaggcca                                               20

<210> SEQ ID NO 136
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 136
agggactcca aagtcaggcc                                               20

<210> SEQ ID NO 137
<211> LENGTH: 20
<212> TYPE: DNA
<213> ORGANISM: Artificial Sequence
<220> FEATURE:
<223> OTHER INFORMATION: Synthetic Oligonucleotide
```

<400> SEQUENCE: 137
cagggactcc aaagtcaggc							20

<210> SEQ ID NO 138
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 138
tcagggactc caaagtcagg							20

<210> SEQ ID NO 139
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 139
ggtgactcag ggactccaaa							20

<210> SEQ ID NO 140
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 140
cctgactctc ggactttgaa							20

<210> SEQ ID NO 141
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 141
gctgagtgag cctgactctc							20

<210> SEQ ID NO 142
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 142
ccgtgctctg ggctgagtga							20

<210> SEQ ID NO 143
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 143
aaggtccctg acctgccaat							20

<210> SEQ ID NO 144

```
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 144
tctttcctct tgtccatcag                                               20

<210> SEQ ID NO 145
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 145
gtctttcctc ttgtccatca                                               20

<210> SEQ ID NO 146
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 146
ggtctttcct cttgtccatc                                               20

<210> SEQ ID NO 147
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 147
gggtctttcc tcttgtccat                                               20

<210> SEQ ID NO 148
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 148
aacagcactt tcttgatgtc                                               20

<210> SEQ ID NO 149
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 149
ggaacctgcg catctccaac                                               20

<210> SEQ ID NO 150
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 150
```
tggtcggccg tctggatgag                                            20

<210> SEQ ID NO 151
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 151
gagaagcgca gttggtcggc                                            20

<210> SEQ ID NO 152
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 152
aggtaggaga agcgcagttg                                            20

<210> SEQ ID NO 153
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 153
gccaggtagg agaagcgcag                                            20

<210> SEQ ID NO 154
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 154
agccaggtag gagaagcgca                                            20

<210> SEQ ID NO 155
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 155
cagccaggta ggagaagcgc                                            20

<210> SEQ ID NO 156
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 156
acagccaggt aggagaagcg                                            20

<210> SEQ ID NO 157
<211> LENGTH: 20
<212> TYPE: DNA

```
<213> ORGANISM: Artificial Sequence
<220> FEATURE:
<223> OTHER INFORMATION: Synthetic Oligonucleotide

<400> SEQUENCE: 157
cacagccagg taggagaagc                                                    20

<210> SEQ ID NO 158
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 158
tcacagccag gtaggagaag                                                    20

<210> SEQ ID NO 159
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 159
atcacagcca ggtaggagaa                                                    20

<210> SEQ ID NO 160
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 160
gatcacagcc aggtaggaga                                                    20

<210> SEQ ID NO 161
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 161
cgatcacagc caggtaggag                                                    20

<210> SEQ ID NO 162
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 162
tcgatcacag ccaggtagga                                                    20

<210> SEQ ID NO 163
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 163
caccctcgat cacagccagg                                                    20
```

```
<210> SEQ ID NO 164
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 164
tccttccact gatcctgcac                                              20

<210> SEQ ID NO 165
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 165
ctccttccac tgatcctgca                                              20

<210> SEQ ID NO 166
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 166
gctccttcca ctgatcctgc                                              20

<210> SEQ ID NO 167
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 167
agctccttcc actgatcctg                                              20

<210> SEQ ID NO 168
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 168
aagctccttc cactgatcct                                              20

<210> SEQ ID NO 169
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 169
aaagctcctt ccactgatcc                                              20

<210> SEQ ID NO 170
<211> LENGTH: 20
<212> TYPE: DNA
<213> ORGANISM: Artificial Sequence
<220> FEATURE:
```

<223> OTHER INFORMATION: Synthetic Oligonucleotide

<400> SEQUENCE: 170
gaaagctcct tccactgatc                                              20

<210> SEQ ID NO 171
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 171
ggaaagctcc ttccactgat                                              20

<210> SEQ ID NO 172
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 172
gggaaagctc cttccactga                                              20

<210> SEQ ID NO 173
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 173
tgggaaagct ccttccactg                                              20

<210> SEQ ID NO 174
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 174
tggccgggga ggtgggggca                                              20

<210> SEQ ID NO 175
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 175
tgggtggccg gggaggtggg                                              20

<210> SEQ ID NO 176
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 176
tgcgtttggg tggccgggga                                              20

```
<210> SEQ ID NO 177
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 177
tgcacttgcc attgtgaggc                                               20

<210> SEQ ID NO 178
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 178
acttcagtgt cttgactcat                                               20

<210> SEQ ID NO 179
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 179
aacttcagtg tcttgactca                                               20

<210> SEQ ID NO 180
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 180
taacttcagt gtcttgactc                                               20

<210> SEQ ID NO 181
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 181
ctaacttcag tgtcttgact                                               20

<210> SEQ ID NO 182
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 182
gacagatgcc tgagcacttt                                               20

<210> SEQ ID NO 183
<211> LENGTH: 20
<212> TYPE: DNA
<213> ORGANISM: Artificial Sequence
<220> FEATURE:
<223> OTHER INFORMATION: Synthetic Oligonucleotide
```

<400> SEQUENCE: 183
gaccaggaag ggcttccagt                                               20

<210> SEQ ID NO 184
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 184
tgaccaggaa gggcttccag                                               20

<210> SEQ ID NO 185
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 185
ttgaccagga agggcttcca                                               20

<210> SEQ ID NO 186
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 186
gttgaccagg aagggcttcc                                               20

<210> SEQ ID NO 187
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 187
gcacacgttg accaggaagg                                               20

<210> SEQ ID NO 188
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 188
gaggtacgcg ccagtcgcca                                               20

<210> SEQ ID NO 189
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 189
tacccggtaa cagaggtacg                                               20

<210> SEQ ID NO 190
<211> LENGTH: 20

```
<212> TYPE: DNA
<213> ORGANISM: Artificial Sequence
<220> FEATURE:
<223> OTHER INFORMATION: Synthetic Oligonucleotide

<400> SEQUENCE: 190
agtgaaaaca tacccggtaa                                          20

<210> SEQ ID NO 191
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 191
caaatcctaa cctgggcagt                                          20

<210> SEQ ID NO 192
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 192
ttccagttcc accacaggct                                          20

<210> SEQ ID NO 193
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 193
ccagtgcaca gatgcccctc                                          20

<210> SEQ ID NO 194
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 194
acaggttaag gccctgagat                                          20

<210> SEQ ID NO 195
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 195
gcctagcatc ttttgttttc                                          20

<210> SEQ ID NO 196
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 196
```
aagccagcag gaactttaca                                              20

<210> SEQ ID NO 197
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 197
gggacacctg agggaagcag                                              20

<210> SEQ ID NO 198
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 198
ggtcatctgc aagatggcgg                                              20

<210> SEQ ID NO 199
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 199
gccaacctct gatgaccctg                                              20

<210> SEQ ID NO 200
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 200
tggaagcccc agctctaagc                                              20

<210> SEQ ID NO 201
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 201
tagtaatgac tttccaatca                                              20

<210> SEQ ID NO 202
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 202
tgagtcttgc tttacacctc                                              20

<210> SEQ ID NO 203
<211> LENGTH: 20
<212> TYPE: DNA
<213> ORGANISM: Artificial Sequence

```
<220> FEATURE:
<223> OTHER INFORMATION: Synthetic Oligonucleotide

<400> SEQUENCE: 203
cctgcgcgcg gagtgacttc                                                   20

<210> SEQ ID NO 204
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 204
aggacgtcac tgcagcagga                                                   20

<210> SEQ ID NO 205
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 205
tcaggacaag tcttggcagt                                                   20

<210> SEQ ID NO 206
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 206
gaggctgcac agtaagcgct                                                   20

<210> SEQ ID NO 207
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 207
tcagccaacc agcatcagag                                                   20

<210> SEQ ID NO 208
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 208
acccacagtg tccacctccc                                                   20

<210> SEQ ID NO 209
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 209
agtgcgggct gtgctgctgg                                                   20
```

<210> SEQ ID NO 210
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 210
cagctcgctc tggcggcctc                                                  20

<210> SEQ ID NO 211
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 211
aggaagggag ctgcacgtcc                                                  20

<210> SEQ ID NO 212
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 212
ccctcacgat tgctcgtggg                                                  20

<210> SEQ ID NO 213
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 213
cagtggagcg gctcctctgg                                                  20

<210> SEQ ID NO 214
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 214
caggctgaca ccttacacgg                                                  20

<210> SEQ ID NO 215
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 215
gtcctacctc aaccctagga                                                  20

<210> SEQ ID NO 216
<211> LENGTH: 20
<212> TYPE: DNA
<213> ORGANISM: Artificial Sequence
<220> FEATURE:
<223> OTHER INFORMATION: Synthetic Oligonucleotide

```
<400> SEQUENCE: 216
ctgccccagc accagccaca                                               20

<210> SEQ ID NO 217
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 217
attgcttcta agaccctcag                                               20

<210> SEQ ID NO 218
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 218
ttacatgtca ccactgttgt                                               20

<210> SEQ ID NO 219
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 219
tacacatgtc atcagtagcc                                               20

<210> SEQ ID NO 220
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 220 tttttctaact cacagggaaa                                              20

<210> SEQ ID NO 221
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 221
gtgcccgcca gtgagcaggc                                               20

<210> SEQ ID NO 222
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 222
cggcctcggc actggacagc                                               20

<210> SEQ ID NO 223
```

```
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 223
gtggaatgtc tgagatccag                                               20

<210> SEQ ID NO 224
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 224
agggcgggcc tgcttgccca                                               20

<210> SEQ ID NO 225
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 225
cggtcctggc ctgctccaga                                               20

<210> SEQ ID NO 226
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 226
tacactgttc ccaggagggt                                               20

<210> SEQ ID NO 227
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 227
tggtgccagc agcgctagca                                               20

<210> SEQ ID NO 228
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 228
cagtctcttc agcctcaaga                                               20

<210> SEQ ID NO 229
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 229
```
aagagtcatg agcaccatca                                         20

<210> SEQ ID NO 230
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 230
tgaaggtcaa gttcccctca                                         20

<210> SEQ ID NO 231
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 231
ctggcaagag gcagactgga                                         20

<210> SEQ ID NO 232
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 232
ggctctgtgc tggcttctct                                         20

<210> SEQ ID NO 233
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 233
gccatctcct cagcctgtgc                                         20

<210> SEQ ID NO 234
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 234
agcgcctgct ctgaggcccc                                         20

<210> SEQ ID NO 235
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 235
tgctgagtaa gtattgactt                                         20

<210> SEQ ID NO 236
<211> LENGTH: 20
<212> TYPE: DNA

```
<213> ORGANISM: Artificial Sequence
<220> FEATURE:
<223> OTHER INFORMATION: Synthetic Oligonucleotide

<400> SEQUENCE: 236
ctatggccat ttagagagag                                                     20

<210> SEQ ID NO 237
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 237
tggtttattc tatggccatt                                                     20

<210> SEQ ID NO 238
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 238
cgctcctgca aaggtgctat                                                     20

<210> SEQ ID NO 239
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 239
gttggaaacg gtgcagtcgg                                                     20

<210> SEQ ID NO 240
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 240
atttattgtt gcaactaatg                                                     20

<210> SEQ ID NO 241
<211> LENGTH: 2346
<212> TYPE: DNA
<213> ORGANISM: Mus musculus
<220> FEATURE:
<221> NAME/KEY: CDS
<222> LOCATION: (710)...(2008)

<400> SEQUENCE: 241
gaattcggga tccttttgca cattcctagt tagcagtgca tactcatcag actggagatg         60
tttaatgaca tcagggaacc aaacggacaa cccatagtac ccgaagacag ggtgaaccag        120
acaatcgtaa gcttgatggt gttttccctg actgggtagt tgaagcatct catgaatgtc        180
agccaaattc cgtacagttc ggtgcggatc cgaacgaaac acctcctgta ccaggttccc        240
gtgtcgctct caatttcaat cagctcatct atttgtttgg gagtcttgat tttatttacc        300
gtgaagacct tctctggctg gccccgggct ctcatgttgg tgtcatgaat taacttcaga        360
```

-continued

```
atcatccagg cttcatcatg ttttcccacc tccagcaaga accgagggct ttctggcatg        420
aaggtgagag ccaccacaga ggagacgcat gggagcgcac agacgatgac gaagacgcgc        480
cacgtgtgga actggtaggc tgaacccatg ctgaagctcc acccgtagtg gggaatgatg        540
gcccaggcat ggcggaggct agatgccgcc aatcatccag aacatgcaga agccgctgct        600
ggggagcttg gggctgcggt ggtggcgggt gacgggcttc gggacgcgga gcgacgcggc        660
ctagcgcggc ggacggccgt gggaactcgg gcagccgacc cgtcccgcc atg gag atg      718
                                                    Met Glu Met
                                                     1 gag aag gag ttc gag gag atc gac aag gct ggg aac tgg gcg gct att        766
Glu Lys Glu Phe Glu Glu Ile Asp Lys Ala Gly Asn Trp Ala Ala Ile
      5                  10                  15 tac cag gac att cga cat gaa gcc agc gac ttc cca tgc aaa gtc gcg        814
Tyr Gln Asp Ile Arg His Glu Ala Ser Asp Phe Pro Cys Lys Val Ala
 20                  25                  30                  35 aag ctt cct aag aac aaa aac cgg aac agg tac cga gat gtc agc cct        862
Lys Leu Pro Lys Asn Lys Asn Arg Asn Arg Tyr Arg Asp Val Ser Pro
                 40                  45                  50 ttt gac cac agt cgg att aaa ttg cac cag gaa gat aat gac tat atc        910
Phe Asp His Ser Arg Ile Lys Leu His Gln Glu Asp Asn Asp Tyr Ile
         55                  60                  65 aat gcc agc ttg ata aaa atg gaa gaa gcc cag agg agc tat att ctc        958
Asn Ala Ser Leu Ile Lys Met Glu Glu Ala Gln Arg Ser Tyr Ile Leu
     70                  75                  80 acc cag ggc cct tta cca aac aca tgt ggg cac ttc tgg gag atg gtg       1006
Thr Gln Gly Pro Leu Pro Asn Thr Cys Gly His Phe Trp Glu Met Val
 85                  90                  95 tgg gag cag aag agc agg ggc gtg gtc atg ctc aac cgc atc atg gag       1054
Trp Glu Gln Lys Ser Arg Gly Val Val Met Leu Asn Arg Ile Met Glu
100                 105                 110                 115 aaa ggc tcg tta aaa tgt gcc cag tat tgg cca cag caa gaa gaa aag       1102
Lys Gly Ser Leu Lys Cys Ala Gln Tyr Trp Pro Gln Gln Glu Glu Lys
                120                 125                 130 gag atg gtc ttt gat gac aca ggt ttg aag ttg aca cta atc tct gaa       1150
Glu Met Val Phe Asp Asp Thr Gly Leu Lys Leu Thr Leu Ile Ser Glu
            135                 140                 145 gat gtc aag tca tat tac aca gta cga cag ttg gag ttg gaa aac ctg       1198
Asp Val Lys Ser Tyr Tyr Thr Val Arg Gln Leu Glu Leu Glu Asn Leu
        150                 155                 160 act acc aag gag act cga gag atc ctg cat ttc cac tac acc aca tgg       1246
Thr Thr Lys Glu Thr Arg Glu Ile Leu His Phe His Tyr Thr Thr Trp
    165                 170                 175 cct gac ttt gga gtc ccc gag tca ccg gct tct ttc ctc aat ttc ctt       1294
Pro Asp Phe Gly Val Pro Glu Ser Pro Ala Ser Phe Leu Asn Phe Leu
180                 185                 190                 195 ttc aaa gtc cga gag tca ggc tca ctc agc ctg gag cat ggc ccc att       1342
Phe Lys Val Arg Glu Ser Gly Ser Leu Ser Leu Glu His Gly Pro Ile
                200                 205                 210 gtg gtc cac tgc agc gcc ggc atc ggg agg tca ggg acc ttc tgt ctg       1390
Val Val His Cys Ser Ala Gly Ile Gly Arg Ser Gly Thr Phe Cys Leu
            215                 220                 225 gct gac acc tgc ctc tta ctg atg gac aag agg aaa gac cca tct tcc       1438
Ala Asp Thr Cys Leu Leu Leu Met Asp Lys Arg Lys Asp Pro Ser Ser
        230                 235                 240 gtg gac atc aag aaa gta ctg ctg gag atg cgc agg ttc cgc atg ggg       1486
Val Asp Ile Lys Lys Val Leu Leu Glu Met Arg Arg Phe Arg Met Gly
    245                 250                 255 ctc atc cag act gcc gac cag ctg cgc ttc tcc tac ctg gct gtc atc       1534
Leu Ile Gln Thr Ala Asp Gln Leu Arg Phe Ser Tyr Leu Ala Val Ile
```

```
                Leu Ile Gln Thr Ala Asp Gln Leu Arg Phe Ser Tyr Leu Ala Val Ile
                260                 265                 270                 275 gag ggc gcc aag ttc atc atg ggc gac tcg tca gtg cag gat cag tgg                1582
Glu Gly Ala Lys Phe Ile Met Gly Asp Ser Ser Val Gln Asp Gln Trp
                280                 285                 290 aag gag ctc tcc cgg gag gat cta gac ctt cca ccc gag cac gtg ccc                1630
Lys Glu Leu Ser Arg Glu Asp Leu Asp Leu Pro Pro Glu His Val Pro
                295                 300                 305 cca cct ccc cgg cca ccc aaa cgc aca ctg gag cct cac aac ggg aag                1678
Pro Pro Pro Arg Pro Pro Lys Arg Thr Leu Glu Pro His Asn Gly Lys
            310                 315                 320 tgc aag gag ctc ttc tcc agc cac cag tgg gtg agc gag gag acc tgt                1726
Cys Lys Glu Leu Phe Ser Ser His Gln Trp Val Ser Glu Glu Thr Cys
        325                 330                 335 ggg gat gaa gac agc ctg gcc aga gag gaa ggc aga gcc cag tca agt                1774
Gly Asp Glu Asp Ser Leu Ala Arg Glu Glu Gly Arg Ala Gln Ser Ser
340                 345                 350                 355 gcc atg cac agc gtg agc agc atg agt cca gac act gaa gtt agg aga                1822
Ala Met His Ser Val Ser Ser Met Ser Pro Asp Thr Glu Val Arg Arg
                360                 365                 370 cgg atg gtg ggt gga ggt ctt caa agt gct cag gcg tct gtc ccc acc                1870
Arg Met Val Gly Gly Gly Leu Gln Ser Ala Gln Ala Ser Val Pro Thr
                375                 380                 385 gag gaa gag ctg tcc tcc act gag gag gaa cac aag gca cat tgg cca                1918
Glu Glu Glu Leu Ser Ser Thr Glu Glu Glu His Lys Ala His Trp Pro
            390                 395                 400 agt cac tgg aag ccc ttc ctg gtc aat gtg tgc atg gcc acg ctc ctg                1966
Ser His Trp Lys Pro Phe Leu Val Asn Val Cys Met Ala Thr Leu Leu
        405                 410                 415 gcc acc ggc gcg tac ttg tgc tac cgg gtg tgt ttt cac tga                        2008
Ala Thr Gly Ala Tyr Leu Cys Tyr Arg Val Cys Phe His
420                 425                 430 cagactggga ggcactgcca ctgcccagct taggatgcgg tctgcggcgt ctgacctggt              2068
gtagagggaa caacaactcg caagcctgct ctggaactgg aagggcctgc cccaggaggg              2128
tattagtgca ctgggctttg aaggagcccc tggtcccacg aacagagtct aatctcaggg              2188
ccttaacctg ttcaggagaa gtagaggaaa tgccaaatac tcttcttgct ctcacctcac              2248
tcctccccct tctctgattc atttgttttt ggaaaaaaaa aaaaaagaa ttacaacaca               2308 ttgttgtttt taacatttat aaaggcaggc ccgaattc                                      2346

<210> SEQ ID NO 242
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: n = a, t, c, or g
<220> FEATURE:
<223> OTHER INFORMATION: Synthetic Oligonucleotide

<400> SEQUENCE: 242
nnnnnnnnnn nnnnnnnnnn                                                          20

<210> SEQ ID NO 243
<211> LENGTH: 75899
<212> TYPE: DNA
<213> ORGANISM: Homo sapiens
<220> FEATURE:

<400> SEQUENCE: 243
```

```
gatcttcctg cctcagcctc cccagcagct gggccccacc acaccggcta atttttaac      60 tttagtagt gacgaggtct gattctgtta cccaggctgg tctggaactc ctggcctcaa     120
gacatccgcc tgcctctgcc tcccaaagtg ctgggattac agatgtaagc caccgcgcct   180
gggctcctat gatttttatt taacataatg caccatggaa tttgtgctct gcttagttca   240
gtctgagcag gagttccttg atacttcggg aaacactgaa atcattcca tccccatcca    300 ttcattcctg cagcacccaa gtggaaattc tgcgtttcag acaggacac tacccttaga    360 gagcagtggg cttccccagc agcgtagtga acatgatac tcctgagttt catgaaaaaa   420
gggcagacat ctggccagag ctgggaggca ggaaatagag cacggtgccc tcctcccata   480
ctccagcttg gattactgag gctggggccc aggccctgca ggaaaggagg tgcatgacta   540
ctttaaggcc actcactctg tgactcaacg ggccgggtcg ggctggaac tcaatgccct    600 cccgggcctg gagagcccac gcgccgtggg cggggctccc ggggtcgcct aggcaacagg   660
cgcgcgccgc gcccgagccc agagcccaa agcggaggag ggaacgcgcg ctattagata   720
tctcgcggtg ctggggccac ttcccctagc accgccccg gctcctcccc gcggaagtgc    780
ttgtcgaaat tctcgatcgc tgattggtcc ttctgcttca ggggcggagc ccctggcagg   840
cgtgatgcgt agttccggct gccggttgac atgaagaagc agcagcggct agggcggcgg   900
tagctgcagg ggtcggggat tgcagcgggc ctcggggcta agagcgcgac gcggcctaga   960
gcggcagacg gcgcagtggg ccgagaagga ggcgcagcag ccgccctggc ccgtcatgga  1020
gatggaaaag gagttcgagc agatcgacaa gtccgggagc tgggcggcca tttaccaggt  1080
gcgggagcgc cccggagcgt ggcgggccct tcgcttaggc cgcttgaaca tcccctcaga  1140
cctccaggcc ccagactccc tctgggtctt gccctctgcc tcgctcctac tgcttgagga  1200
ttcgatggga cagcgacgca ctgcgtcccc ccacccttg tccccggggc gggcgtgttt    1260
ctcgccgcag cgtcggagcc cccttcgatc ccccacctcc cttctgttct ccagctcggg  1320
tgatctctca agccggggga ccgccggtct gtgctctcaa cgcgaatccc tcgcaccccg   1380
accccgcccc ctgcctgtcc actctttgtc ccctggggtg atttagcacc cccactattt   1440
ccttttctgg agtggaccac ctcagactct cttcctttgt ctccctgggg gaaaaggtta   1500
ctccccccgt ccctccttca catttccttt cccctagtct cagtgtgcgt cgagtcccag   1560
agatgacagt cccctttccc ctttctgttc attcatttat tggataggag ttggcaagct  1620
tattctgtgc taggcaccgc ttaggcattg gaggtggtgt ttgctaatca ggacaggcaa   1680
gatcctagcc ttagtggggc ctagagtcga atagggcaat caaacacaaa agcaaataat   1740
ttcagatagt gacaggtgct gtgaagagaa cgacttccta acggggtaca gggtgactgc   1800
atagaaggcc ggctgtctta gagaagggga tcagggaagg cctgtcaaag gaggagacat   1860
ttgctttgtg agctgaacca agaggagcag aaagccgtga aatatgggg ctaaagaacc    1920 ttctagccag gaggcctgcg gtacccactc cattggggcc atgatattat tctttcaggc   1980
agggactcag gaaggttaac gttttaaccc tctctaaaat agcatctttc ctcaatgagc   2040
agcttagtct ttggtcgtgg cagagatgac cttgtcttag gagtcatctc cttgtgtgtt   2100
aaaaagttag gaaaggaggg tttctcatat atctataaaa caagtagtta aaaacacaaa   2160
gagctcttcc tttcacaagc agctgaataa gatacatact cccaattaaa tgtcattgcg   2220
ggggttgtta agattaacta aaaccacact tgcacagtat cttaaataag cgatatacag   2280
aatagagaga ttttgttact tgtgtaaagg gagacagcag atgattctgt tttcagctta   2340
```

```
taggctcaaa aggcaaattg tgagatccat cagctgtagt attaaaatct attttgagct    2400
ccgcttagaa aggaaaaaag gtttaagcag ttctttggta tgcttgacta acaaaagcct    2460
ttttttttgg cagccttgat tttcatgtgg atttacatca agcttatttg acaggattct    2520
ttttatttgg actgtagtgt gtatattagt ttctgctaga ctaatatttc taaccactgt    2580
aatctatata ctaataagta tgattgatca gtatataaaa tttgtatgcc atatctggtc    2640
tctgaattag ctgaatgaat tccataaggg actttgagac tgtgtagaca aattttctgc    2700
atcagtttaa tgcagtagag tctaaaatgt ctttaaatga aaattgttgg tctgaagtgt    2760
tggagttgat tatgatacac cccatcacag tggaagcatt gtggagagaa gtcttttcca    2820
ctgaaattga ctgagttgac aacaagaaat acgtattgta acttagttct tagttgaatt    2880
ttatttctta caattttaag ccagagtggg ttgacctgtc acccaagcat ggttaaaatt    2940
gtattcagca tgcaactagc atggagtgtg tcagtcttca attcatttcc ttcattgttc    3000
ttaagttttt ctgccacaat taaaccccac aagttagtca aggtgttgag attttcactg    3060
cttcttaatg gattgccaca ttccctgagg tagtttcttt tggtcttaga gaattgtcag    3120
ggccagcttt tctcacctcc actgtatgga tattttctt ttctaagatc ttgaaatcag    3180
aagcttttct cctaagtgta aaagtagctc tttgtcatac aactgtagcg ttttctgaaa    3240
cagagttcag atgaccttga gtctaaagtg gctaactttc caaggtgtgt atcgctttac    3300 caaaccatt attttttcaag gattcaaaga atgtgtttac aattgataga aaatggaagt    3360
ttaaaaaaat taatactttta tagcatgttg aaatgagggc agccttatac aaagtcatac    3420
tttgagcttg cctagcctat tgtgatcaga gaataatgta attttgctt acaacttggt    3480 aagcaggtca gttattctaa cttattttct gattagaaca aaaagatgta aaaacttgaa    3540
aactattggg aaaagaacaa agagtgaaga ggacttttga gtgctgagga atgtggcagc    3600
ttggaaaaca aacttttag gcagagattc tttgctaggt cagtttgata aagtgagcat    3660
aaccgtattt ttaatcttta atgctaatga atagcataga tgctaataag catctaggtc    3720 tataaaagt cagctttgat agtgtatata gatggcttta acattgtttt tctagcattt    3780 aaacacttttc aaatcatccg gttgcttgat tgggcctagc tgtctaagag gagagaatga    3840
gcccagatga ggaaaagaga ttgattttac tgagctagaa tgagaggaga gagggttgag    3900
tgaatgaaaa gaatagctca tgtgctcccc tccatctgta gtttaagagg ggttgggtcc    3960
ggtgttttgc ttgttttctc gtctgtaaat tctttgattc tctgacacca ctcactatat    4020
ttcattgtga atgatttgat tgtttcagat aaagggggact gcaataatac cttgtgacat    4080
gaaggcaaga tttattcatg ttagaggcag gctttgtaaa atgggccact cttccaattg    4140
acatttgttt ttatagctgt tttcattatg aaatacaatc taatgcctga ctaggttaaa    4200
accatgttgt aacaatagtt cactaaaatt ccttactgat atacagctta tgttgttata    4260
ttccaaaaag atgaatatta aaatttgcca ataatgttta tttaaatact attttcttca    4320
gaggaaaaaa aactattta tgcaaaggag aaagatctat acactatgac tcacttcact    4380
taaaaaaaaa aagactaacg gaaatgacat ggagagactg ggaagttcta gtcatcttga    4440
gtgacccatt agatctaaat gttccttgtttt agccctggtt tgagtgaact aaatttaggt    4500
gtctgatcag tactttggaa atggtgtaaa tgcctttgta attgtctgga ctgatattag    4560
attaactggg agcacaagta gaaatagtga aggaaagaac ttttttgctat tgttatttga    4620 catcactggc atatttatag gaatactttg gtgttttttgg aagtaagtaa accaaccagt    4680
ggttctaaaa agtcagctgg gggataatgg taatgccgct gtttcttagc tgcaagttat    4740
```

```
ctgccgttac ttctcctcca tttttgcattt tatcttgaat agctcctcaa aacctattaa    4800
aatacctggt attgaataat gtaattgaat gtgtactgaa tttcacagtg gaaatgaata    4860
agaaatttcc tgtggaggtt ttttgactta gctactgaaa taacggcctt ttgttgtgtg    4920
attctttccc ttttctcttt gttaaagaaa actgtcttgt gatcttgtag attacagaat    4980
cctttggca atttctgttc ctagcactgc ttttcttttc tttctttctt ttaaatagaa    5040
atggggtttt gctgtgttgc ccaggttggt cttgaactcc tggcttcaag cgatcctccc    5100
accttggcct cctgaagttg ggattgcagg cgtgagcagg tacttttttct gaggcctgcc    5160
tgagcctata tatattttgc acaatttggc attcctccct acagtgttta tgctgatttg    5220
tttctggtaa caactaatac tggcaaatcg gctgggcatg ttactttatg ctgcccatat    5280
tcaggaaaat tggaattcta gctgggtcat tgttcccaga tgatgtagtt tggcaccagc    5340
cattccatgt tcacattttg agtatccagg agggctgggg actttggagt agttggtgat    5400
tccctctgcc acatttcact ggttggtcac tatggcatcc tttccaccac actagtagtc    5460
taggttctca gatgttgctt atgagcctgc aatggtttct agtttcacac tgcagaaatg    5520
agtgaagccg gttacccgtt aatatggtcc catcatcact agagtaattc attgttctaa    5580
aaccagatct gagtctctca ctcctctgca actacttctg attctttcat aacacttgta    5640
aagtccaaac tcctctttag catggcagcc agcttccagt ccttccctcc tatgtggctt    5700
ccattctagc cagacaagaa agggcagcgt tctccaaact catcctcgcc cttcattcct    5760
ctataccatt gctgagcact tgttgagga tgcctctccc gttcaatcta gcttgcatct    5820
tccagctcga atgtgtgctt ccttgcacca gagttttgtt ccgtcacctg tgtgttttca    5880
tacaagctgg cacatatctc ttctaaagcc ctgctgtcat tgtagctgcg tctttacaaa    5940
cattttttt ttaaatttt ataaagtcaa ggtctcacta tattgcccag gctggtctca    6000
aactcctggg ctcaagtgat cctcctgcct tggcctccca gagtgctggg attataggta    6060
tgagacactg tgcccagctg tagctgctac tttatatccc aggtctatct ccaatggagc    6120
ccaagcttcc tgaggccacc tgttgtatct ttctcattca tcttgaagtc ctctgctcct    6180
ggcacagagt aggtacctaa caagagttgg gattgaattg atggtcagta ctttgctagc    6240
ctgatggtat aaagatgtac aaaacatgtt cctggctccc actctagggg ggcaatgatg    6300
gaaacaaata gattagccca cattagtacc aatagtagag gtcactctgg gagaaggccc    6360
ccaccacatt ttgagtcatg gcctaatgag gtaatttagt attgcctgct gcagtggctt    6420
tggaagaaag gctggcattc ttagccagta gaagctgata ccactgattt gtttcacaga    6480
agctttaaat ataacaataa atttgtgctt ggcctacggt gaactttaca ggcaacttgg    6540
aggtaatatg tttgtctctc taagaattgt tgaattcctc ttccctcatc cctcctgact    6600
ggttctcaca agcctagcgg gcctttgcat gtggttggtt cataaaatac ttttgatttt    6660
tgggatataa aatatagttc tccataaaat aacgactgtt accaagtctt tgatttttt    6720
tttcaaacta taaatggtaa tgacattctt tggcctttga tcagaccacc cttaggggca    6780
agagagtagt ttcatgtttt gcttttttcta gtgtcccctg tgtctgggta tagttgcagt    6840
ctcagctgtc atactaacag tgctgagtga gtcccttact ttctttgggt tttggtttct    6900
cccttgtaaa aatgatcctg gactaactga tcattaagtt caggtcaagt aataaaaatc    6960
cttaatgtac tcacaaatac aatttaatgt tcctgaataa tccttgtaaa aactgcagca    7020
gttactcagt tttgtaaggt gtggttgggt actattaggc tcaaaagttt ataggagctt    7080
```

```
tgtgagtata gttaacaact caaaagaatg gggtgttttt tcccgagggg catgaaatgt    7140
ttttgataaa tagagttcat ttgacttggt aatgtggaaa atgagtagcc ctgacacgta    7200
cgctatgctt ttgcagtttt tctctcaagt agcaattggg tggcttttcc tgtaaaagat    7260
agaggaactg attcttgaga atttacgaaa gcttcaaccc taactaggta tgcaaagaat    7320
agttgccctt tatgttgtaa ttttaggaag aaacctacat ctggtctaag tttcatttga    7380
ataatatgat agtttacaca tctgccatat ttgagaagaa agtacctaag tctccagcat    7440
tttagaaata atgctttact ttgtgtagaa atggtcttta gagtttaata gctgctgccc    7500
tctccttttt caaagcagct tgacataatc atgagtatct tgctgacagc ttgtaaattt    7560
tgattgtatg aaaactgaaa ataagaccat ttcacatgga agattccctc ctgccctgaa    7620
acagccaaag aaaactgtag ccatcaaatc tattgatctc tgggcttttgg tacaagtcac    7680
actactacaa ataaaataat accaagtact tataaatgat tttcagtcct tttaaagttt    7740
atttttttaa tatttttttt gagatggggt cttgctgtgt cgtccaggct ggagtgcagt    7800
ggcacaatct tggctcactg caacctccac ctcctgggct caagtgatcc tcccacctca    7860
ggctcccaag tagctgagac tacaggcatg tgccatcacg cccagctaat ttttgtattt    7920
ttttggagta gagatgggat tttgctgtgt tgcccaggct ggtcttgaac tcctgggctt    7980
aagccatctg tctgcctcag gctcccaaag tgttgggatt acaggtgtga gccactgtgc    8040
ccggcccagc ccttttttta agagaaaaac gtatgacatc gttcgattta ctgagtgctt    8100
atggttttac taaggcagta aggttttatg gatacccctat ggtaattaga tagaattagt    8160
gctctgaagt cagctctgta atatggactc agagtaaaca tggcaaaggg acacttaagg    8220
tctgcatttt ctctgggaaa taaacgtatt cttactact ctgaatctag tgctgggaaa    8280
ttctaaatcc ttccttgagga ttaaccactt gaagtaaagt tttgggtccc aagtaggctt    8340
gtgtccctgt ctccttctct ttactttca gatgtttctt cctagagact gaggtatatt    8400
ttacttttac agatgaagaa ggaagcctcg gctgtgtttg tggcttttgt gggtgagcaa    8460
catcacttgc aaagataaga tgagcatagc aaaactaggc tttcaaaata atttttaaaa    8520
atttcttagt gattagaaaa ggaaaactct tcccttgtct ctgttaagaa acgttttcg    8580
actttttttcc tttcttaatg gatcttttat tggcacttct cttccttttg cagaatctta    8640
cttaaaagtc actacgttac attacagcaa acagcttagc taattttat ccagatgggc    8700
cccggttaca ggattgtaca ctattgcgaa tttcttacag gaaagtgaac atcaagtaat    8760
tattccaaat agagttctct taagaacgtg agttacttaa aaatgtctaa ggatgaagtc    8820
acttctgaat ataacttcac tcaagagaac aaataagcaa actgcattta gcataacatg    8880
gtaaattagc tttaactctc cttgatgttt gaacatttgt cgctgttaac tactgtttca    8940
cttttcaaat agtcagggct tagtttgctt ctgtaaggat aaagggaaaa tacgccttca    9000
ctgagtcata atatttttg tggctaactt ttgcacagag aaaagaggcc tctaagaagg    9060
tacccagtga attttttttt cggggcaggg agagaatatg tcattttttg gtttgttgtt    9120
gttgttgtca ttgttttgct ttgttgtttt tactctgaac tgaactgtat cttgacagca    9180
cttttgaatt aagagcatta ctcttattgt tctctactac ctggacgcca cctccctgtt    9240
gccatagtgt taaggatcat gctccgaggt ggggtgaggc agaatggggc caagatcaga    9300
aagttacatt aagctacatc aggtttatac aagcataaaa ccaaatttt ggagcagtcc    9360
ccagaataca acctggttta gccacaccta aaggttgctc ttgaatattc cttgagaatc    9420
cacatcccta gaatgctggg tttcaatggg cccttttatgt acctatcatg gtgtcatttc    9480
```

```
tgagcatttc taaatattcc ttcatgtctt actgacagtt tttcttgaat aaatcttagg    9540
aatattagtg ccattatcag tattttgttt ggtctgttca caccacaaat aactacccag    9600
gtctgctact tgcccctatt tctctacctg ctaatgaaaa tgcttttgaa agtttgagta    9660
acagtattgg agtgtgcaca gtggtattgg taggttctgt actcatcctt aaccacttgt    9720
tttcatcctt tgtgagcttg aagtttctcc aaaaaattta tcacaaaact tatcagacat    9780
agttaataca ctcagagaga gaatcactga aaaagtagat gtagtttaac aaacccagtg    9840
cctttttttt acccatgaat acatatttgt caactaaacc tcattttgca acttgttcca    9900
ctactcgaat ggtaacaaac ttttggtttc ccaatagatt tggaagatgt tgcttttgaa    9960
agtaggaaat agatggcttt agaagatgga agaatatttt gtttgaagtg ggagcgtggt   10020
atgtccttag ctgtctgtga aatgcagctg aagatgggtg tgggccttca tctgcatttc   10080
ccatcttcag tttgaggagg tagttaccct tctaaccact taagaactgc atggtacatg   10140
ctgttttatt tacagggcaa aactgtgctc ccgtagtttc cctggtgctt gccttcacgt   10200
taacacagtg tcatcgtttg gcagtgttta tgtgccaggg tccatgttag aaggaggaaa   10260
ggtatagcga agtaaaggg tgcagttggc ctcccacctt tagttttgta agtgccttta   10320
aagtttgatt tttgtaggtt gatcataagg aagtgataag tatgttaggt tatttgtggt   10380
ttgagctaat tttagtctct ttttacagct gctttgtat cctttgccat taaaacatgc    10440
tttctagaaa gacaactttt gaatgtagga cacagtctat attctatact tggctacatt   10500
tcaaaaaata ttttctcagt actttggaag ttggacagtt ggaagcatag tgacagtatt   10560
taaaaatctt tgattccggc cgggcatggt ggctcacgcc tgtaatccca gcactttggg   10620
aggccgaggt gggtggatca cttgaggtcc ggagttcagg accagcctga ccaacatggt   10680
gaaaccctgt ctctactaaa aatacaaaat tagccgagcg tggtggtaca tgcctgtaat   10740
cccagctact caggaggctg aggcaggaga atcgcttgaa tcgggaggc ggaggttgca    10800 ttgagccgag atcataccat tgcactacag cctgggggac aagagtgaaa ctctgtctca   10860
aaaaaaaaaa aaaaattaag tgatttcttt gctttgtgac acttctactt ttccagcaag   10920
taaattatat tctttcatac aggtatgaaa ttcttgttcc aagctagtgg ttaaaaaggc   10980
acagttgata ttagaggatt tgtaaaagat tatgaccacg cctgcaatgt actgaagcaa   11040
ggctttgctg ggctgtgtat aggaaacctt ccccagcctg tgcccttgct tgatagaaca   11100
ttttgctcct aagggtaggt gcctgtatct gtctccagta ctggttagtt tcacacagaa   11160
cagttgtgtt tcagagcttt agtctcaagc tgccctgctc ccctgaagca gccaccctga   11220
gcatgtgcac tcacaggagg ggacatgtga ggtcatggaa gaagacgact caggaagaag   11280
aagacttggg tttgggttct gactctgcct ttgactgttg tgggattttg aggagttgca   11340
tacaggatct gtaaaatgta gtcattagac tagactagac agccatatag cattacctag   11400
atgtaacttt ctacaaagac atggtcacag gagaagacca gagggtgggg tgatctttct   11460
ggaaaaattg gggcttcatg ccttactcat gctagatatg gtagcattat atggctgtgc   11520
ctgatccccc taatctaaaa gtgggacaga actttaaaat ttcatattaa ctcaaattaa   11580
aacttgaaaa aaacccatta tttccttaaa aataataaaa tgccctgtgg gggcataagt   11640
cacattatat tttaaaattc ctgaatgcca catggatgaa tgtagttcct tttgaaattc   11700
ttcttttgtc taaagaggaa tgttggattt tgtaattgga ctaaaaaatc ttccatttga   11760
gagagaaaca gtctgctgca tgttctaccc ttgttcagga taaaacccac taatagctaa   11820
```

```
catttattga attctgtgtt gtgcctcagg cactgtgcaa agtcctttac atgcaatgct   11880
gtttattata tactgtcaat tggtctataa cagcaggaaa tgtttcagga ggacaatgag   11940
gtcccagacc ctcagtcttc tcctgtgtcc tggattcagc ttcacaatag cactatggca   12000
gtgtggccac tgcttcagct tccacataca tggctgtgaa gagagacagg ggattgtgct   12060
aagcctcccc gatttattag gacataggag gagagagttt gtagtttttg acctttgcct   12120
agttttctaa cctctttcct agatgtcaca aattggccac ccacagtcat attttgcttg   12180
cttcacgcaa tgctttttaa aaagagaag agtttaattt gtgccattgt ttataaatga    12240
atcaggagaa atgacatgca actctggatt ctggcctctc ttgaaaaatc tgaaaatcac   12300
accgtctgag cttacactgg cagtggtctg ctggactgag ggacacaact ccttttggat   12360
gtacatgtgt gcgttgcaga gtttaccaca gtcccacagt gggtcacact gtccttgtcg   12420
gtgtacacta cctagcactt gagtttgcaa cccctacccc aagctgagtt ttctcgtcaa   12480
gcttgatgtt aatgttatgt gatgcttggc cttgtaggta tttggtatat tatcgttaga   12540
taaaattgaa gcaaagggct aaagggttgg tggcctgagg gagtgccctt gacagtaaag   12600
tctaggataa aatcattggc caggtactcc ttcccttccc gcccttcctc tttctctttt   12660
atcctcagcc tccttctgct attttgagga agttagaagc caccaccatt ttttcccacc   12720
tcaggcaact gagtgtggct gtatttctgt cccatgttca gttatttcca ggaactattt   12780
ttgatgacca acttgaagtt acattgggtg ggcctaatgg gggctgataa aagaatgagg   12840
tgaccaaata tgcttgcact gagacggcta cgaagtaagg ttttaatga cttgctttgt    12900 gacttggtca ggagtgatac catttgtcat gtgtccaact tcatgactaa atggttgctc   12960
taccttatcc tcatagctat aataaaataa aataaataca tacattgcag ggaggaatgt   13020
atcttgttaa aggtctctcc ctttagcaa caaaagtaca tattatgttg tagaacatgc    13080
tttttctttg atccttcttg aacacctatt actctataga ggtatgttgt gtatggcaaa   13140
ttagaacaag caatagataa ggatgattct ttaccattat aacccagtca aggtctttgt   13200
cctaagtttt gtacctttct ccagagggaa aggtatttgt atttatttat ttattttga   13260 ggcagagttt tgctcttgtt gcccaggctg gggtgcaatg gcacgatctc agctcactgt   13320
aacatccgcc tcccgagttc aagtgattct cctgcctcag cctcccgagt agctgggatt   13380
acaggtgcct gccacgatgc ccggctaatt ttttttttt ttttttgtatt tttagtagag   13440 atggggtttc atcatgttgg ccaggctggt cttgaactcc tgacctcagg tgatccatcc   13500
acctcggcct cccaaagtgt tgggattaca ggcatcagcc actgcctccg gccaggtatt   13560 tgtatttta gtctctatgc cttaccgtct cagatcagga ggatttggtg atttatcgaa   13620
tgtgggggaa ggggaagaag aggaaacggg aggaatgttc cagattaggg aaatagctag   13680
atggaagatg cagcccctca tcaaggtggg gacacaggaa aaggaacgtg tgcaaagaag   13740
atggtgatct ggttgtgacc atgttgttag aggacgtcca gggaagcatc tggtaggtgg    13800
tggggtgttt aaatatagaa cattcggaga atgctccgaa gcttcagaga acccttccca   13860
aaaggacaaa accagctcag tgttttagca ctccgggatc atatggcatg acagcatggc   13920
tgctttatac ttttttgtgt atgtgaaatt aaaaccaacc actcaggacc aatttctctg   13980 aagcttttg tcaatctttc atttgctttt ctcgtctaga ttgtaagctc cttgcagcca    14040
gtgtctgttg attcagtcat tcaaaaaata atacatgaac agctactagg taccaggctc   14100
tgtgctgggc agttgggata tgtggtgagg aagacaaact tggtccctgc ccttaggaag   14160
ttcagtagtc cagcagacaa agtggctgaa taaagataat ctcagttcac agtgataaga   14220
```

```
gctcttacag gcctaggctc caggtgctgt ggggatgctc aggaaaaggt atctaattgg   14280
gattgggagc aggcaaaaca aataaaggat agtgtataaa ggtaatatct agttgaagtt   14340
ctgaagggca aggaggagtg agcctgtata ttctctgagt ctctccctaa tctgggattg   14400
acttcttgtc cgtctctgtt catattaagt gtcacctagg cttgaaaggg tgagatcata   14460
tttcacttcc ttcctctttg gtcttaacct ttctctgcta cccccctcaca caatgcatat   14520 gcattattct cttattgtat atattttttcc tctcttcctt ttcatgtttc ctctgccatt   14580
acttttaacc tcgactgcca tatggcctct aaacgcttcc agaagggtag cctagtggag   14640
gttattccat catggccttg agctcatgcg accagatagt gaaggcatct gtgtaggtgt   14700
cttctccagg agggtgatat ttgtttcatt gtaaattttg tagccctaga acaccaacaa   14760
cagtgcacag taattagtag gcaggcagta caggattcat tgaagtgaag tgataacttt   14820
tatccaagta tgtatgcaga taatctttga tttgtacaaa aaaaattata ttttaatatg   14880
taaagatttt ttaaaagaat cttcaagttt tagccttccc actaggaata tattgaaaac   14940
atgtgcctag ttcactgact tgcagctgcc actatgagaa taaaggtctc atttagttgt   15000
tgtgaatttt aagggatatt ttcaatgatg ttggctggtt tatcccatta tgtggtcttt   15060
tttttttttt tttttttttt ttgaggtgga gtctcgctct gtcacccagg ctggagtgca   15120
gtggcgcaat ctcgactcac tgcaacctcc gcctcccggg ttcaagcgat tctgctgtct   15180
cagcctccta agtagctggg attacaggcg cctgccacta cgcccagcta ttttttggta   15240
tttttggtag agaagggttt caccatgttg gtcaggctgg tctcgaactc ctgacctcat   15300
gatccactca cttcagcctc ccaaagtgct gggattacag gcgtgagcca ccatgcccag   15360
cctatgtgct cttattagca attctcagta cacagatagc tttgagtgat tctttcaagt   15420
caagtacctt attaaaaaac tcaagtgtac tgataattat cttactttta aatggctaag   15480
tgataagact gaattttttag gtactgtaac acttcagatt acagattctg atatttttat   15540
ggttatttat atttatttat ttttgagatg gagttttgct cttgctgcct aggctggagt   15600
gcaatggcac gatctcggct cactgcaacc tccgcctccc aggttcaagc gattctcctg   15660
cctcagcctc ctgagtagct gggattacag tcacccgcca ctacagccgg ctaatttttg   15720
ttatttttaa tagagacaat gtttcaccat gttggccagg gtggtctcgc acttctgacc   15780
tctggcgatc cgcccgcctc ggcctcccaa agtgctggga ttacaggcgt gagccaccgc   15840
acctggcctg gttacttaaa tttaaataca aaaattatgt tgattaattc tgaatgattt   15900
cctgattgct cccgtttac cattcacaca tttattaaat tcttcgcttg ccatatagaa   15960
gcagtctctc tgccatatat gccatataga taacagaact agctgtctgc aaaccactga   16020
aattgtgaaa acatctcccc tttttcctg tttctaattc tagctatgag gattatatac   16080
agaagtagtc ctggatttga tttttttttt ttttttgatga ttgttttttg atagttgttg   16140
actacaaatc atttaaacgt ctgaaagggg aaaggttttc cttaaaaatg gatgacaaag   16200
gagaataaaa aggtattttg actatttttt tgaatgatga gttttttttt tctctttctt   16260 gttttcttt ggagtcattt atgtgtcact gagtggatac catggaacat gtggcagaag   16320
tagatatatg gggtaaaaga accatagttc ataagctcct tgcacgaatc actgaagtgt   16380
agccgttata tggccactgt cgcaggggga ggcagcagtt ttgaagaagg ggatgagtaa   16440
taatgagtga taaaaaggca tcctggatag aagaccaaac tctgcagaag accccagttt   16500
gattatgctt ttgttttctg atttgcggag gagagtgaaa atgcctgagg ggtgcggggg   16560
```

```
agcacatagg gtgtatgtgt gtgtgtgtgc gcgtgcagat tctctctttc actgtatgta   16620
tttgtatgca tgtatgtatc ttaggactta agctttctag tcaataaatt gccatagtgg   16680
ggaattgctt aattgcttgc cttctgttgt tgtatttaat ttaattttat ttttaatgat   16740
ttttttggtg gggtacaggg tcttaactat gttgtccagg ctggtcttga actcctaaac   16800
tcaagtgatc ctcccgcctc gggctcccaa aatgctggga ttacaggtgt gagccaccat   16860
gcccagctta gttgtatttt aaatgggcct gtttgcagca ttccctactc cccttagttt   16920
acctggctca caacctgtct ttccatatca aggcttctgt caccoctggc ccatgtcagt   16980 gcatttgggc agcccaccca gcatcatcac ctcatgtccc agggaacttc ctgttcctct   17040
cttccagcta tttccttccc tggcagttga gatagtctct acctttgacc tactgttaag   17100
ctcagacctt ctgctctcta gttacagcct ctgtgctgcc agattccctc gctcagttgc   17160
tttctctagt ttgggttttc tccttttattc agatttccag ctgtttctct cctcccccca   17220
ccgcagcctc ctcacttccc tccttatgca tctgagactg tggtcagtca ctttagatgc   17280
tgcctctcca ctgtacttgt gtccatcttc ttacctacca cctctagccc tggagcaggc   17340
tcttcccctg tctttgtctt cctgggccca ggctcctaag cgctgctgga aaaaaaatcc   17400
cccagtattg agcccctaga aatccagtct ttaatcccaa atctgtctcc cccagcatct   17460
ggccatcaga tctaaagctt acctgccatc cttttccacct catttctctc acagggggaaa   17520 aggagccttt gctcctagag tctgcgctcc tgacccccttc ccatctcacc tgttcaaggc   17580
atcttgcaat aaggggttgg tgactctcga ggaatggatc ccaggccctc cctattatca   17640
tcttatgtat gccagttcaa cgttctcagc ttcctccagc cgagacggcc cctccagcca   17700
ctgctttata ctctccttct ctggttgaaa tttttgaagt aaataggtca ctctgcccat   17760
cgttcatctt ccagtcactc tgtgtgttta tcttccaggg aagtgaggct ctatgctacc   17820
aagccactga aataattttt ttttttttcc agactgagtc ttgctctgtc acccaggctg   17880
gagtgcagtg ccgcagtctt ggctcactgc aacctctgcc tcccggcttc aggcgattct   17940
cctgccccag cctcctgagt agctgggatt acaggtgcct gtcatcacgc ctggctaatt   18000
ttttgtattt ttggtagaga tggggcttca ccatgttggc caggcttgtt ggcatgttga   18060
ccatgttggc caggctagcc tcaagtgatc cacccgtcag cctcccaaag tgctgagatt   18120
acaggtgtga gccaccgcac ctggcctgaa ataattcttg acaagatctg cttccttgtt   18180
actaatacag tggatatttt gcatcctaat tttaatgcag ttcagtgtgg tagacctgta   18240
tttgcatatt gaatattccc ttccctgttt taataactct attttttcct tttcttttat   18300
atctcctgct tctctagcta gtcctagacc ttactcatcg gtgtcttctc tgtttgttcc   18360
tcaacttgag gagttcctac agggtttacc caatctgctg ctttcattta gccctttgt    18420 tcttttttgag ccatctcatt cactcaccca ggatgtagca tcggcccttg aattcagtgt   18480
gcacacatac actgtgcact atgggacagc cttcagaggc actttgttcc tgaaattgtg   18540
gtggtctttg cctctcatgg agccttgcat atgctgtttc ctctgcctgg aatatcctac   18600
cttttactta actgattctc gttcttcttt ccagtcacat tttgtacatt tcttctggga   18660
agctttctct gatttcccct ttccacaggt ccaagttaac tgccttgtct aggtcctccc   18720
atggccctct gaaggcctcc tttcatagca ccatgtctga gtatactgta ataacacgca   18780
ttgctctgta atagcctgtt tacttaccta ttgccaagta atctatcaag tcttataaag   18840 ggcgggggctg cttttgttct agtcatttgt atctcttagt acccaatata gtgtttggca   18900
tatagaaaat acccaacaag gccagtcgca gtggctcata cctgtaatcc gagcactttg   18960
```

```
gtaggctgag gtgggcggat cacttgaggt caggagtttg agaccagcct ggccaacatg    19020
gtgaaaccct gtctctacta aaaatacaaa aattagccag gcgtggtggc gggtgcctgt    19080
agtcccagct acttgggagg ctgaggcagg agaatcactt gaactgggga ggtggaggtt    19140
gcagtgagct gagatcactc cactgcactc cagcctgggt gacagagtga gactccatct    19200
taaaaaaaaa aaagactcca tcttaaaaaa aaaaaaaag aaaaagaaa gaaaataccc    19260 aataagtagt tcctgaatga atagatgaga atgctgttta gaaggttcat gaattggaaa    19320
ccgtgattgc tagggaggct ttgagttgat ggtattgtgt tgaaccatgt gttacccagg    19380
atcaatttag attttacact ttgttttctc tgttcctttt tatagtaatt ttctgtatgt    19440
ggtgttttcc ccccatgaga ttgtatacca tttctcagcg agaactgtgt gtaatgcttg    19500
gtggctccct catggtgcct tgcatggaat tggacttcgt ttcagtggat ctgatcccag    19560
ttatgttaat gctcgatgga gctaagtctt atctcgaagc agtccatgtc ttcatcagct    19620
ggccctgcct ccatgccctg cacagaccat gccactctgg agaggtagtt tccctgtggc    19680
ttattagtct tatgttccag tgtgctggcc aagtatgaga gacatcagtg gtatgagaga    19740
gtctctctca ttcaaacttc gtaggttttg tagctgggac tgaccagtgc tgacaggaaa    19800
tagaggcatt tattaaaagc cagagatttt tcaagttgca ggaagcaaag ctcttgttag    19860
ctatgatttt tgtggtgggtt tggtagtcca atataaaagt aaaaactgga tgacaatggg    19920
aggagcatgc ttgggtctcc aaagttagat catttttcct aagtaatttg tctttaaact    19980
tttactggtt tggaatttcc tgagattttg atcttgccag aaagtttata gcaaaagttc    20040
tgagcagatg acacttttgc gtctgaaacc aaatcattgt ttttgttttt aacttttttc    20100
ttaatatatt atccttagtt cagccctgaa gattattctg ttatttgtgg atctcaactt    20160 tcccccccatc tcctggatct ttgtgaaatg aatggtatta attgaataga gaaggaagat    20220
ataaacataa acttagtcaa aaacttgttc ttgactaggc aagttgggct ttatagcttt    20280
gagctgatga catgtctatt cttgtgaaaa agggatttt agtgttggtt tggcttcttg    20340
ttatatttga tttattatta ttatcattat cattattttt gagacagagt cttgctctgt    20400
cgcccaggct ggagtgcagt ggctcaatct cggctcagtg caacctccgc ctcccaggtt    20460
caagcgattc tcgtgcctca gcctctggag tagctgggat tacaggcggg tgccactaca    20520
cctggctaat atttgtattt ttagtagaga caggtttcac catgttggct aggctggtct    20580
tgaactcctg acctcaggtg atccacctgc cttggcctcc caaagtgctg ggattacagg    20640
ccttagccac tgtgcctggc tgattttttt tttttttttt ttttaggtt tgttttaact    20700 ggaactttac gtgaatgtaa ttgaatttag aataaaagca cttaatttca cagtgtgcag    20760
tgaactttct gttacttatt ttaacagtaa acccccttgc agtaaatgac ttggagcaaa    20820
gattgctttt ttaaaaaatg ttttaatttg tttttctttt cttgagatgg agtcttgctc    20880
tgtcaccagg ctggagtatg gtggcgcgat cttggctcac tgcagcctcc ccgcctccta    20940
ggttcaagcg aatctcctgc ctcagcctcc tgagtagctg ggactacagg cacatgccac    21000
catgcccagc taattttgt atttttagta gagacagggt ttcaccatgt tggtcaggat    21060
ggtcttgatc tcttgacccc gtgatccacc ctcctcggcc tcccaaagtg ctgggattac    21120
aactgctggg attacaagtg ctgggattac aagcgtgagc caccacgcct ggccaatttt    21180
tttttttttt ttctttttga cagagtttt cactctgtca cccaggctgg agtgcagtgt    21240
cacagtcaaa actcactggc agccttaacc tcctgggctc gaatgatcct cctgcctcag    21300
```

```
cctcccaagt aactgagact acaggcatgt accactgtgc ccagctaatt gttttttat    21360 tttttatttt ttgtagggac agggtctcgc tattttgccc aggctagtct acaactcttg    21420
ggctcaagca gtcctcctgc cttgacctcc caaaatgttg ggattacagg acaagccac    21480 tgcacctggc caaggattgt tttttaagtg aactgagacc cagccttatt agtggtccca    21540
gagcagacct gggacctgaa gggaaccctt ttcttctggt ccagcgtctt tcctctgatg    21600
ggctactttc ctggagcctt tgattgcctg tcatcagagt aactgagttt gaacagagta    21660
ggtagttcct ctccagacca ccacactcac cagctttcat tctgcttctc tcgtttagac    21720
tgtggttctg aatcctcagt tctatttact gagtgttttt aaacataaaa atgccttta    21780 atgagattga aggccagagg tgggacagtt gaggacaaag tagaaataaa accttcaagg    21840
cgggggtgtt ggtgggagtc ttttttttgtt tgtttgtttt ttgagactga gtctcgctct    21900
gtcacccagg ctggagtgca gtggcacaat ctcagctcac tgcaacctcc gcctcccgag    21960
ttcaagctat tctcctgcct cagcctcctt agtagctggg atttcaggct cccgccacca    22020
tgcccagcta atttttgtat ttttggtaga acgggttt caccatgttg gccaggctgg    22080
tctcaaactc ctgacctcag gtgatctgtc tgcctcagcc tcccaaagtg ctgggattac    22140
aggcgtgagc cactgtgcct ggcagggagt cttatagaag ctgtcgtgga caatgtggga    22200
agtagtgagc ctttgtattc cagtatgctg ggctccactg tgcttgctct ggccccggt    22260 cgctctctgt gtgttattga gtccccatcc acggccatac tcttcgtcct gcttctctcc    22320
ttaccatcct ctccccgcta gtggtaccac ggctaccact agcaattact gacatgtggg    22380
atcttagggc tacttcccta taaggctgca gggcatgtgg tgttggctac gcgcatggta    22440
accatggtag ccctgtggtt ctccacatgt gcgccttgtg acctgggatt ggctgcagac    22500
tagtaataaa ctgcgtcttc tggtatggaa tctgtctgta gttgtacttt ctacctctgt    22560
atttaagggg agatctgtaa cctaccaatg ccagttgaag aggatggatg atagagatgt    22620
taacaaacag ctgaaaaact aactacaatg gcctgcaaaa tagaacagca ggtttttgtg    22680
gcaaaacttt gtgtccatga gtttgttttt taaatatcct catataatct gttttaaatc    22740
gagaggcttt gggtaaaagc catggctagt cttacatgtc atggagtacc tagcttgtga    22800
ggttcacagt ttattattta cagagtgtcc ccttaaatct tctttgggtc ggttcagcga    22860
atgttgctca gatggacttt tttggctgac atagagtcaa aatggtaatc aagcatgaaa    22920
gtacagacag tccttaacgc acaaatgtgt catgcttgaa aagttggaaa gttggttctc    22980
tggagctctg attgtattgt cctgtagaat ccgtgttgtg aatggtggtt aaatcccaaa    23040
tgagtccgta gaacctatat aatctgcaat ataccttgcag tattccaatt aatatgtaat    23100
tcccccatag aactatgtta atgatttgta tgtatggtat ttaatattat acataataat    23160
gattgtatga ataaaaaaca ttctgggctc catgtggatg atggggtgtg tgtgtgtgtc    23220
tgtctatgtg tgggtgggtg tgtgttcata gatcccttt cctgcaatcc tggcactgga    23280
attggtttta tcatttccaa ttaagtttca ttcccatgaa ttttggagta cagactgggt    23340
ccaggtatgc agggcataga ttagagcct gagaaatagg attaggctgg aattgctggg    23400
ttggagatca gtagcttcca ggaacacttt tgggcctgg ctgtcttcat tatcccctt    23460 tgttttctcc tggggtctgc aggtattgcc ctgttttgtt cctctaatat cacttttttt    23520 tttttttctgc ttttgaccag ggttttttgcc tctggtctac aactgaatat cctatcagac    23580
tctcctgatt ttgaaataaa tatatagttt ttttgaggtg ttctagcgaa tttctaaatc    23640
taaatgttgt ggcagagtta ttacatacta attttgctat gagaggttgt agaatcccag    23700
```

```
atgactaatc ttgtaaacca tacacgcatt tccatctaat tctccattgt atatcatgtt   23760
gcagaaaata acagcctcta gagtttacat tgcctccttt gactatattt cttatttaag   23820
attagttttc agataagacc ttttcatggc agtacataac tgtacagagg gcttccaact   23880
tgtcttggga gctctcatct ctgggagaca tcacattacc cactgccccc tgcccccgc    23940 ccccagcctg gatgcactca gcctgtaccc catttctgtc ctcagccaaa cactgctgaa   24000
atgcaagagc tttcaattgc tagccagtga agatgcagac taagggattt ccatgtagaa   24060
gcccgctctt ttcagctggc tcgtcgagag ctggaggccc cttgcttgtt cacatgaggc   24120 ttttttgtccc tgacttggtg gctgctgttt cacttctcag cagaaaggga cacccttgcc   24180 ccccccaga aaggaagatt tgatgtacca cttccgaaag gttcagtcgg gcatcactgt    24240
aaccaagaag ataggtcagg tgaggctgga ggtggaacag ggctgctcgc tagaactcca   24300
gattgttcca caagtgcctt ctggcagaga atgatggaag cttccgtgat ttttttttct    24360
ccttaatagt tatgagcaca gaagaggagc agattgtctg gctatagaag ctgtcttatt   24420
ttttattttt gttttttgaga tggagtcttt ctctcttgcc caggctaaag tgcaatggcg   24480
cgatctcggc tcactgcaac ctccgcctcc cgagttcaag cgattctcct gcctcagcct   24540
cctgagtagc tgggaattac aggcatgcgc caccatgcca gactgatttt tgtattagag   24600
acagggtttc accatgttgg tcagtctggt ttcgaactcc tgacctcaag atctgcccac   24660
ctcagcctcc caaagtgttg ggattacagg tgttagccac tgcacccggc cgaagctgtc   24720
atattaaata gcactttctg cttttagcaa atttaatcca aatgagactt tagattttct    24780
tgctctgact taccagcagt tccttgaaac acatttaatt attttttgcca gaaaatcact   24840 caagcactta cgccattttt ttaccgtgaa aatatgctgc attattttaa aatatattag   24900
aagtcagtaa ccataagatt ttatatgttt tctaatgtat tctgtaagct ttctgctgct   24960
tttgtttgga aggtgtattt tgtaacgtag aggactgctt tatctgcttg taagcttgat   25020 ttttgtttttt actgtaattt tttttctctt tgctgtattg agaaatacat tgagtaatta   25080
taaagtcagt ggcatgttta taagttaata tttgtatcta ttccttagtt actctaactc    25140
aaaacctaaa gtaatcttca actctaattt actctgacat ccagttgact gccaagtcct   25200
ccaacttaat ccttatcctt ttttttttaa agagatgcag tcttgctttg tcacccaggc   25260
tggagtgcag tggtgcaatc atagcttact gtaacctcaa attcctgggc tcaaatgatc    25320
ctcccacgtc agcctctgga gtagctgggg ctacaggctc ttgctaccat gcccagctaa   25380
ctttttattt ttatttttta tagagacaga gtctcactgt tgctcaggct ggccttgaac   25440
tcctgccttc aggcggaact cctgccttca ggcggtcctc ctgcattggc ctcccaaagt   25500
gctgaattca caggcccaat tttattcttg ggatgtatgt ctgaaactct ttccttcact   25560
tccttcccaa gccttagttc aggcccttct catctgtggt cttcaaagtc gccttcagct   25620
ggttcaggtc cttcctttct gctgtatctt tcatgggagg acatgttatg tatcactgtc   25680
ctacttgaaa acttccattc cccattgatg agggtgttac ctccagattc ctaacacagg   25740
tgctgaaggc atgcctggat aaaggcactc ccttgatctc ctggccaggt ccccgtacac   25800
ctgcagcgca tgctccacat tctgtctttta ctgatgctgt gtcttctgcc tgcggagcca   25860
cccaccattc tattcacagc ccctgcctca gcggagcacg tgcctccctc ttcctacact   25920
gagctgtcct ttctattgaa tcccctcttt tttgtagtat gggaaatatt ttattatgaa   25980 tactctttc tctgttgcct ccgtgaccac gttaactttg ccctaattcg ccttaggact    26040
```

```
ccatctgctt agggggaaagt taggatttgg ttacagaaag caagctgcta gaaagaacag   26100
tgtttagctt ctgacaggca aaataggatt ttgcaacatg cttttccttt ttaatgctta   26160
gacattttat atgaattaat atttttattt ggttgcttat acattacttt cttttttagct  26220 agaatgtgaa ccctatagga acatggggat tgccttttcac atctttgtat cctcagtacc  26280
taatgttcag tcaccctgtg gtcttgtgtc gtatatacat ttagccttcc ttaattaaac   26340
catatgtact ggtccccgtc ccccaccccc aaatagagag aaagaaattc cttgaatact   26400
acattgccag tatcaaacca caccttgata tcctctgggg aaagggaggt atcagttgaa   26460
aagagaaaag aggttaaaat ctaggcatta aaatgtgtaa ggcttagatg ctggcaattt   26520
aaggtatgtt ttcctgaggt taattttgat tgtgtgcaaa ttttacctca tatctaactg   26580
taggatttag tcaccacata agatgggata cctccataaa tccttcagaa atgtttgtga   26640
aattaaataa agccttattg aagactcagc tcttgagagt catctaccta cctaacagtt   26700
attcttgaac agaagagtct acttttccc tataaggcag tgtgatagcc atctgtatat    26760
tcatataatt tatgttggcg cttacttcat ttaaaaatgt attccgtgaa tgcagttgcc   26820
aggcggtgtg ctgatcagaa acgtgtacca atggcctctt ttataattat aagaggaaga   26880
ccaacctgaa acagtcacac aaatgattaa ttttaattgt ggaggagtgc tgggaaagaa   26940
aaataaaaga tgcaatgcaa gtgtttacaa aggagctttg agcttgtttg aagtggtcct   27000
tgggcactta agcaaggctt aaagaatgat gtgattagaa gtggcttagc aattctaaag   27060
aacacaggga aggcgtgtgg ccagaacatt ggtccctaga gcacatcgcc tcctgacata   27120
ccatttcctt aagttaatgt tttaccacta tacataggcc ctccccttg tttacccaga    27180 ttttttaat tttaaggatg ttttttaataa cttagaatcc tgtaatttgt tgaacagtcc    27240
tgtattccct ttacttatat tccttgagat tttataaaat attttttaca tgtcccaagt   27300
cttgattata tcttttttacc tcttgttaag aaatacttac ttttctattt ttatgctata   27360
tttcatgttt actgtagaaa acaaaaaaag taaaattttt ctttattcct atcactgcag   27420
cttataagca ctctaaacat tttgatctat attttgccaa tcatatattt tagttaaaat   27480
tgttgttgac ataattgtag attcctgtgc agttgaaaga aataatacag agctgagcgc   27540
ggtggctcac gcctgtaatc ccagcacttt gggaggccga ggcaggcaga tcatgaggtc   27600
aggagtttga gaccgactg gccaacatgg cgaaaccctg tctctactaa aaatacaaaa    27660
attagctggg tgtggtggcg ggcacctgta atcccagcta gttgggaggc tgaggcagga   27720
gaatcgtttg aactccggag gcagaggttg cagtgagccg agatggtacc attccactcc   27780
agcctgggca acaagagcaa gactgcatct caaaaataat aataataata ataaataaac   27840
tttaaaaata aaacagagag atcccatgtg cgctttgcct agttcccca tccactgccc     27900 ataacatttt gcagaactgc agtacagtat cacaaccaca atactgacat tgatacagtc   27960
tgctcatctt attcatattt ccccagtgtt actcgtatcc acgtgtgtat gcattgtgtt   28020
ttcaatactc ttttattata aagctgtttt taatgtgatt caattctagg ttgttttgtt   28080
ctgccctcaa aaagcattcc ctctcctaat catatctccg tcatacccctt gtatgttttc   28140 tttaaacctg ttttaagaaa gcagctacct gtaagagaaa tgagattgaa aacagaattg   28200
ccaatctgct tgtactttat aagcctgttg attgtttaga tacggtttag ccagtttata   28260
gttaccctgg gtgctgaaag gtatgctgga tgatacctaa ccaacagaga accattgaat   28320
gccgttcaaa atggactgaa gcatcagcaa tgtctgaaaa aggcctgaca gtaatgtaca   28380
tgtcaaatgg cccgtaattt aagcagagta gagtaagtag aagaataaac atggggaaag   28440
```

```
ttccagcaac agaggaggct ttgagctttt gctcttcatc ttgagtggat gttgttctca   28500
ggtggtaata ggccatcgag ctttctccac tggctgcctc tctggggaac aaataaccga   28560
aaagatactc agcaccctgg ttggtacata ggtggtcagt tgatttatac ttcctggttt   28620
tcagtgttgc ttgaattttc taaatggaaa cacagtacct ttataatcag aaacaatcc    28680 cgagttttga tttgagggtg ttgtaaaaag ttaaaaaaaa aaaacagaa atgtgaaaag    28740 gaagttgtgt tagagtattt ggagttgaga aagcatgaaa aggacagaag agaagctggt   28800
tgtcaggttg catggggtag ctacaagcac actgaccaga aagtcagctg gaaaaaaaat   28860
gtagaaacag gagataaaac ggccaagggg ctatacaagc aaacagcaag gacctgagaa   28920
gaaaaactag ttaggtgtga ctgtcagagt gatgtgtaca gtgtgatcct ttctgtgtaa   28980
aaacaagcag taagaattcg ctgtttacgt ttgcgtgtgt ttggagaaga gtggggaaga   29040
gtaggcactg ccagactgtg aacactggtt aggttattgt tatatctttg tattatatac   29100
actggacatg ttatttgtat aatatgagaa gaaattttat aaatcattaa atctttttggc  29160 atttaggaac atttgtgttt tctaatagtt gcttctatac tattatcttt attatatgcc   29220
cttcatcttc tcagtgtttg gctgttgttg tgattccctt ttgtgagcag tgttgaagtt   29280
agctaatatt catttcttct cccttctttc accctcctcc agagtctgat ttgaagtatt   29340
cctagctgct acctataaaa gcaataagca agattgtttt acttttcaca aactcgtcct   29400
gttctgtgcc tctgcctcgg acatagctgt agtatagagt gttgtctccc ttacatcctt   29460
ctatcttaga cctactagta aatattaatg ctcactctaa gttcttctca attctttttt   29520
tttttttttt tttttttttt gagaaagagt ttcgctcttg ttgcccaggc tggagtgcaa   29580
cggcacgatt tcggctcacc gcaacctcca ccttctgggt taagcgact ctcctgcctc    29640 agcctcctga gtagctggga ttacagtcac gtgccaccac ccctggcaaa ttttgtattt   29700
ttagtagaga caaggtttct tccatgttgg ccaggctggt ctcaaactcc cgacctcagg   29760
tgatccacct gcctcagcct tccaaagtgc tgggattcca ggcgtgagcc accgcgccca   29820
gcctcttctc tcaattcttc ctgaagctct ttctgcacta gattcctcag gaagggcttg   29880
tgggaacaat cttctgtgaa tcaacagtac atattcataa tagtttgtca gcagcctatt   29940
attttaaggc catttggtct gtatataaaa atgtttggat cacattttct ttctttaagg   30000
taaatatgtt attctgttgt cttctggtat aaagcattgc tgtaaatgtt tgacagtcta   30060
attatctttt gcttataagt gacttagggt ttttgtcta tgtgcccaaa ggattttttc     30120
cctctttctc tctttttttt tttttttttt tttttttaaa cagacaggat ctcaccctgt   30180
tgcccaggct ttagtgcagt gaggcagtca gagcttactg aagtttgaa ctcctgggct    30240 tgaggaacaa aggattttt taaccttta attcaaagtc tcatcattta tgcaaccatg     30300
tcttggtgtt ggctgttttg ggttgttctc cctcaaaaat ccatgtgctc tttcaatatg   30360
tagttttaaa tctttttttt ttaatttcag gaaaatcttg aattagagtt ttccgttttt   30420
cgtctggtac attgcttggg tttccttctt caggaactca gcctgttatg tgtatgtttg   30480
atcttctttg cctgtcgtct gtttctttca cttcctctca cttttttaaa cttcattta    30540 taaaaaaaaa ttttttttc gagacagagt ttcgctcttg ttgcccaggc tggagtgcaa    30600
tggcgtgatc tcggctcact gcaacctccg cctcccaggt tcaagtgatt ctcctgcctc   30660
agtctcccaa gtagctggga ttacaggcat gcgccaccac gcccagctaa ttttttgtat   30720
ttttagtaga gacagggttt ctccatgttg gtcaggctgg tcttgaactc ctgacctcgt   30780
```

```
gatctgcccg cctcagcctc ccaaagtgct gggattacag gcgtgagcca ctgtgcccag    30840
ccttattaaa aattttaaaa acatacattt aaacttaaca gaaaaattat gagagagaag    30900
ggggtggtgc caggcttttt taaacaacca gctcttacat gaactcatag agtgataact    30960
cattaccatg aggacggcat caagccgttc atgaaggatc tggccccgtg acccagacac    31020
ctcctactag gtccattttt aacattgggg atcacatttc aacgtgagat tggaggggg     31080 caaaactaca aaccatgtca ctcagggatt ggaggagcaa gtaccaccta tactttggac    31140
tcaggtagaa aggcaaaata tccaggaaat aagctgctac cgtccagggt tcagcagagg    31200
tgcccatcag cctgccaagt actcaagagt ccagcctcta gggagctaat catcatggtg    31260
agctcttcga ggcacaggga gctgggaaga cagtgcttgc cacccctgcc tgaatagtgt    31320
ttgcacagag agttctgttg tgtcttgatt gggtcctcct gccactggga atgctgtgga    31380
ttatactagg tctctatctg gcttgtttca gggctccatg tgaaaacctt cttgatatcc    31440
tagccatcca cctgctcagt ccctagtttg caaggaggct gtgggagcc tagattctgt     31500 gtcagataga atgtactaca ttccgtctca ggaatgtacc acatcagaaa acagtgcgac    31560
ctgcaggaga agtagaggtg aagaggcaca ttcttccgag aaatgtttct ctcaacaccc    31620
agcattccct ggatatcagc aggaaattac tcactgctag aaaatgcccc atgagccttc    31680
tgttaaggag gtcaagggag agaacagaga aagttctcaa agttgacttg gtcactggta    31740 cttttcttatg cggttcttat tttgtttgcc atcgtcatca tcatgctatg tctattttct    31800
caatccaaat ccactgcttt caccttggtt ctttctgacc ggtttggcac actcattcag    31860
taaatcctta tggagagccc aatgtctgca taattgtgct gtgctgatga ccaagctaga    31920
cctacgagtg tcggctcctt tgagatgtac gggacagctc ttctgtcatc tcttctggga    31980
agcctctcca ggcttggtga acagtggcaa gatgtttaac agttgtacat gtgtcccatg    32040
ttccttccta agagcctggg caaaccagac ccggtcgcag gtcatcgtag tatggcgtga    32100
gcttcctctc tccttttctga ccttttgtgt gatggcaaga acctgcagag tgacacaagc    32160
agcaggcttc tgaggttgct ctagcctcag aatggccgtc ccttctccac cctggccctc    32220
attgctgagg tttcctttga agcaacagtg ccggaacaga ctaggggaag cagcttggac    32280
atagctgtat gatttattac cacccattga ggccaaccaa agtcggcaag gagaggtagc    32340
aggtcagtgg tgcctggaag cttcctcttt cctttgcacc agatgtgact gctctgcaat    32400
tactcctaaa tttgctactc tcgttttac tagccaacct tgatgttttt cccttcttcc     32460
tgtagaatag acttcccctc tgatcagtac tttctactca acactatttg tggccacagt    32520
gggaactcat tgaggacagg gaccatgaca ttactacctg acccatcaac acttggcata    32580
acttgaaatg caaggacaaa aattggctgc aagtacaatg tggtcttcac tctgaaggtg    32640
atccttaaaa cttggctttg gcatcatatt gccttaatat acctagggga ttgggtaaaa    32700
ccagttactt taaagagtt ttacaattct ggccttctag ctatcttgtc ttcttaaaca     32760
agagcacaag atgaatgtat cttagtgaaa ttttatatgg tttgctttga gtaatcttgc    32820
gaagattgat ttttagcaca gtaggaaaga cacattctaa tagtgatttt tttccccgag    32880
tttatgtact gctgttgcat gaaaatctga ctagatttaa tgttcctaaa gttctttgtt    32940
catcctgatt tttgcaggtc ctagggaaag ctttgttttc ctcttaacct aacttagatg    33000
ttgtcatttc atgagctttg gaggaagagt gtatagccaa ttgtgtaatg tcttttaaagg   33060 atattatctc tgcaatagtt gtttataagg cctaagttat tcatgtaata atagtggccc    33120
cggatctgtt tctagcaata ggtatatgga ttttggttcc tatatagttg tagttgtggc    33180
```

```
tttgagatat tgagcaagcc cttttaagaa aggatttggc atccctcagc cttcaaaagc   33240
ttctcaaaat tgatcatatg ttattagcaa aggtttactg cctgcttcca ttgtatagac   33300
aatttatttt ttatgtattc cgttctaaga aggcagatga ccaaaagatc ttgcatctgt   33360
tgcccaaggc ttgtgactag agaggaaaga gataagaata cttttttaaa atcccatttt   33420
actaaatatg ttgaggaagt ggtaagatat attaatttgt tgagattttt ctgttatgcc   33480
tattatatga aataggtact ctgaacatgg cttcttaatt aaatatattt gataaaatac   33540
aacttgcttc ccctggagtt tagaagtcag ataactgcca tggagagcta tgctttcttt   33600
gttttaaaga tctgcttatg aacatgataa acaggaacaa tttaatgttt tcaatatttt   33660
cttgtatttt actgcaagtt tatacacaac ataaatatgg gggaaggggg aaatgtttat   33720
accagagcca tcctgcccat tctttcctta cagaaggaca aaggagcagt atttatttta   33780
actacaaaaa tactattgta ggttttaaaa attccgtata ttttgatatc ttgtgttcct   33840
cttgaccttt aatttgctaa atagttgcaa agaatgaagg taacctgcat catcttctta   33900
aaaaccaact ctatctaatt ataatagttt gtctatctct gaaaaatagt gatgtgttca   33960
ttctgaaatc agaactaccg gatgcagctg cattttgtta ctatttgaat ttcgggagag   34020
ggaggaggat gcagcctttc gagctgctga aatacacaaa cacaaagaag acaccaagca   34080
tagtagaact gtgttaagct gaccaagcca gaagaagcac ctattctcag catagtatga   34140
gacgtaaagg caatataatg ggcatagttg aagatggtag aaggaaaata gactctgatg   34200
gtttaatgtt aaatgctttt tttaaaaaag tggtattcca atatcgaaga agaagacttt   34260
ctacttttag aagcaataaa ggaaattgca gaggaaaggg tcataggtt ggaatacata   34320 aaaattaaaa acttttaaac tttttttttt tgagacagag tctcactctg tcacccaggc   34380
tggagtgcaa tggtgcaatc tcggctcgct acaacctccg cttcctgagt tcaagcaatt   34440
ctcctgcctc agcctcccga gtagctggga ttacaggcat gggccaccac tcctggctaa   34500
tatttgtatt tttagtagag acagggtttc accatgttgt ccaggctgat ctcaaactcc   34560
tgacctcgtg atccgcctgc ctcggcctcc caaagtgctg ggattacagg catgagccac   34620
cgcgcctgga ctaaattgtt tcagtattaa tttttttaa aacaagatct tactgttgcc   34680
caggctgaag tacagtggcc caatcatggc taactgcagc cttgacttct gggcctcaag   34740
ggatcctccc acctcagcgt cccgagtagc tgggaccaca gacatgtacc accacaccca   34800
gctacttgtt ttatttttat ttttgtagag atgaggtttc accatgttgc ccaggctggt   34860
ctcgaactcc tgggcccaag caatcctcct cccttggcct cccaaagtgc tggtattaca   34920
ggtgtaagcc attgcgccct gcctgatttt ttaaatgtgc aaacagataa gttggaaaag   34980
tgatttccaa taaagataaa gagttgatgg ttttaaaata cgtaaagagc ttatatgaat   35040
gagaaaaaca ctaacattcc aaaagattag aaggcaaagg acagaaagaa acaaatcact   35100
atgtctggga agggacatga aggagcaggt tcccactggg ccagcgggc tcaaacccac   35160 tggggacgtc cgagagactg caagggccat gccttcacat tgccgtacct gagaagcaag   35220
gagctggggt atttatctct ttcacacttt gggaggctga ggtgggcgga tcacctgagg   35280
tcaggagttc gagactagcc tggccaacac agtgaaaccc cgtctctact aaaactagaa   35340
ataattagct gggtgtggtg gcacacacct gtaatcccag ctacttggaa ggctgaggca   35400
tgagaattgc ttgagcccag gaggtagagg ctgcagtgag cataaattgc accactgcac   35460
tccagcctgg gtgaaactct gtctcaaaaa gtaataataa tcatgataaa taaaataaca   35520
```

```
ttagattgtt agcagaagta gccacaggtt tctcccacct ctctgcaagt tgctgagtgt   35580
gattcccatc aagaggtaca atgtcttttt attttt attt tatttatttt atttatattg   35640
cctatgttgt ctaggctggt tccaaactcc tgagctcaag tgatccttct acgtcagccc   35700
cccaaagtgt tgggattaca ggcatcagcc actgcacctg gcccagatac tttttcttga   35760
gtaggaattt cgagtcaccc tgaacattgc atgccttcgt agtggggaag acaataggaa   35820
accacaggct gtaggctaaa atgggttgtg tttcttgtaa cgtcatgaca aggcataacc   35880
catcttggca tagtaaatag taagcactca ctgaactgat gattttaaat ctttgctgtt   35940
tattcagcaa tatcctaaat tagcgctatg ttagtggagt tgcatctccc tcatggatta   36000
gtctgaaaaa gatgagaaat ctgtatgtag accaagttat ccttaaactg ctcataatgt   36060
atgatgcacg tggttttacg tgtacagcct ggtaccattg ttcttaggca catttcagtg   36120
ccagaactct taatacccag gaagaagcaa aaagaaagat ggaggtgcag ctagaggttg   36180
tggcctttga acgattcatt ctgccttaat aagagtggtc tggctgagct cggtggctca   36240
cacctgtaat cccagcactt tgggaggcca aggcaggcag atcgcttgag cccaggagtt   36300
caagaccagc ccaggcagca tagcgagacc cccctcccc ccgtctctac aaaaaaatag   36360
aaacaatgag ccaggcatgg tggaacgtag tgcgtggtgc ctgtagtctc agctacccag   36420
ttggctgagg tgggaggatc acctgagccc tagaagtcga ggcttcagtg agcccttatt   36480
gtgccactgc actccactct aggtgacaga gcgagacagg tcctgtctcg aaaagaaaga   36540
agaagaatta aaaaaagtga ttagatccct tgtgtttggg acacttgttg gcagcaggga   36600
tggtagcgtt tatgagggtt gcatgtaaca tcgcctagct cagacatctg tttgactgtc   36660
ttcccccctg aagcgcaggc tctgtgaggg caggtctttt gtctttcttg ttaatcttca   36720
tatgcttagt gcttgccaca tagttgatgc tcagtcgata tttggatgaa ttgaagggat   36780
taatgcattg aatctgaacc ttgctttctt aatgcatatg gggagttctt tggaaagcca   36840
cacagaggag cttggttgcc tgcttcctct cttccccaga ttgtcttttt attgttgtgg   36900
cttcactgaa gcactctcac ttcaaataat tttgggcatt ggtcgtattt tattctttgt   36960
tccttcttca tccttacccc tcagatggta tgtagaaaag tacactacat ctagaaagta   37020
ctttataaac tcatttggtt gataataata catatgcctt ttccttggtc ctggtagcag   37080
aatcttgtgc cactcttgga atacaaacga aattcttaac caaagccagt tcatttga   37140 tgttctattt tcctcccatt cacactccaa attgtgcacc aaagtatcat cctagttttg   37200
tgaggatggt tctccatact tcagggtagg agtatcatgt ggattcctat gatacctttc   37260
tccctgggac catggagggc agcagctggt gattgatagt ctgattcccg gtgaggaaag   37320
ctgtgagcct tccacttgca gatgtctgcc aactacatgt gtccttagtc aactgtacca   37380
ctgtcctccg gcaaacagca gaagcccagg gcctgaagtt cttaagctgt cattatggaa   37440
agcagaaggt aaacaaaaca gaagtgaaag tagatttaat ttttagact gttctcttac   37500 aggaatggtt ttgtggttct cagcatttta aaaaaatag tggttccaat atgtttatt   37560 gacatcaatt actgtaagtc tgattcattt tctgcctatt gatttctacc caaggtgaaa   37620
ttcatgacat ttaacagaaa gcataagtga ttttttaaaa gcagacacta ttagggacgg   37680
taaaaataag atttaaagtc gggacacttg aaaaagcaat ttttataccct ttggtaacga   37740 ttctattctg attctttgta taaataatat aaacaaaggc tctagaagct tactataatg   37800
aagttggtgt gctgtttcta aattctggtt taaggcccaa attcatttta tctgcattaa   37860
cttttttttt tttgagagtc tcgctctgtc acccaggcta gagtgcaatg gtatgatctc   37920
```

```
ggctcactgc aacctctgcc tcccgggttc aagcgattct cctgcctcag cctcccgagt   37980
agctgggatt ataggtgtgc gccaccacgc ccggctaatt tttgtatttt tagtagagac   38040 ggggttttcac tatgctggtc aggctggtct caaactcctg accttgtgat ccgcctgcct  38100
cggcctccca aagtgctggg attacaggcg tgagccactg cacccggccg tgttaaaatt   38160
tttcagtggt agaccactat gtcaatatgt tgctttcact gacaacagta ttttcttaaa   38220
gataggatac cccatttcta gatgaatctc attctagctg gaaaataatt tttcagttct   38280
gaaactacat caggcctcag ggaatcaaaa ctagctatta gccacacaca tataaagtgg   38340
ctttgcttta taaacgattt agggtcacca tcaatgacaa tggtcccttt ttattgtatt   38400
tttaagagtt tcttatctta aatggctgca taactgtaga gttttaaaaa aattaagtaa   38460
atgaccatgt taatgctcta ttaagcttcc aaacaatatt gtaatttact ttgaagattt   38520
ttttttattc tcaacatcct gcagcttgac cgtttgcctc cgtgtctcag tgctgcttat   38580
tttgaggtgt ggactggagt ccatctgtcc cccttgcctc tgaactgctc cgttttgtgt   38640
ttcgtaattc ttcatgctgc atcctgggcg catttctctg tagtagcttt caatttgctc   38700
atgctttgac tgggcttagt ctagcgttta tcctatctct taaggttttt taaaaaattt   38760
tcatgattat tcatttattt ccaggatttc tcatttcttc agtcacatct ccttgttctg   38820
gttttacttc ttcctgtttt tattcataac atctttttta tacacgattc cttcatgtat   38880
ttctaatctt aagtatattt aattgcttat ttgattcttt ttttttttta ttgagacagg   38940
gtcttactct gccaccaggc cggagtgcag tgacatagtc atagctcact gcagcctcaa   39000
ctacttggac tcaagcgacc ttcccacctc agcctcccag gtagctagga atacaggtgt   39060
gagagccgcc acacccagct gatttgtctt actatgttgc ccaggctggt cttgaattcc   39120
tgggctcatg tgatctgccc ttcttggcct cctgaagtgc tgagattata ggtgtgaacc   39180
actgcacctg gccaagtatg tttatttatt tattctaatt tgagagggag tctcgctctg   39240
tcgtgcccag gctgtagtgc agtggcacaa tcccagctca ctgcaacctc tgcctcctgg   39300
gttcatgcga ttctcttgcc tcagcctcct gagtacctgg ggttacagtt gcgtgccacc   39360
acacctagct aattttttgtg ttttttagtac aggcggggtt ttaccctgtt ggccaggctg  39420
gtcttgaact tgtgacctga agtgatccgc ccgccttggc ctcccaaagt gctgggatta   39480
caggcatgag ccaccacgct tggcccaagt atgtttattt ttaaagtccc caacaagcta   39540
tacaataaat tgcatatgga atggattttt gttctagttg atttgttggt tatcatttgt   39600
agaactaact agttgtcttc tgtgtttgat accttgcttc taggtcattt tgagttggga   39660 gcctttttgtt ttgtttttat tctcatgctg tttttgagcc tagctgtgcc tttatggttt   39720
tctctaaatt taattgacca ttgtttata tttggagcag tgggtgtaca tcagagtgtg   39780
aaagcagccc caccctctcc accagaaggt ctccatgcca gtttcacgaa gcatttttca   39840
tgccctcatt cctgccctta tcccttgatt tgtggggagt ttgtaaagca gttgattgtt   39900
ttttttccac gtagttttcc aagtgcacat aattgttctg ttagtgactt gtagctccat   39960
tatctattaa ccttgcccca gaccactgta caagcggacc caacgcttcc tccagctgtg   40020
gcagggacag ttacttggta tcctgctgcc ttttcaatgc tgaccagttt tgccccttcc   40080
tcccctcaac ccctgtcttt cattcaacta tcaccaaacc aaaagattct ggtttgcttt   40140
ttagtatgtg ttcttattca gtacatagtc atttaaaaat ttaaaccaaa acagacttgg   40200
tactgattag cttaatttta agcttttttct ttattattaa acagtgtagt ttatcttagc   40260
```

```
atttcatatt aagtatatga tttatttcat attgcttata tgaatgtaca cataaatata    40320
ataaaaatat ttcctaagg tttttgtagt aaattatatc gtttcattaa cttcatata    40380 tagcattgct tttgacctgg aagacattga acctctgatg atttgtatat tcctcggagt    40440
atactttgtt acatagaaat tttctcattt ataatgagat ttgtgattaa caaaatttgt    40500
tcaacatgca ttactttgaa gatctggttt ctaaatttt atgctagtta ccccaccccc    40560
ccttctatat atatctccct attcagcgac tactgcaaga gttccaggaa atgtacactg    40620
tgtgttcact tactgcattt taaatcattg cctttactat atttctgcat ttcccttcaa    40680
tctagctctg tctgtacatt tctgaaagcc agtagcttcc ctgaagaacc aggtaacaac    40740
ccgaacaatc aaattagata accatttgta gaatggaggt tccgggagat cttagaagat    40800
gtgatgggtg ctaagggact ttgtagttcc ctgaagttcc agtgagtaaa aggtacccttt   40860 ggaattttt attccttcag acttttaaaa cagagatcac tttcaaaaat tactctttct    40920
gctttgaatc catgttttag taactatttt gacactgttt ggtcagaagg ctgtgtgggt    40980
caactgcaaa taaataaaat aaatgtgatt tcagtaattt ccatttgta acaagtaatt    41040 gagaaaatag gattggatca gatatttgct tatacacatt cccttcagg agcacttctg    41100 ttctataaag aatgttggta tattgttaag gacacttcaa gctttgggaa cctttgaagt    41160
atccattgat tcagttaaca aaattatgtt gagtgcctac cctgggcctg ggcctgtgtt    41220
aggaggggac actaagatga gagtccaaag cacttcttct cagactcctg gctgctaatg    41280
ggttgctgcc tctacttctt cacttagcag atagctttaa aatgagtaat gcattttacc    41340
atggagcccg taagagacat tcacccagtt gtggaccgag gagaagggtg ttaaacccag    41400
attgtgatgt ttcacttgat gaagtgctta atataaacat ggaaatattt ccgcaaggat    41460
aaactggctt ttatgcctgt gtgttttcag gagaaataga aatctctaat caaatattgc    41520
cagcttttca cccaagtttg acttttgcc taattgagtt tgggaggtgt ctgaataatg    41580
gataatgagc tttcctgaat aaatataaaa attaattaac tccaggctct aattcattct    41640
gttaccagag ttttgtaagc atgttacccc tttgtgttca ttgggagatc atctgttacc    41700
ttcttaaatg agtggggaag gatgggaaat gaggaagagc tataaaaact attcaggtga    41760
agaaggtttc tgcccctcct tgccccttt aaaatctcca gctcagcaga tgctttgttt    41820
aaacttgatc aagtgcttgt gaatcttcct agcctagcta aatcataact ttggaaggac    41880
ttgctttttt ctctcatgac aatggtttac cacagaaatg attcagatca ctttgtgtgc    41940
ctgatgccta tgtaaaatga tacagtgaaa tggaaaccat ttacctgtaa gctttgggca    42000
cacccaagcc tgcttcagga gcacatgatc aggcgtgcac tctgggagag ccgtacacat    42060
ttgacatcta tgatgtgtgg cgttttattc tatcacattt ctgaaatcta cactaagaga    42120
aaggaggctc ttaaaaaacc actgaggtgt ggactggggg aaggagagat ccgtaaagaa    42180
cctgtttgtt acctgttgat actatttccc attggtaaaa tttctaattt agtgtgatcc    42240
agccctgaaa tgctgaggca cacactgaat gactcctgac atctttagtg ttttgttca    42300 ggggactctt ctgggaatct gtttcatggc aagtttatta ttccctttg gtttggctca    42360 tcagtttacc cagcagtcat cttaatcggt tttaaaggct tttatttat ttgtttct    42420 ctgtggaaat tttacacatt cagtagatta gaagtagtta tttaatcttt ggttagcata    42480 ataaagatc ttctagggac atttttgct tgcagtggaa ggctagttaa atgtgttcat    42540
tagtcatgaa tctgctttt ctatagctgt tggaaacgta gctcccctgt gatacagttg    42600
tagaatacag aaatctcgtt ttgctgttac ggtacggtag tctacttact ttcttccaaa    42660
```

```
ccattaatgt tatagttacc tttaattgcg taggtcctat cacccctcaa ttttaagact   42720
ctaagcctgg cattttatct tacaaaatga aatataaaga cttgtactca gagtatgtgt   42780
gtgttttcca tataccattc taaagtagag aaagatgagg gattcgccag aaactgattt   42840
ctaataaatt atccagaaac tgaccccttc tcacctcttc tgttactgtc actgtggttt   42900
cagccacagc atcctttgct gcattgttac cttagtttcc tgactgtatc cttccttaca   42960
ccattgatcc ctgcaatccc atctgcgcgt agcagccaga agggatccac ttactgctgt   43020
gatcagaaat cctcagccag gtgcagtggc tcatgcctgt aatctcagca ctatgggagg   43080
ctgagactgg agaattattt gagcccagga gtttgagacc agcctcaaac tgggtaatat   43140
aatgagacct catctctaca aacaggaaaa aaaaaatttt ttttttttt ttaactagcc    43200
aggtatagtg ctaatatacc tgttctggga tccagcatgc tctccctgac ctgcagcttc   43260
atctccacca ctttgcccct cactcccacc acaatggctt tcttctcttc ctcagacatg   43320
ccgtgcgtcc tcctacctgg aatattcccc tccaaacatt cccatggctc actccctcac   43380
cttcatcaga tctctgttcc agtgtcactt ttactggaag gtcttttgtg accatcctac   43440
ttattataaa aaaataatct gcccaacctt ctccttttat ttcctctact tgattttca    43500
atttagtact tatcagctga catatatttt gtctctctgt ctctctctgt ctctcataga   43560
aggtaaattc tataaaggaa ggaattttta tgtttggttc tttgctgtag ctccaatatt   43620
caaaacagtg cctgacacac agtaggccct ttatatttgt tgaataaatg ttgacactct   43680
gatatctaat ttttgtctgg tgactaatac gaaaactata gagtgataat aaaagcatta   43740
ccttagtaga ctggaaaggg atgagcgcta ggatgaactt tctgcctggc gatcttgctg   43800
aatttaggag gcagattggg gttcaaagga ggctgaaatg gctaggattt gcagagcagg   43860
gtactaagga tgagcaggct atgacagaaa gaactccaga aatctgcaaa gggatcacct   43920
tgagtctggc tggatacagt gtacactttg tagggtgtct cttcatgagc ttggataaag   43980
aacaactgtt ggggagtgga taattcccag cactcattca agcttgcatc ggccagaacg   44040
gagagagaca gacctctgta atacgtagga tatttggtag aaacattcaa ccgaaaacca   44100
tcagatatgc aaaaagtaat aataataagt aaacaatgtg atgcatagct agaagaaaaa   44160
tcagacatta gaagcaagcc cagaaatgac agatgataaa ttagcagata aggacattaa   44220
aacagctatt ataaataact tagcagattt aaagaaaaac aacataatga ggataatgga   44280
agaaaaacaa ccgaatacca tttctaaaga agaaaaatac aatatctgaa atgagaattt   44340
agctggatag gattaatagt ttaggcactg cagaagaaaa aaacagcatc tatatgagaa   44400
tatacccaag ggaagtacag agaggaaaaa aatgtggatt gggggggtgcc tcagtgacat   44460
atggaacaat attaaacaag tctgccccca aaatacttga aggaataagg ttcaagtttt   44520
ttccaggttt aatgaaaact ataagcctac agattcaagc atttcaacaa accttcagca   44580
aaataaacaa aaccacagta ggcctggcac actgtctcat gcctgcaatc ccagcacttt   44640
gggagcctga gtcaggagga ttgcttgaga tctgcttggg caacatagcc agaccctgtc   44700
tctacaaaaa ataaaatgaa ataaattagc tggatgtgga ggtccacacc tgtaactcta   44760
gctagcctgg aggctaagaa gggaggattg cctgagccca gtagttcaag ctggagtga    44820
gctaggactg catcactgca ctccagccta ggcaacagca agaccacatc tctctctctc   44880
tctctctctc tctctcaaaa ggcagtgaaa taacgactta tttggggaaa aaataaaggc   44940
agagaatttg ttgccagcag actagcataa aaaaaaggaa gtccttgaaa cagaagagaa   45000
```

```
atgataaaag atggaaattt ggatatatac taaagaatga ggattgctaa aagtgacata    45060
catagataaa tatgaaatat attttttattt taaaatttat ttaaagcaaa aataaaaata    45120
catcatattt ataacataga aataaaaaat gtatgataat agcataaagg ataagtggac    45180
aaatgctgtt gtcgtatttt tggtaaaatg cactattatt tgaaagtaga ccatcgtgaa    45240
ttcgatgcat attgtaaacc aaatagaaca ctaaaaaatg aaaataaaga gatatggcta    45300
atgtgccaat ggtggagata agatagatgc aaaaaaagaa aaacattcaa agaaggcag    45360 agacagagga aaaaggacc aaagatcaaa tgagtcaaat agaaagcagc taaactagca    45420
atatggcaga tttaaatcta gccatgtcaa tagttatatt aaatgtaaat gttctaaata    45480
cctgaattaa aggatgaaga ttgtcagatt agattgaaaa agcatgaccc aactacatgc    45540
tgtctgtaag aaattagaaa aagaacaaat taaatccaaa gtaagaagaa aggaaataga    45600
gtagaagtta gtgaagtata aaacaaagag caaagaaaat caattaaatg aaaagctggt    45660
tctttgtaaa gatcagtaaa attgataaat ttctagctaa actggccaag aaaaaagaaa    45720
agacatacaa attaacagta tcaggaagaa aaacagagaa ttcaaaggag tgtaatgcaa    45780
actttatgct agtaaatgca ataagttaga tggtatggaa aaaaatgtga acaatacaaa    45840
gcagactgtg gttgcctttg gtggcagtag cggggtggga gtggaaggtt gaattgactg    45900
gaaccagaag cacaagtgaa cttttttgggg tgatggaaat gttttgtatc ttggttgcat    45960
tgatagttaa atggttgtag acattgctta aaactcactg aacacttaag tgggtatgtt    46020
ttattatttg taaatatac ctcaaaagca gttttaaaaa tgtattcaag tacatactta    46080
agatctttgc attttactct gagtatacct taattttaaa atctgttttt taaaaagtat    46140
tatgtagata ccttttattt tcccaatgtc tttattaaat gacatctcca cgttttgctt    46200
cttacctcta ttttttttt tttatttctc tgtctctcag gcatgcacac acacacacca    46260 aaaaagtac atatgcataa tccttttggc tgaataaaat cagttgcaac tgttatttcg    46320
gcccttattt gctccgggta aatattcgtt agctgagtgg tttatctgta tcagatattt    46380
cttacatctt catccagtca caccagctgg actgaccaga ttgttttttca cttcaagggc    46440 agaaatttgta ctcactgctg aatgcttcca aatgatacgt agaataacaa atttaagact    46500 tagatttta ctttttcagg tctttttttt tttttctgtg ctgtatagca tttccctgaa    46560
agcttaatct catctgtaag tgatgcagtg gatgtgttac tattggatta atttatttac    46620
tcttaggtag gttttgtaatc tgtcatcatg ctgttgtttt tttgtgtggg tttgtttttg    46680 gtttgagac agggtctcac tctgctgccc aggctggaga ggctagagtg cagtgatgtg    46740
tttatgggtc actgcagatt caatctcctg ggctcaagtg atcttcctgc ctcaacccct    46800
tgtgtagatg gaagcacagg tgcacgccac cacacccggc tatttttta aatgtattgt    46860 agagacgagg catcatttt ttgcccaagg ctgatcttga actcctgggc tcaaacaatc    46920
ctcccacctc ggctcccaaa gtgctgggat tacagatgtg aaccaccact cgagctccat    46980
cattctgtta ttagttgttc tctagtatga gtcaaaaact cttacctgcc cttttacagt    47040
tttataaata agtaagcaga atagcagaat gtggacattt tttaaatcca aattgaatat    47100
gcacatgact caaggagtca aatagtaccg taatcggttt atgataaaat ccagtggttt    47160
ggctgggtgt cgtggctcac acttgtaatc ccagcacctt gggaggctga ggcaggtgga    47220
tcacctgaag tcaggagttt gagaccagtc tgacctacat ggtgaaacta ctaaaataca    47280
aaattagctg gcatggtgg tgcatgcctg taatcccagc tacttgggag gctgaggcag    47340
gagaattgct tcaacccggg aggcagaggt tgtggtgagc cgatatcgca ttatttcaga    47400
```

```
acaattttcc acaagatcag tgagtgctgt ccaatagaca tataatacaa cccacataca    47460
tgactttaca ttttcttgta gccatagtag aaaaggtcaa aagaagcaga tgaaattaat    47520
agcctgggca acaagagcaa aaccccatct tttaaaaaat aaaataaaat atggtggttt    47580
gctgtcccca cctcagacca tttctctggt cttttctcatt gaccaccact cccaatcttt   47640
gttctgctga ttgattacag cttgtatata tctccatatt tctaagcaaa atgtttatct    47700
tttttaaatt tataaattct ttttattatt tttcagagac agggtcttaa ctctgtcgcc    47760
caggctggag tacagtggca ccatcgtagc tcactgtagc ctcgaactcc tgggctcaag    47820
cagtcttcct gcctccgcct ctcaggtagc tgagactacg ctacaggcac ataccaccat    47880
gcccagctca aaatgtttat cttttgatac attattcgag accattatta aggtggatga    47940
tttagttttc ttaaacagcc atcccctttc ttttcctccc ctctgcttca ccgccccat     48000 tttcccaatg ttttaccttt tggttaaatc agtactcatt gtttacatta tttgcctctg    48060
cacatagtca cagatagtat tgtactgtac tgtactgtgt ttcttttta aacattattt     48120 ctgttgttaa taattgactt tttaattttt ttcctatttt gttttttaaa gagatggggt    48180
cttactatat tgcccaggct agagttcagt ggctcttcgc gggcatgatc ccactgctga    48240
tcagtacagg aatttccacc tgctccattt ccaacctgga ccagttcacc ccttcttagg    48300
caacctggtg gtcccccatt cccgggaggt cagcatattg atgccaaact tagtgcggac    48360
acccgatcgg cataacgcat gcagcccagg actcctgggc tcaagcagtc ctcccgggct    48420
caagcagtcc tcccacctaa gcctcccgcg tagctgagac tacagacact tgccaccaca    48480
ccaggttaat ttttgtgttt tttgtagagg tggggttttg ccatgttgtc cagactcatc    48540
tcaaacttct cagctcaagt gagcctcctg cctcagcttc ccaagtagct gggattatag    48600
acgcatgcca ccacacccca tgataattgc ctttttttt aatttgcata attttctttg     48660
tagcttttgc taatgttccc atatcttctt atagccttac agaatgattt tccacaagat    48720
cagtgagtgc tgtccagtag acatataata caacccacat acatgatttt acctttttt    48780 gtagccatag taaaaaaggt caaaagaagc agatgaaatt aatagtatct tttacttaac    48840
ccagttcatt caaaatgtta tttcaataaa tggtcaatat ttaaaatact tgagatattt    48900
tgcttttatt tatttctttt gttactaagt cttcaaaatc caatgtgtat tttacactta    48960
cagaacatct cttttagac tggccacatg tagctcaggg ttactgtatt ggacagagtg    49020
gtttcagttt caagttttc cttggagaca tcctacttga aatttccatt ctccatgtat     49080
ctgggtggtt ggtctataga cttgccactc acagctgtca tcttgagact ttcttgtcct   49140
ttcttctcta ttggatattc agtttcctgg atttcaggtc ttctcatttt cctctagtag    49200
ttttgttagg tcatggttgg tatggcatgg ttgggatagc gtgttcacac agctatctcg    49260
tgagtcatac tcctccaatc cagcctgctc gcttcccgtg tctgtcatgt agttgtcacc    49320
ctgctatctc tccctccagt ttttgcagaa atttcctttg tcttcactct tggtcttcct    49380
ctcccatccc ccatgtatcc tatatctttc tctttcttgg tttatttcat cactcaggtg    49440
gaaaagatgc tccagtggat tactgggaaa aggggggagca tggatgataa aggtattgag    49500
accttacacg tcagggaatt ttttttttt ttttttttg agacggagtt ttgctcttgt      49560
ccaggttgga gtgcagtggc gccaactcgg ctcactgcaa cctccacctc ctgggttcaa    49620
gtgattctcc tgcctcagcc tcctgagtag ctgggattac aggtgcccgc caccacgccc    49680
agctaatttt ttgtattttt aatagagacg aggtttcact gtgttggcca ggctggtctt    49740
```

```
gaactcctac ttcaggcaat ccacccacct cggaatgttt ttattgtccc ttctcatttc   49800
atgactgctg ggctaggtat agaattccag aatcattgtt cttagaatct cgaaggcatt   49860
gcttcattgc tggccagctt tcagtgttct tgcaaagtct gaagctgtgc taatcacctc   49920
atcctttgaa agtgaactgt tttttcttcc cagaaactta cagaacattc tctttgtccg   49980
cagaattctg ggattgcaat tactgtgcct tagaatgggt ctgttttat cattatgaag    50040 agtactggat gggtcgggag gttttcttga attacttctt gatgttttct ttccttgtat   50100
ttttttgttt gctaatttc tatttttttt tcttggttta ctttcttggg caggggatt     50160 tcttctactt atatttgatt cttcagttga gcttgtcatt tttgctatct tgttttaag    50220 tttcgagaga catctttgtt ttatataaca ttctgttctt aatacataga tgcaagatct   50280 tttcttctg agtatattaa tatgtatttg aaatctttct attctctgca gtttgtttcc    50340
cccaagggtt tttttttttt tctggttttt gtttttttgtt tttatgttag agactttcct  50400
gttatatctg gtcatcagtg gtacctgcat gtggtggaga gtagggcctt attggagtat   50460
gagaaccttg agcaggtgta aggagcctgt caacactgcg ctggcctcag ggcctctagg   50520
gaggctgcca gttgtgcatt ctgaggatac cttttggttg tgccttttgt ctggtcagat   50580
tatctagaga tgctctgcct cctacctgga ggagaagggt ctagctgcca gcggtgtgag   50640
tgtctcttgg ggaaaaggac tcgagttcct ggtgtttggc ttgtgtatgg ccgcttaccc   50700
catttttggt ggagcgctca catcttccac tgtgccaaca gtcttgctgc agttcataga   50760
ccttctggtt tacattttc cagaaagtat gtctttagat ttctgcagaa gtctgaggag    50820 catgaagga gcttggggaa tgagatggca atccaggtct tcccagatgg ctctacccttt   50880 atccctgca gggaatccca ctcctccttc ctgactggga gcacagccag agccttggga   50940
ggaatctgga gtggaaatct cgggcggtct ggctttctta ctgttcactt gtaattttgc   51000
tttctcacaa ctgccaacca ctaatcagcc tgatttccag cttccagaat tctattgctg   51060
ttgtctgctc tcctattccc accgtagggg atggggctgt cttttttttt tttttaatt    51120 ttggtaaaac atacaaaaca taaagtgttc cattttagcc attttaggt acacagttca    51180 gtggcagtaa gtacattcac gttgtgtgta tttgttttt tagtaataaa caatataaaa    51240 tttttaagt aataaaacac aaataaaaga ttgtttaatg tgattatcgt ggaattttag    51300
gtgtgatcag gagccatggt gtagtcttct gttgaaacag ggtgatagga tttgtttacc   51360
acctcctagg aaagcagttg gatagtttgt tggcataaaa gtacatttta tctattttta   51420
ataatcgtag ctttatagaa attgcagttg gaactcccag gcctggcatt caaggctctc   51480
tgagatctgg gctacccacc catgtcctcc agccgtctgt cgcacctcct actgcccact   51540
cactgttcct ggcatgagat gtgatctcca gcccccatgc ctttgctgtg cagggtgttc   51600
cagagtgaat tgtccctcct gtctgtctct ctgccctctt cctcgtcttt ccatcttcct   51660
gccccacatc actgcctcct acccaaggcc tgtgctcatt cctcctcggt ttccccccat   51720
ggcctggtac atacctctga attatcacct tgcatttccc atattgcccg gctctctttg   51780
atgtctgttt ctttgctggg tcttcctcag tgtctgacgg tcagttaaat gtctttattc   51840 tttttgtag gatatccgac atgaagccag tgacttccca tgtagagtgg ccaagcttcc   51900
taagaacaaa aaccgaaata ggtacagaga cgtcagtccc tgtaagtatc cacgtggccg   51960
gtaccagtct tgctcttcct ttgctgcagg ccttttttagt caagactcct ttcgcctcag   52020
ggtttagtat aataataaat caatgtagca gaggtttatg acgcgattgt ttcctatagt   52080
aaaggcatta gagacttata gtaatagctc attttttccac cattatagaa gggctcaggt   52140
```

```
ttcagtttct ggaaaattca gtgaagttca aagcactttt cttaagcttt gactgttttt   52200
gtgatgaatc attttcctac cagctgaagc agagtatagc aggcataata aaaccttttc   52260
tggatgactc agcagcagcg tcattagggc atgagcactg tgttccgctg taatgaagcc   52320
ccgcacaggc attcggggtg ggcactgtcg tccctgcgc  tgaatatgca aggcagctct   52380
gtctggagtc cccaccgcct caccccgc   caacctcatc attttctcc  ctctttcctg   52440 ctgttagttc ttcctaggat tgtcagtgtg cctgctggcc tgtggcagcc ctgtccgcct   52500
tctgagtgat tggctgtcag tctgccggta gctgaaaagt aaataactta acatgttaga   52560
atttgcataa agtaaggaaa actggagctg agtacaggac ttgaactgcg ccatctcctc   52620
taggccacag aggcctttt  gacccccttc caggtcttta gacattgtca ggcagtgagg   52680
ggtcgtagct gccagtgtct ccatggtagc gtgctctgcc agggatgcag aagattctcc   52740
agtcattcct ccagtgggca cttcctgcag gtcctgtgcc catggctggg agtggtggct   52800
gtcattgttc tctgccagaa gggttagcag tgcatcctga cctgacttat gtggcgccca   52860
gattcctgga agggtctaa  aaatggacct agacttggtg tagaacgtgt gcctcttggc   52920
ctgccaccat ggttccctgc ctggttttgt gtgtcagctc tgccgcttaa gaactgagtg   52980
gcttcgggca agttgttctc tctcatagga gtgtgtgaag atgaagcaac ataagctgct   53040
tagcccagcg cccagtacct cacgcagaca taagtgctca gtaaatgttg tctgtggtgg   53100
ggatggttgt caccaacatc tgaagtgcac ttctaggtca tcaggtgaca tgattggcgc   53160
caacacatgg tactcttgat ttagcacatc tcagctgagg cacctcattg atatttgttt   53220
aaaaacaaaa acaaaaaacc ttggtgattc tgctgtgaag tcctggccag aaacctccag   53280
accgctgatc aacacgcaac agaaccatca ccgttcacct ctttgacatg gtgccaggat   53340
accctggatc tctagctttt gctatagttg ctctaattag gaataatct  tgtctttaat   53400 attcctttgc tacatttttt aacatttctt atctaaatgg ttttatgaat cagttttaca   53460
gagaaaaaaa accagtattt aaaatattct tccaggggct ggtccaagta cagtagtgtt   53520
tacaactatg tgatcacaac cagttacaga tttctttgtt ccttctccat ccccactgct   53580
ttacttgact agccaaaaaa aaaaaaaaaa aagttattc  cagggaaaca attctccaac   53640
tttttcactc ccaatctcac tcctcttatc ttcctcccgt actcctatcc tcctcccgta   53700
ctcctatcct cctcccctac tcctatcctc cagtagaaac agtcatttgc tgtgaaggtt   53760
atgggggaga atgagtcaag gtagaaggtc acctgctgcc cagctcacag tgctgctggt   53820
gatgacagca gtccacagtt acaggcactt gctgaacgag gggctctgta tacacctcag   53880
ctcattgact cttcccacaa ccctcttgtc acctaccatt tagcaaatga aaaaccaag    53940 gctctgaggt gagttgtttg cccagagtca cccagtgctg tttgaaccca ctcacataac   54000
caaccaatac cattatgtaa ttttgaggt  cttttatctc tgtgatccac ttaaaaatta   54060
tccaagtatc tttatttgta ctaagcctcc ataatgagaa acagtgttcc agatggtggc   54120
tagttttcaa agacatctct ctttggaatt cttctttaga acaaaaagcc ccagaccact   54180
tatccccatt catatcccct ttggacctag ggagaaggta ctatttatag gtgatcacct   54240
gagtttattg tcccttgtgc tgtgccagaa ataaaggtcc ccacctgctc ttattagctc   54300
tactaacagg ataaggaaag tggccctcag agagctactg cttttgtgac aaacaaatga   54360
tacaagaaaa aaaagtggc  ttttaatt   tagtgacctg gggcaggact tccaaatgaa   54420
agtttatttc taaaaactaa aaggtaaatt taatatactt tcagtgtttg ggcttaaatt   54480
```

-continued

```
ctctttcaag tgtctttgtg atatgctctg aattttaaaa atttagaatc attgaagttc    54540
attatacttg aactttaaaa aaaaaaaaca aaaacctcgt ataaaggtca aggtatgact    54600
tcatgctgct gtgtacttag gtcatttaat cttcaaacca ctggatagag gttaggttga    54660
agttcgatct taaatcctac ctactgtagc tcattgtacc agcaacagct gtagggacta    54720
ggtggaattc atggtgggtt ttgttccctt ttaaagattg aagccaccat attttctgcc    54780
ctctaaaagt ttatgtcagc caggcatggg tggctcacac ttgtaatccc agcactttgg    54840
ggaggctgag gtgggtggat cacttgaggc caggagttcg agaccagcct ggccaacatg    54900
gtgaaacccc atctctacta aaaatagaaa aattaggtga gcatggtggc ctgcgcctgt    54960
aatcccagct actcgggagg ctgaggcagg agaaacattt gaatccggga gatggaggct    55020
gcagtgagct gagaacatgc cactgcactc cagcctgggt gacagagtga gactcttgac    55080
tcaaaaaaaa aagttatgca tcagagaaca gatcctttga tgccctcctc tgccctgaaa    55140
ggttttgggg ggagagtaat aagtatcaca acaagatatg acctgagaac agatttccca    55200
gataggacat gatccatgtt ttaatatggc ttactgctgt tgcttcatag tgtgaagctt    55260
cagacacttc tgaaaaccct ttcagaaaat cccagtcgcc ccatactgat gactaatctc    55320
aactaaaaca gggcttcagc cagtgtgaat gccactaatg ccaccaactc accttttgctt    55380
ttctgtaggg tgtgcacctg tatgtacaca ttcagctttt ccgggattaa cctctgagtt    55440
ctggtttgtc tttcagttga ccatagtcgg attaaactac atcaagaaga taatgactat    55500
atcaacgcta gtttgataaa aatggaagaa gcccaaagga gttacattct tacccaggta    55560
agcagattgt ctgaattttc tatttaatgt caatttaaga gtttgagagt gctgttatcc    55620
acacctcaaa taaaatctgc cacatccttt agaaggtcag gatttcagca taccaaaaag    55680
cagcaaggaa gggggaaaaa tcatccttca aaggttcagt ttggttataa ggaacgctaa    55740
tcttttctgg gaagcataag atgacattgc tggaaatgag agcttataga aaacaacatt    55800
aaaatgccag agttgcctgt gtggtctgtt ggcagagaca gcagagccat ggctggagga    55860
gggtctgtac ctgtgttgct tccagaagta tttgtcgtag agcacttgtg atggcaaatc    55920
taagaacgtt agcagtagac caggaatctc tgtccagagc cattcagagt agctcagcat    55980
ggttctcatt cttttggccag aagaaaggca tcattggatc atgtgaacaa gcatgaaaaa    56040
tgacttaaaa tttctgttgg cttttggcat ctttatggaa acaaaatcct gaaagtggtt    56100
taataattga gcctcttgta aaacactcag tggcatgtga ccaaagggt atctgggaaa    56160
gaggataaaa agagtttctt tttaattaat cttctcaagt cttaacttgt tacctgtaag    56220
ttggtctaaa aagactgggt ttcttatttt gttttttcatc ataattttttg tttctcattc    56280
catgtcagct ttcagtctta tatggcttta ggccacaggg cgattttgaa catttgtaat    56340
tttgcttaat aattaggaaa ttaaaattct ggggaagaca gaatgctcta tgaagaaagg    56400
ctgctttgag caaggagcta ggtcagggcg cgttcaactg aggccttttct tcactgcctt    56460
tttgtcttgt cccagttcct ccccatttat gactaaaatc agcccagatg cttctcgtca    56520
tctgggatgc agagcatcag cccagctgtg ttcagtccta tggggccatt gagtaagttc    56580
ttggtgcatg gatacagggc aggccttac caggccctga gccccctggtc ctcccagcac    56640
ctctggggta tttaggggag gctgatgggg gaggggttg ataaggcggg agatgtctgg    56700
ggatgaggtt gaggcaaaag tgacttcttg aggactttgc tttttggaga agtcaaattt    56760
cctacttctt gatttcagcc cttcaactct ggtatggagt caggaagccc tttaaatacc    56820
tgttgtcggg tgtatcatgt caagtgttgc attagcaaat gaccatgtat ccttgtgcta    56880
```

```
ctgtcctgcc tacccccgcat cctagcgctt ccttgggaca tgagaagctc tgtctggttt    56940
gtgaggtggc actgggatg ttgagaaact gtttacacag tttcccttg ccctggggat     57000 ttactaaagg agtcgaggca gcctgacccc aaagcatcac ccctggacac tatgaccgaa    57060
acatttcccc agtgcccaaa ccaagaacac ccttcccatt ttttttcag tggtgttcat    57120 tatgtaataa tacaagtctc tcttctcatt ttttaaaagt cagaagtaca gaagagcaga    57180
gaataatgtc caaggggccc tccttcacct ccccgtgca gtgtcagcta agtgtggtgc    57240
gtgtccttgc agatcttagg ggattgtgat ccttcagacc attctaaact ggggtggtgc    57300
tgggagttag ggaaggcatg aagggagtag tggagagctg cagtgactgg ggtcttcatg    57360
ccagggtgga gaatgcaagg cccaggtggc cagccatgtg ccacgggatt tctggctgcc    57420
aagagctgtt tatctgttca ctggggaggg aagagttaaa tgtggtctgc ttttctccga    57480
gtcccttcag cacagggagt gctgacttgt cttgttcagg tagtaagttc aagatgagct    57540
caggaaagaa agtgagagga cactgagggc tagtggttga gccaagtgtg atgggactta    57600
aagggagaag atttaaagaa taaggagctt atgggccggg gacggtggct tacgcctgta    57660
atcccagcac tttgggaggc tgaagcaggt ggatcacttg ggtcaggagt tcgaggccag    57720
cctggccaac atggtgaaac cccgtctcta ctaaaaatac agaaattagc tgggtgtggt    57780
agtgtgcacc tgtaatccca gctacttggg aggctgagac aggagaatcg cttgagccca    57840
ggaggcagag gttgcagtga gccaggattg cgcccctgta ctccagcctg ggtgatggag    57900
cgagactctg cctcaaaaaa aattaaaaaa aaataaagag gttaggtgaa aatagatgag    57960
aatggaaacc atgagaagaa gtgatgctgg ccaaggacat gacaggttct gatgtggagg    58020
tgataggcaa tgtctcttcc agccactgct aataattgag acaaactcaa ggcattcata    58080
ccctgtgtcc agtaaacatc tgtgcccatt gccaggtgag ctggattgaa atgggccagc    58140
tgctcagcag acaccctcat gccccagtga ctctgttccc cttgggccac ctcattgacc    58200
atttatgttt ctacatctcc taagtttgtt gggccaagga tggaggctgt ctgccgtcag    58260
ggtcctcatt gctgatggta ggaatagttg ctgatgtttc attggatgtt gctgtattct    58320
agggactgtg ctaagtactt tatagaaatg aacatacttc attttcacag ttttatgaat    58380
agggactatt attagtcaag taagcgatgg ggaaactggg gcaggagcg atgaagtgac    58440 ttgcgcaagg tcaaagatg atgtgattgg aaccaagaga agtgttgtgg ttggccacgc    58500
ccccacactg cctctcatct gcaccaagga gttttgtccc atagcccaag ggccttgggg    58560
acgaatctca gtggaggccc ttagcgggcc tgcctgagcc agaaagcaga atcggcattt    58620
ttctgtcctt ggttggccca gccctgaact gagatgcgga aatcgccttt cgctgcctgg    58680
tagaaaatgg agctgcagtt actgaccacc aggcagagag aggtgggtcc ctgtcccagc    58740
ctcagccacc actctgccta agctgtgggg actgagggcg ctgtcgttag ctgactgcag    58800
aaggtgagca cacgctgtag catgttatgt ttcagatgtc acatgttgtg ttattgtgtc    58860
tttgcagggc cctttgccta acacatgcgg tcactttgg gagatggtgt gggagcagaa    58920
aagcaggggt gtcgtcatgc tcaacagagt gatggagaaa ggttcggtaa gtctcggctt    58980
catttgctgt gtatgtgatc atgcatacca ctccatatag ttaccatttt cgtccagatt    59040
tttaaattat ttttcttgcc tttgtatttc ctttacgtag tatttttatt taaaaaaatt    59100
aaaacagcag catataaatg catgttggtt gtcaaccagt taatgaagtg aataaaaggg    59160
aggaggcgga agaactgcac ggacctcttc gccccgcct tctcctgtgt ggtgcgtgtg    59220
```

```
gcgctccgcc cacctgtgct gcctgtgcgg ctctcatcac agtgtggagt tgtgtgtgga   59280
gttatggaga cctgctttta tcttgaaaag caagttctta gtgcatcttc atggtgtctg   59340
attttttggc tggtgagagt gtggctacct ctgcggagct gtgggagcgg ctgactagat   59400
gagatttgcc tccattcagt acctagactc ttgccctgcc acacctcttc ggagtgagca   59460
ttgacttcag gatgtgtgtc attctaagtt cctgcaactt ttcaaacacc cctcgggcta   59520
gcgtgtggct gcacggtgtc catttgtgca ggccaccact cctcttgcat ctgggtctag   59580
ccacctctcc ttcttgactt accatagttc attttgtacc atgctttcag aatgagcttt   59640
ctcaaatcca gtctcacca cggttcttcc cagctgaaaa cccttgtgcg gttcccttg    59700
cctcacagga taatacatgg tgtggcttac ggaaccctgc aggtctggcc ctaggcccct   59760
ggacacagac ctctcaccac tcttggaact ttagccagga caaagttttc tgtttttagt   59820
ttcttaccat gttctctggg ccgaggagtc ccagtgccca cgttcatccc acttgcaggc   59880
accctggac ggctgccccc agctcccaa ctgcctgcat tctcccctgc cctcctcact    59940
ctgttggaat agctgagaat agccgatttc tgggcagccg gcctcctgtg tagactgtcc   60000
tgtgtagact gtcctgtgta gattgtctgt gtagactgtc ctgtgtagat tgtctgtgta   60060
gactgtcctg tgtagactgt ccatgtaaac tgtcctgtgt agattgtctg tgtagactgt   60120
cctgtgtaga ctgtcctgtg tagattgtct gtgtagactg tctctgtaga ccgtcgtgta   60180
tagactgtcc tgtgtagact gtctctgtag accgtcgtgt atagactgtc ctgtgtagac   60240
tgtctctgta gaccgtcctg tgtagattgt ctgtgtagac catcctgtgt agaccatccc   60300
atttagacca tctgcctgtg caggcgcagg ccagtgttca gcagggccac aggctcctcg   60360
gcctccctgc cctcgctgct ccccaacact gccaaccctg ctgcggggtc caggaggaga   60420
tgggctgagg atcgtggaga ccagcaggag cgtgtggccc aggagcaggg aactgggtgt   60480
ccttgggcct tgccaggtcc aggctcagct aggacacggc tctcacagct gtcctggttg   60540
cctccggcca cagaagaagg tgagggctcc agagaggcca cctttccaaa aaagcacag    60600
tcatggccct agaatgtaaa aaatccaagt gttaagaagg aacacatcaa aggaaacttc   60660
agcagtgaaa acttgaagca ttaaccacga agcctctgcc tccaccacac acaaagaaac   60720
ggctttagtt actcgcagaa agtcttcctc ttaggacagc gcgtgtttaa aatcataggg   60780
gtttggtttg ttttgttttg gggttgggt ttttggggg tttttttaccc ttgcctactt    60840
tttaaaaaat gaaagtgttt atttgcccaa caataacaga cagggagctt gcctaagtgt   60900
tctgttgatg atataatgta tcttgtctta gaaaaaaact ttttcagtga aggtggttt    60960
ttaaattttt tcttccctcc ttagtagctt gattagtaaa atgtgaagtt acaaatgtga   61020
agcaaacccc caccctttcac cactagtcag caattttgag taaagaaaca aagcatcagg   61080
tgctcacagc acacactgtc ttagagggaa ggggaagcct ggtggcctgt ggaagccttc   61140
agcatagctc catctgcagg cttctgaccc tcagcactac tgacacttgg gctggatcat   61200
tgtctgctag ggatccgggc agggagtggc tgtgctgggc gctgtaggaa gtttagcagc   61260
atctctggcc tctatccacc agatgccagt agcaccccct cccagatgt ggcagtcaga    61320
tgtgtttctg tctagactcc agactttgtc caacgtcccc tggtaggcca aattgccccc   61380
ggttgagaac caccgctcta gatggtattg agggtttggga attttaaatc aagacattta   61440
ttcagaaatt accagatata gtagcatttg cttcttattt atttctttgt tgctaagtgt   61500
ttggcaaaac ctctttgctg tgagcacaag gtttgcttta gcaattgttg tcacattaca   61560
gcaaggagtg gtgtccagcg ctgtagttat gtatttgagc agtgtccagt gctgtagtta   61620
```

```
tgtgttccag cctcaccagg ccctgtgctt cattgtctcc cactcaagac tgaccacaaa   61680
tggcccacag atccactgtg acaacctttc cctttgggtt actgtggtgg catcgagaac   61740
atggctggtt ggctttgctg tagtttactg tgataactgt gccagcagtc cctgctttcc   61800
tttgttaagt atcccattcc actggaggat tacttgggcg tgcagattgg catgaaaagc   61860
aatgtatggt ttgagattgt taaagtttct ttgggatcaa cattttcaat tctgtatcag   61920
cattatccct cccagagggc tggctgggag aaatcatgag aagttacagt atcttatttg   61980
ctcagctaat ctaattataa atgatccaca cagcttgtgg taaaaccagc ttttggggag   62040
ttttcattta atgcatactt gtcttctgat ttccttcctt caccaaatag tgtaggatgc   62100
tccctcttat ttttggcaaa catgcctgtt atcttttggg accctgggct tcctggaaac   62160
cagttatgca gaagatgatt gtgtgtgtta gactggggtc atccagatgg ctagagttct   62220
cactggttct gtttaaggat tgactttaga cacctcagtg taggctgcac catggcgtaa   62280
gggttgggat tgttgtttag aagggggaag taagcaaggt gagtttaatt ggccattgca   62340
gaatctcacc cgtatctccc tcctgaaatc ctcactaaag ctgccgtttg ctttcaggtg   62400
ctttcatgca caagacactg cattttgtat cacagggtcc atataattca tttttctctc   62460
gtacttagtt ctctgtgtta agaattactt acttagttct ctgtgttaat aattttttggc  62520
gaaaccaaat tacccgtcac agggttactg tagatgtctt tcataggttt tccaaacacc   62580
acttgcccac ttgtttggga aggccccaag gactgtttaa catctgcctt catggtggaa   62640
acagcaacta tgagagatgc tagcatgttg gcactgccat gttcctctgg taccagccca   62700
agataggact caatttgagg cctggtgaag tactgtgttc taataaaaat ccatctactt   62760
ttcatggccg tatatatcaa tgtaataggg taactgaaaa tgtgatcttg tgcctttttaa  62820
aaattttgtg tgtttaaaac aaaaatttct attggaaatg acagagcata gcttgttgct   62880
gtagacacct gagagtcctt aaaaataaat attgggttat tgacacttag ttgcatgaca   62940
gaattcctca cttgtacagt tccaaagtct tagtctttac ccagattaca gagggttatt   63000
aagcattagg tttggttttg aaagtgagtg cttgctgtct ggaggtgagc tttaagactc   63060
gtctgccctg cttatgagat gaggaagggt ggcctcttcc tcctgcattt ctgttcttcg   63120
cttccttctc tgtctgctca ctctgtggaa tgcccacccc agcacgggtg gggtggaacc   63180
tgtcagatca gtctcttgtt tctggggtct tgaggcatta taagatctag ttgttagaag   63240
tgtgggatta attcatcttt tcacattctt ctaagttcct gcttttagct gccacaccca   63300
cttttggctaa gtgggggtct tgccatgtaa ttagcgcctc catgccaagt ggcagaattg   63360
cttcaatggt gacagattgt ccccattcaa gagttcactt ttggcaactc atcattgatc   63420
caggaaggtg acatggatga aactggctaa gacttcagac aggcttgtgt ccagactctt   63480
gagaaagctc tgttggcttc tggtctggca ctgtgaagtt tgctgtgatg ctggcaccac   63540
aacctggtgt ttcctaattt gtttctccca catttttgctt tggttttgtc ttttgggcag   63600
cttccagctc cagtagagca ggaccaatag gcatttgtgg ttctatattc accctcctca   63660
cgtgcttcct ggctcctcat tgcccccaga tgatgccaca ggtccctggg cctgctgcca   63720
gtcgtctgtg atctgggcct ctgctggccc cttctccagc tgctcttttc agcctcttat   63780
ttgcagtcac tgcctaggaa atcctagtca tccttcaaaa cctgcctctt gcacagagct   63840
ttctctgatc tctcttttct gtaacttggg ctgacctgaa acatttccct cttctgaatt   63900
cctgctgcat gtccgtagca tttccccctc agccctcccc catagtccac cttgtcactg   63960
```

```
ctgggcacag cagtgtcttc tgacagacag ctggccctga agtggttccc ttcacccaca    64020
ccatcctttg ccccagagga ggtattgagt gggtcagtgc acgtgaactg ccagtgtcat    64080
ttgccaaaga gctgttgaca cacgctgaca tttcttttgc tgaaaatcat aagggctttg    64140
agcttccctc tgtccaggca catggtcagg ctgacccggt agctctgccc ctgctgacct    64200
gccatttttg tccacaacag ttatccatga gcagaaacat ttgtgtaact gaggcagaaa    64260
cttagttcaa gtaaaatgtc actaaattcg agtcagtttt tgtcttagac cctaaatgaa    64320
accaaatttt cataaatttt cttgttttaa agaaaaattt aatgagctac atttaaactg    64380
agaacatcag atagtgtctg agattatcaa aatagaacat caaaagtatt tttctgaatg    64440
aactgaacca aaccagaatg aaagggcaag ccctggggag cctgtctcca agccttctct    64500
gaaagggagt ctgtatttgg tgataactgc tcagcctctc caaagggcct cacctgctgt    64560
ctctcccagt tttatttta attgcctgtg agttttctgt gcagggtaag gcacctacat    64620
tctatgccag cagcctgatc aggtcctggg taatgtttga aatggctaca cagaggagtt    64680
tcaaagcctt ttgttcaatc tggcttcacc tcgtagacgg tgagaaagcg tcagagccct    64740
gcaggatccc gttgccacgt ttgaccgggg agccgatggg tttggaagtc tgagccctgt    64800
ctgcacaacc tgccccggtc agcagcttcg tgccccacc cccatctccc catgaggcag    64860
gcatctgtgc tgaccatggc ttccatgttc agaaaccccc aggcctttga gttatcatga    64920
agcttgtggg atgtgctcca agcctcctgc catagaaaaa ctgccatatt gctcacaata    64980
attcactatt atttgtttcc ccagttaaaa tgcgcacaat actggccaca aaagaagaa    65040 aaagagatga tctttgaaga cacaaatttg aaattaacat tgatctctga agatatcaag    65100
tcatattata cagtgcgaca gctagaattg gaaaacctta cagtgagtat agcacacact    65160
tcagcacttc aggcggctac tggttcacat gcctcttcct ttatcccttg ggtgatatta    65220
cctaatgtca gtgttcctgg cttttgtata ccccgagcaa gatgtggttt gggcactgtg    65280
gtgagcggag cttacttgtg tacctaccaa gtgcccaggg agggtggagg ccacagtgct    65340
ctctctgacc tttaacaaca gttaacacca gttcttaggg aaaggagagt tcttaccca    65400 aaagactggt tcctgcttgt gcagctgcag agggactgga gcggcagcct gcaagtccca    65460
gtgaagcatg ctgccttctt tgtggtcctc agtcttcgag tctgaagaga gggaagaagg    65520
ggtatagggg ctcactccag tttcatagct agtgaaagtt ttctgggcca ggtcttgggt    65580
ttttttgttg tgggaagagt ttataacacc agctacttgc ttggtaaaag ttggtcttgg    65640
aacatggcaa ggcattgtgg caagcagcac tgccgctgaa cgcgctgctc ctggggcttt    65700 ggataattc ccctggatcc gtaacttggg ggtgttcatg tcattctggg gaacagtgga    65760
gggagtgcgc ggcagcacct gggggcacca gtgaagagtg gccagccacc aacctctaga    65820
acctaactgg ggtcgaatcc tggccccacc ttactagctc atcacagtgt ctccgtttcc    65880
tcttctgtca aactcaggtt ttgcgagggt tctgggaggt cctatacggg aagggttagc    65940
agttaccatg ggtgtgtagc acgggcttta tctgaaggga aggtggagcc gtagggagac    66000
catgtggagt ggggctccag ggctgtgtgg gtggggaggg atctgcttct gggttacccc    66060
atgcctcccc ttctcaagta ctactttta atcatcatgg ctcctgccat tcatttcata    66120
gttgatgtaa gccaggtgcg gtggctcacg tctttaatcc cagcacttgg ggaggctgag    66180
gccaggagga tcactcgagg ccaggagttc aagaccagct tgggcaacat agtgagaccc    66240
ccgtctctac aaaaaaacaa aaacagttag tcagacatcg tggtgctccc ctatagtcca    66300
gctactcagg aggctgaggc aggaggattg cttgtgcccg ggagttcaag gctgcagtga    66360
```

```
gctatgcttg caccactgca ctctagcctg ggtgacagag caagaccctg tctcaaaaat   66420
aaataaataa aaaaaatagt agaagtaaga tctagaatgt agcacaggtt accaggacgt   66480
aggcaagggg ttcgggctgc ctggctcttg aggatggtag cagtgcagct gatgtgagtg   66540 cttctgccc tctggtggtg accgcgccgg agtcaccagc cctgccatag ccctgatggg    66600
gcagagggtt ctgagtacgg tggatggagg tgctttctgg aagattctca ggagtaacat   66660
gggcagtgtg ttggaatgtg ctagaggatt tatgcagtag cctttttaaaa gaatgctttt   66720 tagcatttgc aagcctgaca ttaagagtga cttctgggaa actatttgct tgttgaggga   66780
aactgaattt caacagagca gaagagctgt gcgcttttg cttggcagag tgaatacagc    66840
cagctcagag gttttgatgt taggatctgt ttgctccaac agactttgtt tttaaaaggc   66900
tttcctcagc catagctgtc tgttctagca caaggctgga atgagttcct tgtgaaagag   66960
gtgagcaggt gtgagggagg gtgtcagtgg gcggtaaccc acaccttcaa ggattaaagg   67020
aaaacttgca tttggcatgc ttgcttctta ttcaattta aaatacattt taacggccgg    67080
gcacggtggc taacacctgt aatcccagca ctttgagggg ctgaggtggg tggttcacga   67140 ggccagggggt tcaagaccag cctggccaag atggtgaaac cccatctcta ctaaaaatac   67200
aaaaaaaaaa aaaattagcc gggcgtggtg gcgggcacct gtaatcccag ctactcggga   67260
ggctgaggca gagaattgct tgaacccagg aggcggaggt tgcattgagc cgagatcatg   67320
ccactgcatt ccagcctggg cggcagagca agactctgtc tcaaaataat aataataatt   67380
ttttaaaaat acattttaag tccttttctt ccccacctgc ctccacccac caaatagaag   67440
aggtatttct tcttctttaa tgtcattaag gttatatgga taccattttc tagagaggaa   67500
agaatgatgg aattgcctag tgtgagtcta gcaattatcc taacatacac aaatttctcc   67560
ttgttctgtg ccaagatact gtatttaata tttaatgaac attaaatatt atttactagt   67620
gtatttaatg gctgaggcag ggttaaatat gtattatttt catcccagca gagttggggg   67680
aggtcctagt aactatgcca tgagctctgt gagggtgagg tggtgtcttt gccccgcct    67740 ccctggcaca gtgactggca catgattggc atagtgtgga cattcgtcaa gtgaaggaag   67800
gcatcatgag cagatctctg gcctgaatcc ttctgccatc agctgctcgc caggtggccc   67860
tggcactggg ccacagggaa actctccagg ctggtatggt tcctgtctgt ggctgtcttc   67920
ccgggcccat gttaggagac tttcacttcc agagcccttt ccctctcagg gccttgctta   67980
ccaagtgact ggttcccatt tactaggagc tcttaggtca ttgaagatgt tgcgtactcc   68040
ccccagtgag ggctgccttt tgatcacagc cgccagaagc ctcaaggaag gagcagagct   68100
ggaaacagac gccaggccat tgcttctgtt cctctgggc agacccagcc acggaagaga    68160
cattctggga caagggctgg ggtccacctt tcaaacgtgt ctgcagcagg ctctcagcat   68220
ggactctctg cctccaaaca tccacctcct catcggaaaa tggatgggag tgcctgcctg   68280
gagcagctgg tgggagagcg cagcgccagc acgtaggaca cactcggttc atgggctgat   68340
gccgttcgca ttgactgcct cttcagctgg gtgttgagcc acaccttgga gtcaccagtc   68400
tttggagacc aagtctgcta ctttttctc taaagtgaca atcctctgaa acctccagat    68460
catcttgaag ccccgtctg aaagttgccc agagccagtg cctcacctgc tgttccttgt    68520
tcactttttc acgggaggcc ttgcagggct ttatgacaag attttatggg tggctgccca   68580
gcatcattgt gactcgtgag acagagagaa accagttgta accatgtaga cagtggaagt   68640
gatagggaga aagaggtga ggggactctt caatccgaag ggaaatgaag tctaagcagg    68700
```

```
cgcaccctgc aggttcagtg tcaagcccag ggcctggccc cagggtgtgg tatttgttga   68760
ctgggtgtgt ggaccctggg agaaagtctg agaatgaatg ttcctcttag aggtagagag   68820
tggaaggtga ctctgtgtgt acttggaatt agtgatttct gtacagatga ttcttttaga   68880
atcatcatga gtattttcct ctttcagacc caagaaactc gagagatctt acatttccac   68940
tataccacat ggcctgactt tggagtccct gaatcaccag cctcattctt gaactttctt   69000
ttcaaagtcc gagagtcagg gtcactcagc ccggagcacg ggcccgttgt ggtgcactgc   69060
agtgcaggca tcggcaggtc tggaaccttc tgtctggctg atacctgcct cttgctggta   69120
aggaggccct cgcgggtgcc ctggggagct cctctacctg ctctgctgtg atgttttttc   69180
ctaagtagaa actgaagcgc tcctcttcca aaatacagag actcactgtg ttagtctgtt   69240
tttgcgttac taataaaggc gtacctgaga ctcggtaatt tgtaaagaaa agaggtttaa   69300
ctggctcccg gttctgcagg ctgtacaagc atggcaccag catctgctcg gctcctgggg   69360
aggcctcagg gagcttccag tcatggtgga aggtgaaggg gagcaggagc aagagatggg   69420
ggaggtccca gactcttaac cagctctctt gtgaatgcat tgcctcaggg agggcaccaa   69480
gcctttcatg agggacctgt cccctgaccc cagacacctc ccacccagcc ccacctccaa   69540
cactagggat cacatttcag catgagattg ggaggggaca gacatctaac ggtgttatta   69600
acgttgccct tgagaattgg acctggctga cttatatctc ctctctggct ttcagatgga   69660
caagaggaaa gacccttctt ccgttgatat caagaaagtg ctgttagaaa tgaggaagtt   69720
tcggatgggg ctgatccaga cagccgacca gctgcgcttc tcctacctgg ctgtgatcga   69780
aggtgccaaa ttcatcatgg gggactcttc cgtgcaggtc agcattgcct tgtttgaat   69840 ccaggtgtga ccattttaac tttttttgtct ttgaaggagg ctgtcagttg taaaagttca   69900
aacaccgtct ggtgtcaggg gaaatagcta cccttcatgt ttaaaatagc tagaaagttg   69960
tcaaaatgtt caccatgttg cactttgtgc ctttgaagtg ctcacataga gagcattgat   70020
aggaagacga gactttattt tcaaaagatt tcatcttcca agtacatggc tgcagccctg   70080
agaggccgag agcccctcgc caagccgtca cctctgctca tgcaaaggga tttcctgaca   70140
aaccagccga agtgaacact aataggactt cctcttgctg ctctttcaag gatcagtgga   70200
aggagctttc ccacgaggac ctggagcccc cacccgagca tatcccccca cctccccggc   70260
cacccaaacg aatcctggag ccacacaatg ggaaatgcag ggagttcttc ccaaatcacc   70320
agtgggtgaa ggaagagacc caggaggata aagactgccc catcaaggaa gaaaaaggaa   70380 gcccccttaaa tgccgcaccc tacggcatcg aaagtaata tgattgggtc ccagcttgtt   70440
ggggtgaggg gaaatgactt tctgttctag aaacacacgc tggtactgaa accctgtgga   70500
tgcagcctcc tgttggcaag cagcgcttcc gcatccttgg ggaacagggc gcgtggacca   70560
cagccactcc actcctggct gctggaggtc cggtattggg cacagggtgg ccgcaggaca   70620
tgagccactt ctgtgggctt ctagtgccac cttgtggtgc ttgttggaat gaggggctcg   70680
gagccaccga gtagggtttt tctgcccccc ctgacgacag cgccctcccc caggtttccg   70740
gacagtcctg aaatgtgatg tccaggcttg agtgccctca gtccccacag tggtcctttg   70800
gggaatgtaa cctttttat gtggtcttga ttaaatccca tttacttcc ttgcaggtta   70860 acaaccatta ttgagtacct attgatatgt gtggtgtact gagttaacta gaacatgtcc   70920
cctggtctgt gttctagacc atcttgctgg gaaaaggca gacccaaagc atattttggt   70980
gggggcccat ggacagtgat gtgatagagg tgtccgctga ggtggtcagg gaaggctgct   71040
tgcagtaggt ggccgtgcac ggaaagtttg cagaatgagc aggtgttagt tccagctgga   71100
```

```
gatgactgcc ggctgtgccc ttggtacctg cttctggag ggaagtttta agacgtgtgc    71160
atacttgacc cagcagttgt atacatggag aaatttactt tgcagcaact ctcaaaacaa    71220
gcgtgtaaag atgtgtatag gtagttgtgt ttgttgtggc attgtttgta gtagtgaaaa    71280
attagagaca ggccaatgat ataaccaggg acctgatcaa ttatgttctc tcccggtgtt    71340
gggatattct gtagctctta aagaatgaga tctgggtgta ctgatgtggc cagacattgc    71400
aattgcagta catgagaagg caaatcatac agtagtgtgt acaccagtga gtcctccagc    71460
cagataaatc ctcacagtga ccagtcgccc aggcaccttg tgaaccctac cctgggtgtg    71520
ggtgctatct gaagtacctg ggggagggg tgacaagtgg acttcaggct gatgtgggcc    71580
ctggcctggc cctccctcca agcagagggg gctggctcgc tggaaggtta acatcatcca    71640
actctgtcta cacgtggctt gttttttcct agaattcctg ccacaatagc agcatccttg    71700
ccattcattt tctccaaagt gagtaaccca tctctgccct ctgattcctc agcatgagtc    71760
aagacactga agttagaagt cgggtcgtgg ggggaagtct tcgaggtgcc caggctgcct    71820
ccccagccaa aggggagccg tcactgcccg agaaggacga ggaccatgca ctgagttact    71880
ggaagccctt cctggtcaac atgtgcgtgg ctacggtcct cacggccggc gcttacctct    71940
gctacagggt atgtttccac tgacagacgc gctggcgaga tgctcgtgtg cagagagcac    72000
tggccgctag cccgatggta ggattcagtt ctgtggtgca tctgagccag tctcagaaga    72060
aacagatcaa aggttttaa agtctggaac tgtggaaggg ctaacaagag aattaaggat    72120
cgatgcactg gggttttaag gagccctctg gtcccaagaa tataagagtc taatctcagg    72180
gccttaacct attcaggagt aagtagagaa atgccaaat acgtctgttt ctctctctct    72240
tttttttttt attcctttgt ttttggaaaa aaatagagtt acaacacatt gttgtttta    72300 accttatata aaagcagctt tttgttattt ctggaacaaa aaaaacaaa gtaggcactt    72360 atgaaacttt ctcataccct taggtgatgt aatcagccat ataatttata ttgattcc    72420 cagggaagga atcccaaact tttacgaatg taaactccct tggagaagag ggttaggacg    72480
ctgttgcgct caagccccccc tcagctgtgt gcacactgag ccaggacagg gtctttgagc    72540
tttcccacta taagaagaac agcaacaaaa ggccgtctag aaaaacagaa cctgcctctg    72600
cttctgctca gggtgtcccc gctgggtttc cattgtcctt tctccattgc tccctcctgt    72660
gacagccatc ttgctcatgt accagccctc atcaccccat cccataaat gggtgtcctc    72720 gaggcctctg cctgggggtc agaggtcacc acagggtggc cattggcatg tcaacccgct    72780
gttaattcag agaagtgggc tccacctcat ttgggagaagt gccatttcag cagaaattca    72840
cacgttagac gtgtgttgct gttaagtaag gggaagagag aggactagcc tcagagctct    72900
ggccatggaa atgacctcct aagacttttt cgtggtttta aatattttac ctctttccag    72960
gtggcatctg agtacatcag atggttttgc aaaatgcaaa caattttttc cttggggatg    73020
atttttgggg agaggggct actgtaaaaa ataaaaccaa aacccccttt gctccctcgg    73080
aggttgaagt tgccggggg tgtggccggg gtcatgcatg aggcgacagc tctgcaggtg    73140
cgggtctggg ctcatctgaa ctgtttggtt tcattccagt tcctgttcaa cagcaacaca    73200
tagcctgacc ctcctccact ccacctccac ccactgtccg cctctgcccg cagagcccac    73260
gcccgactag caggcatgcc gcggtaggta agggccgccg gaccgcgtag agagccgggc    73320 cccgacgga cgttggttct gcactaaaac ccatcttccc cggatgtgtg tctcacccct    73380 catccttta cttttgccc cttccacttt gagtaccaaa tccacaagcc atttttgag    73440
```

```
gagagtgaaa gagagtacca tgctggcggc gcagagggaa ggggcctaca cccgtcttgg    73500
ggctcgcccc acccagggct ccctcctgga gcatcccagg cgggcggcac gccaacagcc    73560
ccccccttga atctgcaggg agcaactctc cactccatat ttatttaaac aattttttcc    73620
ccaaaggcat ccatagtgca ctagcatttt cttgaaccaa taatgtatta aaattttttg    73680
atgtcagcct tgcatcaagg gctttatcaa aaagtacaat aataaatcct caggtagtac    73740
tgggaatgga aggctttgcc atgggcctgc tgcgtcagac cagtactggg aaggaggacg    73800
gttgtaagca gttgttattt agtgatattg tgggtaacgt gagaagatag aacaatgcta    73860
taatatataa tgaacacgtg ggtatttaat aagaaacatg atgtgagatt actttgtccc    73920
gcttattctc ctccctgtta tctgctagat ctagttctca atcactgctc ccccgtgtgt    73980
attagaatgc atgtaaggtc ttcttgtgtc ctgatgaaaa atatgtgctt gaaatgagaa    74040
actttgatct ctgcttacta atgtgcccca tgtccaagtc caacctgcct gtgcatgacc    74100
tgatcattac atggctgtgg ttcctaagcc tgttgctgaa gtcattgtcg ctcagcaata    74160
gggtgcagtt ttccaggaat aggcatttgc ctaattcctg gcatgacact ctagtgactt    74220
cctggtgagg cccagcctgt cctggtacag cagggtcttg ctgtaactca gacattccaa    74280
gggtatggga agccatattc acacctcacg ctctggacat gatttaggga agcagggaca    74340
ccccccgccc cccacctttg ggatcagcct ccgccattcc aagtcaacac tcttcttgag    74400
cagaccgtga tttggaagag aggcacctgc tggaaaccac acttcttgaa acagcctggg    74460
tgacggtcct ttaggcagcc tgccgccgtc tctgtcccgg ttcaccttgc cgagagaggc    74520
gcgtctgccc caccctcaaa ccctgtgggg cctgatggtg ctcacgactc ttcctgcaaa    74580
gggaactgaa gacctccaca ttaagtggct ttttaacatg aaaaacacgg cagctgtagc    74640
tcccgagcta ctctccttgcc agcatttcca cattttgcct ttctcgtggt agaagccagt    74700
acagagaaat tctgtggtgg gaacattcga ggtgtcaccc tgcagagcta tggtgaggtg    74760
tggataaggc ttaggtgcca ggctgtaagc attctgagct gggcttgttg tttttaagtc    74820
ctgtatatgt atgtagtagt ttgggtgtgt atatatagta gcatttcaaa atggacgtac    74880
tggtttaacc tcctatcctt ggagagcagc tggctctcca ccttgttaca cattatgtta    74940
gagaggtagc gagctgctct gctatatgcc ttaagccaat atttactcat caggtcatta    75000
ttttttacaa tggccatgga ataaaccatt tttacaaaaa taaaaacaaa aaagcaagg    75060 tgttttggta taatacctTT tcaggtgtgt gtggatacgt ggctgcatga ccgggtgggt    75120
gggggggagt gtctcagggt cttctgtgac ctcacagaac tgtcagactg tacagttttc    75180
caacttgcca tattcatgat gggtttgcat tttagctgca acaataaaat ttttttctaa    75240
agaacatgaa tttggggtgc ttcccatttt tttctttgct taatagagct aaaccaggat    75300
gagtaactcc tgtttctttc tatccctgct gatgtgaaac agatgttgtc aatcagctgg    75360
ggttagagtt ttccacttct aagaattaac ctcagcatcc ctgcattgcc agcaccctca    75420
ggctggagcg ctttccttga ctgtgagctt gttgaacacc ttaggcctca gcccatttcc    75480
ttcccaaatt gacgctttgc ctgtgtaggg ccctcagata acttaacaaa cttaccagtg    75540
ttgtttgaag aacagtgttt tgagttgtaa tctcaaaacc atatccctta cccaattacc    75600
tgtaagacac aatggttacc acatctcagt acgtaaagtc cacttgatat agaattgact    75660
tagaaataag acagattagt atagtttttc atttgtgtac aaaattaaac aatgtaaatt    75720 cccccccaaag tgatttttttt gacttttga agtaattttg gacttgcaaa atgttgccaa    75780
aatagtacga agagttcccc agtaccctcg aagtttcctc gactgtttca aagctggctg    75840
```
caggcccagg ctcatgagac tgggaagagg acaggctgtg gtcatgtgga cccacaggg    75899

<210> SEQ ID NO 244
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 244
gcgctcttag ccccgaggcc                                              20

<210> SEQ ID NO 245
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 245
ccagggcggc tgctgcgcct                                              20

<210> SEQ ID NO 246
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 246
catctccatg acgggccagg                                              20

<210> SEQ ID NO 247
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 247
ttttccatct ccatgacggg                                              20

<210> SEQ ID NO 248
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 248
actccttttc catctccatg                                              20

<210> SEQ ID NO 249
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 249
ttgtcgatct gctcgaactc                                              20

<210> SEQ ID NO 250
<211> LENGTH: 20
<212> TYPE: DNA

```
<213> ORGANISM: Artificial Sequence
<220> FEATURE:
<223> OTHER INFORMATION: Synthetic Oligonucleotide

<400> SEQUENCE: 250
gacttgtcga tctgctcgaa                                              20

<210> SEQ ID NO 251
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 251
gctcccggac ttgtcgatct                                              20

<210> SEQ ID NO 252
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 252
ccagctcccg gacttgtcga                                              20

<210> SEQ ID NO 253
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 253
tccactgatc ctgcacggaa                                              20

<210> SEQ ID NO 254
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 254
ccttccactg atcctgcacg                                              20

<210> SEQ ID NO 255
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 255
atgcctgcta gtcgggcgtg                                              20

<210> SEQ ID NO 256
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 256
cgggtgtagg cccctteect                                              20
```

<210> SEQ ID NO 257
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 257
atggagtgga gagttgctcc                                               20

<210> SEQ ID NO 258
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 258
ttgtactttt tgataaagcc                                               20

<210> SEQ ID NO 259
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 259
cagtactggt ctgacgcagc                                               20

<210> SEQ ID NO 260
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 260
tctcacgtta cccacaatat                                               20

<210> SEQ ID NO 261
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 261
tttcttatta aatacccacg                                               20

<210> SEQ ID NO 262
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 262
aagtaatctc acatcatgtt                                               20

<210> SEQ ID NO 263
<211> LENGTH: 20
<212> TYPE: DNA
<213> ORGANISM: Artificial Sequence
<220> FEATURE:

<223> OTHER INFORMATION: Synthetic Oligonucleotide

<400> SEQUENCE: 263
ttcagcaaca ggcttaggaa                                                     20

<210> SEQ ID NO 264
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 264
gacaatgact tcagcaacag                                                     20

<210> SEQ ID NO 265
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 265
tgcctattcc tggaaaactg                                                     20

<210> SEQ ID NO 266
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 266
ggaagtcact agagtgtcat                                                     20

<210> SEQ ID NO 267
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 267
ccaggacagg ctgggcctca                                                     20

<210> SEQ ID NO 268
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 268
ctgctgtacc aggacaggct                                                     20

<210> SEQ ID NO 269
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 269
tggaatgtct gagttacagc                                                     20

```
<210> SEQ ID NO 270
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 270
agagtgttga cttggaatgg                                               20

<210> SEQ ID NO 271
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 271
gctcaagaag agtgttgact                                               20

<210> SEQ ID NO 272
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 272
tgcctctctt ccaaatcacg                                               20

<210> SEQ ID NO 273
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 273
tgtttttcat gttaaaaagc                                               20

<210> SEQ ID NO 274
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 274
tcccaccaca gaatttctct                                               20

<210> SEQ ID NO 275
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 275
gctctgcagg gtgacacctc                                               20

<210> SEQ ID NO 276
<211> LENGTH: 20
<212> TYPE: DNA
<213> ORGANISM: Artificial Sequence
<220> FEATURE:
<223> OTHER INFORMATION: Synthetic Oligonucleotide
```

```
<400> SEQUENCE: 276
aggaggttaa accagtacgt                                              20

<210> SEQ ID NO 277
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 277
ggtggagagc cagctgctct                                              20

<210> SEQ ID NO 278
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 278
tattggctta aggcatatag                                              20

<210> SEQ ID NO 279
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 279
gacctgatga gtaaatattg                                              20

<210> SEQ ID NO 280
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 280
ttcttcatgt caaccggcag                                              20

<210> SEQ ID NO 281
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 281
gccccgaggc ccgctgcaat                                              20

<210> SEQ ID NO 282
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 282
tagtgaacta ttgttacaac                                              20

<210> SEQ ID NO 283
<211> LENGTH: 20
```

```
<212> TYPE: DNA
<213> ORGANISM: Artificial Sequence
<220> FEATURE:
<223> OTHER INFORMATION: Synthetic Oligonucleotide

<400> SEQUENCE: 283
tgctaagcca cttctaatca                                              20

<210> SEQ ID NO 284
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 284
caggattcta agttattaaa                                              20

<210> SEQ ID NO 285
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 285
tgggcaggat ggctctggta                                              20

<210> SEQ ID NO 286
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 286
tacaatacta tctgtgacta                                              20

<210> SEQ ID NO 287
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 287
gatacttaca gggactgacg                                              20

<210> SEQ ID NO 288
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 288
aaccctgagg cgaaaggagt                                              20

<210> SEQ ID NO 289
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 289
```

```
ccccaggtca ctaaaattaa                                              20

<210> SEQ ID NO 290
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 290
aaagcaaagg tgagttggtg                                              20

<210> SEQ ID NO 291
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 291
gctcaattat taaaccactt                                              20

<210> SEQ ID NO 292
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 292
agtcctcaag aagtcacttt                                              20

<210> SEQ ID NO 293
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 293
gaaagcaggg actgctggca                                              20

<210> SEQ ID NO 294
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 294
aaaactggga gagacagcag                                              20

<210> SEQ ID NO 295
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 295
acatggaagc catggtcagc                                              20

<210> SEQ ID NO 296
<211> LENGTH: 20
<212> TYPE: DNA
<213> ORGANISM: Artificial Sequence
```

```
<220> FEATURE:
<223> OTHER INFORMATION: Synthetic Oligonucleotide

<400> SEQUENCE: 296
attgctagac tcacactagg                                              20

<210> SEQ ID NO 297
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 297
ggctgtgatc aaaaggcagc                                              20

<210> SEQ ID NO 298
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 298
cactggctct gggcaacttt                                              20

<210> SEQ ID NO 299
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 299
gctgggcagc cacccataaa                                              20

<210> SEQ ID NO 300
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 300
agtcccctca cctctttcct                                              20

<210> SEQ ID NO 301
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 301
cctccttacc agcaagaggc                                              20

<210> SEQ ID NO 302
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 302
tgtattttgg aagaggagcg                                              20
```

<210> SEQ ID NO 303
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 303
acagactaac acagtgagtc					20

<210> SEQ ID NO 304
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 304
acaaattacc gagtctcagg					20

<210> SEQ ID NO 305
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 305
tcatgaaagg cttggtgccc					20

<210> SEQ ID NO 306
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 306
ttggaagatg aaatcttttg					20

<210> SEQ ID NO 307
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 307
agccatgtac ttggaagatg					20

<210> SEQ ID NO 308
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 308
cgagcccctc attccaacaa					20

<210> SEQ ID NO 309
<211> LENGTH: 20
<212> TYPE: DNA
<213> ORGANISM: Artificial Sequence
<220> FEATURE:
<223> OTHER INFORMATION: Synthetic Oligonucleotide

```
<400> SEQUENCE: 309
cacctcagcg gacacctcta                                               20

<210> SEQ ID NO 310
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 310
gaaacatacc ctgtagcaga                                               20

<210> SEQ ID NO 311
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 311
cagagggctc cttaaaaccc                                               20

<210> SEQ ID NO 312
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 312
attcgtaaaa gtttgggatt                                               20

<210> SEQ ID NO 313
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 313
ccctcttctc caagggagtt                                               20

<210> SEQ ID NO 314
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 314
ggaatgaaac caaacagttc                                               20

<210> SEQ ID NO 315
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 315
aaatggttta ttccatggcc                                               20

<210> SEQ ID NO 316
```

```
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 316
aaaaatttta ttgttgcagc                                                     20

<210> SEQ ID NO 317
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 317
ccggtcatgc agccacgtat                                                     20

<210> SEQ ID NO 318
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 318
gttggaaaac tgtacagtct                                                     20

<210> SEQ ID NO 319
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 319
attttattgt tgcagctaaa                                                     20

<210> SEQ ID NO 320
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 320
cgcctccttc tcggcccact                                                     20

<210> SEQ ID NO 321
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 321
gggcggctgc tgcgcctcct                                                     20

<210> SEQ ID NO 322
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 322
```

```
gtggatttgg tactcaaagt                                          20

<210> SEQ ID NO 323
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 323
aaatggcttg tggatttggt                                          20

<210> SEQ ID NO 324
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 324
atggtactct ctttcactct                                          20

<210> SEQ ID NO 325
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 325
gccagcatgg tactctcttt                                          20

<210> SEQ ID NO 326
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 326
gagagttgct ccctgcagat                                          20

<210> SEQ ID NO 327
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 327
ggagtggaga gttgctccct                                          20

<210> SEQ ID NO 328
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 328
ccttgatgca aggctgacat                                          20

<210> SEQ ID NO 329
<211> LENGTH: 20
<212> TYPE: DNA
```

```
<213> ORGANISM: Artificial Sequence
<220> FEATURE:
<223> OTHER INFORMATION: Synthetic Oligonucleotide

<400> SEQUENCE: 329
aaagcccttg atgcaaggct                                               20

<210> SEQ ID NO 330
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 330
agtactacct gaggatttat                                               20

<210> SEQ ID NO 331
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 331
ttccattccc agtactacct                                               20

<210> SEQ ID NO 332
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 332
ccatggcaaa gccttccatt                                               20

<210> SEQ ID NO 333
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 333
caggcccatg gcaaagcctt                                               20

<210> SEQ ID NO 334
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 334
caactgctta caaccgtcct                                               20

<210> SEQ ID NO 335
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 335
ccacgtgttc attatatatt                                               20
```

<210> SEQ ID NO 336
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 336
ttaaataccc acgtgttcat                                                    20

<210> SEQ ID NO 337
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 337
taagcgggac aaagtaatct                                                    20

<210> SEQ ID NO 338
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 338
cagataacag ggaggagaat                                                    20

<210> SEQ ID NO 339
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 339
gagaactaga tctagcagat                                                    20

<210> SEQ ID NO 340
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 340
agtgattgag aactagatct                                                    20

<210> SEQ ID NO 341
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 341
gacacaagaa gaccttacat                                                    20

<210> SEQ ID NO 342
<211> LENGTH: 20
<212> TYPE: DNA
<213> ORGANISM: Artificial Sequence
<220> FEATURE:

<223> OTHER INFORMATION: Synthetic Oligonucleotide

<400> SEQUENCE: 342
ctcatttcaa gcacatattt                                              20

<210> SEQ ID NO 343
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 343
ggcaggttgg acttggacat                                              20

<210> SEQ ID NO 344
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 344
aaccacagcc atgtaatgat                                              20

<210> SEQ ID NO 345
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 345
ttgctgagcg acaatgactt                                              20

<210> SEQ ID NO 346
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 346
ctggaaaact gcaccctatt                                              20

<210> SEQ ID NO 347
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 347
gctgggcctc accaggaagt                                              20

<210> SEQ ID NO 348
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 348
ttacagcaag accctgctgt                                              20

```
<210> SEQ ID NO 349
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 349 accccttggaa tgtctgagtt                                              20

<210> SEQ ID NO 350
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 350
ttcccatacc cttggaatgt                                               20

<210> SEQ ID NO 351
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 351
atatggcttc ccataccctt                                               20

<210> SEQ ID NO 352
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 352
gtgtgaatat ggcttcccat                                               20

<210> SEQ ID NO 353
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 353
cctgcttccc taaatcatgt                                               20

<210> SEQ ID NO 354
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 354
gtgtccctgc ttccctaaat                                               20

<210> SEQ ID NO 355
<211> LENGTH: 20
<212> TYPE: DNA
<213> ORGANISM: Artificial Sequence
<220> FEATURE:
<223> OTHER INFORMATION: Synthetic Oligonucleotide
```

```
<400> SEQUENCE: 355
cggaggctga tcccaaaggt                                                   20

<210> SEQ ID NO 356
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 356
caggtgcctc tcttccaaat                                                   20

<210> SEQ ID NO 357
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 357
gtggtttcca gcaggtgcct                                                   20

<210> SEQ ID NO 358
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 358
gctgtttcaa gaagtgtggt                                                   20

<210> SEQ ID NO 359
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 359
ggaccgtcac ccaggctgtt                                                   20

<210> SEQ ID NO 360
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 360
caggctgcct aaaggaccgt                                                   20

<210> SEQ ID NO 361
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 361
accatcaggc cccacagggt                                                   20

<210> SEQ ID NO 362
<211> LENGTH: 20
```

```
<212> TYPE: DNA
<213> ORGANISM: Artificial Sequence
<220> FEATURE:
<223> OTHER INFORMATION: Synthetic Oligonucleotide

<400> SEQUENCE: 362
gttccctttg caggaagagt                                               20

<210> SEQ ID NO 363
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 363
gtggaggtct tcagttccct                                               20

<210> SEQ ID NO 364
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 364
ccacttaatg tggaggtctt                                               20

<210> SEQ ID NO 365
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 365
agctacagct gccgtgtttt                                               20

<210> SEQ ID NO 366
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 366
ccacgagaaa ggcaaaatgt                                               20

<210> SEQ ID NO 367
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 367
gaatttctct gtactggctt                                               20

<210> SEQ ID NO 368
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 368
```
ccacagaatt tctctgtact                                               20

<210> SEQ ID NO 369
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 369
gaatgttccc accacagaat                                               20

<210> SEQ ID NO 370
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 370
gcctggcacc taagccttat                                               20

<210> SEQ ID NO 371
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 371
atgcttacag cctggcacct                                               20

<210> SEQ ID NO 372
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 372
ctacatacat atacaggact                                               20

<210> SEQ ID NO 373
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 373
tttgaaatgc tactatatat                                               20

<210> SEQ ID NO 374
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 374
ggataggagg ttaaaccagt                                               20

<210> SEQ ID NO 375
<211> LENGTH: 20
<212> TYPE: DNA
<213> ORGANISM: Artificial Sequence

```
<220> FEATURE:
<223> OTHER INFORMATION: Synthetic Oligonucleotide

<400> SEQUENCE: 375
gccagctgct ctccaaggat                                          20

<210> SEQ ID NO 376
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 376
ctacctctct aacataatgt                                          20

<210> SEQ ID NO 377
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 377
gctcgctacc tctctaacat                                          20

<210> SEQ ID NO 378
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 378
aggcatatag cagagcagct                                          20

<210> SEQ ID NO 379
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 379
gtcaaccggc agccggaact                                          20

<210> SEQ ID NO 380
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 380
cctgcagcta ccgccgccct                                          20

<210> SEQ ID NO 381
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 381
cgctgcaatc cccgacccct                                          20
```

<210> SEQ ID NO 382
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 382
accaaaacac cttgcttttt            20

<210> SEQ ID NO 383
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 383
gtattatacc aaaacacctt            20

<210> SEQ ID NO 384
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 384
cacacacctg aaaaggtatt            20

<210> SEQ ID NO 385
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 385
acccggtcat gcagccacgt            20

<210> SEQ ID NO 386
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 386
gtgaggtcac agaagaccct            20

<210> SEQ ID NO 387
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 387
gtacagtctg acagttctgt            20

<210> SEQ ID NO 388
<211> LENGTH: 20
<212> TYPE: DNA
<213> ORGANISM: Artificial Sequence
<220> FEATURE:
<223> OTHER INFORMATION: Synthetic Oligonucleotide

```
<400> SEQUENCE: 388
atggcaagtt ggaaaactgt                                              20

<210> SEQ ID NO 389
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 389
aatgcaaacc catcatgaat                                              20

<210> SEQ ID NO 390
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 390
uucaugucgg auauccuggt a                                            21

<210> SEQ ID NO 391
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 391
ucacuggcuu caugucggat a                                            21

<210> SEQ ID NO 392
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 392
gguaagaaug uaacuccuut g                                            21

<210> SEQ ID NO 393
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 393
cuucagagau caauguuaat t                                            21

<210> SEQ ID NO 394
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 394
uagcugucgc acuguauaat a                                            21

<210> SEQ ID NO 395
```

```
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 395
ccaauucuag cugucgcact g                                            21

<210> SEQ ID NO 396
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 396
uugauaaagc ccuugaugca                                              20

<210> SEQ ID NO 397
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 397
ggucaugcac aggcagguug                                              20

<210> SEQ ID NO 398
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 398
gaagaagggu cuuccucuu                                               20

<210> SEQ ID NO 399
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 399
ctgctagcct ctggatttga                                              20

<210> SEQ ID NO 400
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 400
tagtgcggac ctacccacga                                              20

<210> SEQ ID NO 401
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 401
```
gggacgaacu gguguaaugt t                                              21

<210> SEQ ID NO 402
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 402
cuucuggcau ccgguuuagt t                                              21

<210> SEQ ID NO 403
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 403
ccaggauauc cgacaugaag c                                              21

<210> SEQ ID NO 404
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 404
uccgacauga agccagugac t                                              21

<210> SEQ ID NO 405
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 405
aaggaguuac auucuuaccc a                                              21

<210> SEQ ID NO 406
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 406
uuaacauuga ucucugaaga t                                              21

<210> SEQ ID NO 407
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 407
uuauacagug cgacagcuag a                                              21

<210> SEQ ID NO 408
<211> LENGTH: 21
<212> TYPE: DNA

```
<213> ORGANISM: Artificial Sequence
<220> FEATURE:
<223> OTHER INFORMATION: Synthetic Oligonucleotide

<400> SEQUENCE: 408
gugcgacagc uagaauugga a                                              21

<210> SEQ ID NO 409
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 409
ugcaucaagg gcuuuaucaa                                                20

<210> SEQ ID NO 410
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 410
caaccugccu gugcaugacc                                                20

<210> SEQ ID NO 411
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 411
ucucuugcca gcauuuucac                                                20

<210> SEQ ID NO 412
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 412
cauuacacca guucguccct t                                              21

<210> SEQ ID NO 413
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 413
cuaaaccgga ugccagaagt t                                              21

<210> SEQ ID NO 414
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 414
cgagaggcgg  acgggaccgt t                                             21
```

```
<210> SEQ ID NO 415
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 415
cggtcccgtc cgcctctcgt t                                              21
```